US011773408B2

(12) United States Patent
Carrier et al.

(10) Patent No.: US 11,773,408 B2
(45) Date of Patent: Oct. 3, 2023

(54) GENE-THERAPY VECTORS FOR TREATING CARDIOMYOPATHY

(71) Applicants: Lucie Carrier, Hamburg (DE); Thomas Eschenhagen, Hamburg (DE); Thomas Voit, London (GB); Giulia Mearini, Hamburg (DE); Oliver Mueller, Heikendorf (DE); Doreen Stimpel, Hamburg (DE)

(72) Inventors: Lucie Carrier, Hamburg (DE); Thomas Eschenhagen, Hamburg (DE); Thomas Voit, London (GB); Giulia Mearini, Hamburg (DE); Oliver Mueller, Heikendorf (DE); Doreen Stimpel, Hamburg (DE); Julia Mourot-Filiatre, Brasilia (BR)

(73) Assignees: Lucie Carrier, Hamburg (DE); Thomas Eschenhagen, Hamburg (DE); Thomas Voit, London (GB); Giulia Mearini, Hamburg (DE); Oliver Mueller, Dossenheim (DE); Doreen Stimpel, Hamburg (DE)

( * ) Notice: Subject to any disclaimer, the term of this patent is extended or adjusted under 35 U.S.C. 154(b) by 740 days.

(21) Appl. No.: 16/707,223

(22) Filed: Dec. 9, 2019

(65) Prior Publication Data

US 2020/0095609 A1 Mar. 26, 2020

Related U.S. Application Data

(62) Division of application No. 14/785,188, filed as application No. PCT/EP2014/057984 on Apr. 17, 2014, now Pat. No. 10,501,756.

(30) Foreign Application Priority Data

Apr. 17, 2013 (EP) .................................... 13164212
Dec. 18, 2013 (EP) .................................... 13198201

(51) Int. Cl.

| | |
|---|---|
| ***C12N 15/86*** | (2006.01) |
| ***C07K 14/47*** | (2006.01) |
| ***A61K 35/34*** | (2015.01) |
| ***C12N 5/074*** | (2010.01) |
| ***C12N 5/077*** | (2010.01) |
| ***A61K 48/00*** | (2006.01) |
| ***C12N 7/00*** | (2006.01) |

(52) U.S. Cl.

CPC .............. *C12N 15/86* (2013.01); *A61K 35/34* (2013.01); *A61K 48/0058* (2013.01); *C07K 14/4716* (2013.01); *C12N 5/0657* (2013.01); *C12N 5/0696* (2013.01); *C12N 7/00* (2013.01); *C12N 2506/45* (2013.01); *C12N 2750/14143* (2013.01); *C12N 2799/025* (2013.01); *C12N 2830/007* (2013.01); *C12N 2830/008* (2013.01)

(58) Field of Classification Search

CPC ...................................................... C12N 15/86
See application file for complete search history.

(56) References Cited

U.S. PATENT DOCUMENTS

| | | | | |
|---|---|---|---|---|
| 5,591,624 | A | 1/1997 | Barber et al. | |
| 8,933,048 | B2 * | 1/2015 | Stelzer | A61K 31/7088 424/93.1 |
| 2002/0127548 | A1 | 9/2002 | Siedman et al. | |
| 2004/0086876 | A1 | 5/2004 | Seidman et al. | |
| 2005/0276804 | A1 | 12/2005 | Smith et al. | |
| 2007/0292438 | A1 | 12/2007 | Anderson et al. | |
| 2013/0072549 | A1 | 3/2013 | Stelzer | |

FOREIGN PATENT DOCUMENTS

| | | | | |
|---|---|---|---|---|
| DE | 102011018586 | | 10/2012 | |
| DE | 102011018586 | A1 * | 10/2012 | C07K 14/4716 |
| EP | 13164212.6 | | 4/2013 | |
| EP | 13198201.9 | | 12/2013 | |
| WO | 96/37626 | | 11/1996 | |
| WO | WO2002081632 | * | 10/2002 | |
| WO | 2008093323 | | 8/2008 | |
| WO | WO-2008093323 | A2 * | 8/2008 | C07K 14/47 |

(Continued)

OTHER PUBLICATIONS

Galinska-Rakoczy et al. (2008, J. Mol. Biol., vol. 379, pp. 929-935) (Year: 2008).*

(Continued)

*Primary Examiner* — Anoop K Singh
*Assistant Examiner* — David A Montanari
(74) *Attorney, Agent, or Firm* — RinLaures LLC; Li-Hsien Rin-Laures; Kristen A. Dola

(57) ABSTRACT

The present invention relates to a gene therapy vector which is useful in the treatment or prevention of hypertrophic cardiomyopathy in a subject in need thereof. The gene therapy vector of the invention comprises a nucleic acid sequence encoding a cardiac sarcomeric protein and a cardiomyocyte-specific promoter which is operably linked to said nucleic acid sequence. The invention furthermore relates to a cell which comprises the gene therapy vector. Pharmaceutical compositions which comprise the gene therapy vector and/or a cell comprising said vector are also provided. In another aspect, the invention relates to a method for treating or preventing hypertrophic cardiomyopathy in a subject by introducing the gene therapy vector of the invention into a subject in need of treatment.

15 Claims, 8 Drawing Sheets

Specification includes a Sequence Listing.

(56) References Cited

FOREIGN PATENT DOCUMENTS

| WO | 2012/162705 | 11/2012 |
|---|---|---|
| WO | 2013/009825 | 1/2013 |
| WO | 2014170470 | 10/2014 |

OTHER PUBLICATIONS

Carrier et al. (1997, Circulation Res., vol. 80(3), pp. 427-434) (Year: 1997).*
Wu et al. (2008, Mol. Therapy, vol. 16(2), pp. 280-289). (Year: 2008).*
Veldwijk et al.: "Development and Optimization of a Real-Time Quantitative PCR-Based Method for the Titration of AAV-2 Vector Stocks" Mol Therapy vol. 6, 2002, pp. 272-278 (7 pages).
Laugwitz et al.: "Postnatal isl1+ cardioblasts enter fully differentiated cardiomyocyte lineages" Nature vol. 433, 2005, pp. 647-653 (8 pages).
Moretti et al.: "Multipotent Embryonic Isl1+ Progenitor Cells Lead to Cardiac, Smooth Muscle, and Endothelial Cell Diversification" Cell vol. 127, 2006, pp. 1151-1165 (15 pages).
Hansen et al.: "Development of a Drug Screening Platform Based on Engineered Heart Tissue" Circ Res vol. 107, 2010, pp. 35-44 (10 pages).
Stoehr et al.: "Contractile abnormalities and altered drug response in engineered heart tissue from Mybpc3-targeted knock-in mice" J Mol Cell Cardiol vol. 63, 2013, pp. 189-198 (10 pages).
Vandenburgh et al.: "Drug-screening platform based on the contractility of tissue-engineered muscle" Muscle Nerve vol. 37, 2008, pp. 438-447 (10 pages).
Sands: "Percutaneous intravenous injection in neonatal mice" Lab Anim Sci vol. 49, 1999, pp. 328-330 (3 pages).
Yang L et al.: "Human caradiovascular progenitor cells develop from a KDR+ embryonic-stem-cell-derived population" Nature vol. 22, 2008, pp. 524-8 (6 pages).
Flavigny J et al.: "COOH-terminal Truncated Cardiac Myosin-binding Protein C Mutants Resulting from Familial Hypertrophic Cardiomyopathy Mutations Exhibit Altered Expression and/or Incorporation in Fetal Rat Cardiomyocytes" J Mol Biol vol. 294, 1999, pp. 443-456 (14 pages).
Sarikas et al.: "Impairment of the ubiquitin-proteasome system by truncated cardiac myosin binding protein C mutants" Cardiovasc Res vol. 66, 2005, pp. 33-44 (12 pages).
He T et al.: "A simplified system for generating recombinant adenoviruses" Proc Natl Acad Sci U S A vol. 95, 1998, pp. 2509-2514 6 (6 pages).
International Search Report and Written Opinion dated Jul. 11, 2014 in Corresponding PCT/EP2014/057984 (13 pages).
Extended Search Report dated Mar. 25, 2014 in Corresponding EP 13 19 8201 (8 pages).
International Preliminary Report on Patentability dated Oct. 20, 2015 in Corresponding PCT/EP2014/057984 (7 pages).
Van Dijk et al.: "Contractile Dysfunction Irrespective of the Mutant Protein in Human Hypertrophic Cardiomyopathy With Normal Systolic Function" Circ Heart Fail vol. 5, 2012, pp. 36-46 (17 pages).
Office Action in corresponding U.S. Appl. No. 14/785,188, dated Jun. 2, 2017.
Office Action in corresponding U.S. Appl. No. 14/785,188, dated Dec. 28, 2017.
Office Action in corresponding U.S. Appl. No. 14/785,188, dated Nov. 21, 2018.
Siedman, et al., 2011, Circ. Res., vol. 108(6), pp. 1-15.
Marian AJ (2010, Eur. J. Clin. Invest., vol. 40(4), pp. 360-369.
Kotterman et al. (2014, Nature Genetics, vol. 15, pp. 445-451).
Chamberlain et al. (2017, Current Opinion in Cardiology, vol. 32(3), pp. 275-282).
Hannah-Shmouni et al. (2015, Canadian J. Cardiology, vol. 31, pp. 1338-1350).
Chute JP, Current Opin. Hematology, vol. 13, pp. 399-406.
Li et al. (2010, J. Cerebral Blood Flow and Metabolism, vol. 30, pp. 653-662).
Parr et al. (2007, Bone Marrow Transplant, vol. 40, pp. 609-619).
Dong, et al., "Characterization of Genome Integrity for Oversized Recombinant AAV Vector," Molecular Therapy, Jan. 2010, vol. 18, issue 1, pp. 87-92.
Search Report in related European Patent Application No. 14719704.0-1410, dated Oct. 25, 2016, 5 pages.
Office Action in corresponding Canadian Patent Application Serial No. 2,944,186, dated Aug. 14, 2018.
Khajetoorians et al.: "Replacement of Mybpc3 Mutation by 5'-trans-splicing in a Knockin Mouse Model: A Step Towards Causal Therapy of Hypertrophic Cardiomyopathy", Circulation Research vol. 111, No. 12, Dec. 7, 2012, e2 (9 pages).
Prasad et al: "Robust cardiomyocyte-specific gene expression following systemic injection of AAV: in vivo gene delivery follows a Poisson distribution", Gene Therapy, vol. 18, No. 1, Aug. 12, 2010 (Aug. 12, 2010), pp. 43-52 (10 pages).
Mearini, Giulia et al: "Repair of Mybpc3 mRNA by 5'-trans-splicing in a Mouse Model of Hypertrophic Cardiomyopathy", Molecular Therapy-Nucleic Acids, vol. 2, No. 7, Jul. 2, 2013 (Jul. 2, 2013), p. e102 (10 pages).
Ralph Knoell: "Myosin binding protein C: implications for signal-transduction", Journal of Muscle Research and Cell Motility, Kluwer Academic Publishers, DO, vol. 33, No. 1, Dec. 16, 2011 (Dec. 16, 2011), pp. 31-42 (12 pages).
Elliott et al.: "Classification of the cardiomyopathies: a position statement from the european society of cardiology working group on myocardial and pericardial diseases" Eur Heart J vol. 29, 2008, pp. 270-276 (7 pages).
Gersch et al.: "2011 ACCF/AHA guidelines for the diagnosis and treatment of hypertrophic cardiomyopathy" J Thorac Cardiovasc Surg vol. 142, 2011, pp. E153-E203 (51 pages).
Maron et al.: "Prevalence of Hypertrophic Cardiomyopathy in a General Population of Young Adults" Circulation vol. 92, 1995, pp. 785-789 (17 pages).
Carrier et al.: "The ubiquitin-proteasome system and nonsensemediated mRNA decay in hypertrophic cardiomyopathy" Cardiovasc Res vol. 85, 2010, pp. 330-338 (9 pages).
Schlossarek et al.: "Cardiac myosin-binding protein C in hypertrophic cardiomyopathy: Mechanisms and therapeutic opportunities" J Mol Cell Cardiol vol. 50, 2011, pp. 613-620 (8 pages).
Richard et al.: "Hypertrophic Cardiomyopathy Distribution of Disease Genes, Spectrum of Mutations, and Implications for a Molecular Diagnosis Strategy" Circulation vol. 107, 2003, pp. 2227-2232 (10 pages).
Friedrich et al.: "Evidence for FHL1 as a novel disease gene for isolated hypertrophic cardiomyopathy" Hum Mol Genet vol. 21, 2012, pp. 3237-3254 (18 pages).
Bonne et al.: "Cardiac myosin binding protein-C gene splice acceptor site mutation is associated with familial hypertrophic cardiomyopathy" Nature Genet vol. 11, 1995, pp. 438-440 (3 pages).
Watkins et al.: "Inherited cardiomyopathies" N Engl J Med. vol. 364, 2011, pp. 1643-1656 (14 pages).
Fougerousse et al.: "Cardiac Myosin Binding Protein C Gene is Specifically Expressed in Heart During Murine and Human Development" Circ Res vol. 82, 1998, pp. 130-133 (5 pages).
Pohlmann et al.: "Cardiac Myosin-Binding Protein C is Required for Complete Relaxation in Intact Myocytes" Circ Res vol. 101, 2007, pp. 928-3 (19 pages).
Carrier et al.: "Organization and Sequence of Human Cardiac Myosin Binding Protein C Gene (MYBPC3) and Identification of Mutations Predicted to Produce Truncated Proteins in Familial Hypertrophic Cardiomyopathy" Circ Res vol. 80, 1997, pp. 427-434 (8 pages).
Marston et al.: "Evidence From Human Myectomy Samples That MYBPC3 Mutations Cause Hypertrophic Cardiomyopathy Through Haploinsufficiency" Circ Res vol. 105, 2009, pp. 219-222 (15 pages).
Van Dijk et al.: "Cardiac Myosin-Binding Protein C Mutations and Hypertrophic Cardiomyopathy" Circulation vol. 119, 2009, pp. 1473-1483 (12 pages).

(56) References Cited

OTHER PUBLICATIONS

Meurs et al.: "A cardiac myosin binding protein C mutation in the Maine Coon cat with familial hypertrophic cardiomyopathy" Hum Mol Genet vol. 14, 2005, pp. 3587-3593 (7 pages).
Vignier et al.: "Nonsense-Mediated mRNA Decay and Ubiquitin-Proteasome System Regulate Cardiac Myosin-Binding Protein C Mutant Levels in Cardiomyopathic Mice" Circ Res vol. 105, 2009, pp. 239-248 (10 pages).
Jessup et al.: "Calcium Upregulation by Percutaneous Administration of Gene Therapy in Cardiac Disease (CUPID)" Circulation vol. 124, 2011, pp. 304-313 (40 pages).
Merkulov et al.: "In Vivo Cardiac Myosin Binding Protein C Gene Transfer Rescues Myofilament Contractile Dysfunction in Cardiac Myosin Binding Protein C Null Mice" Circ Heart Fail vol. 5, 2012, pp. 635-644 (22 pages).
Schlossarek et al.: "Defective proteolytic systems in Mybpc3-targeted mice with cardiac hypertrophy" Basic Res Cardiol vol. 107, 2012, pp. 1-13 (13 pages).
Schlossarek et al.: "Adrenergic stress reveals septal hypertrophy and proteasome impairment in heterozygous Mybpc3-targeted knock-in mice" J Muscle Res Cell Motil vol. 33, 2012, pp. 5-15 (11 pages).
Sadayappan et al.: "Cardiac Myosin-Binding Protein-C Phosphorylation and Cardiac Function" Circ Res vol. 97, 2005, pp. 1156-1163 (26 pages).
Sadayappan et al.: "Cardiac myosin binding protein c phosphorylation is cardioprotective" Proc Natl Acad Sci U S A vol. 103, 2006, pp. 16918-16923 (6 pages).
Gorman et al.: "The Rous sarcoma virus long terminal repeat is a strong promoter when introduced into a variety of eukaryotic cells by DNA-mediated transfection" Proc. Natl. Acad. Sci. vol. 79, 1982, p. 6777 (5 pages).
Geisler et al.: "microRNA122-regulated transgene expression increases specificity of cardiac gene transfer upon intravenous delivery of AAV9 vectors" Gene Therapy vol. 18, 2011, pp. 199-209 (11 pages).
Dominguez et al.: "Intravenous scAAV9 delivery of a codon-optimized SMN1 sequence rescues SMA mice" Hum Mol Genet vol. 20, 2011, pp. 681-693 (13 pages).
Wu et al.: "Adeno-associated Virus Serotypes: Vector Toolkit for Human Gene Therapy" Mol Therapy vol. 14, 2006, pp. 316-327 (12 pages).
Bowles et al.: "Phase 1 Gene Therapy for Duchenne Muscular Dystrophy Using a Translational Optimized AAV Vector" Mol Therapy vol. 20, 2012, pp. 443-455 (13 pages).
Wu et al.: "Effect of Genome Size on AAV Vector Packaging" Mol Therapy vol. 18, 2010, pp. 80-86 (7 pages).
Katz et al.: "Gene delivery technologies for cardiac applications" Gene Therapy vol. 19, 2012, pp. 659-669 (24 pages).
Jaski et al.: "Calcium Upregulation by Percutaneous Administration of Gene Therapy in Cardiac Disease (CUPID Trial), a First-in-Human Phase 1/2 Clinical Trial" J Card Fail vol. 15, 2009, pp. 171-181 (11 pages).
Gao et al.: "Transendocardial Delivery of AAV6 Results in Highly Efficient and Global Cardiac Gene Transfer in Rhesus Macaques" Human Gene Therapy vol. 22, 2011, pp. 979-984 (7 pages).
Okita et al.: "Generation of germline-competent induced pluripotent stem cells" Nature vol. 448, 2007, pp. 313-7 (6 pages).
Yu et al.: "Induced Pluripotent Stem Cell Lines Derived from Human Somatic Cells" Science vol. 318, 2007, pp. 1917-1920 (4 pages).
Maekawa et al.: "Direct reprogramming of somatic cells is promoted by maternal transcription factor Glis1" Nature vol. 474, 2011, pp. 225-229 (6 pages).
Aasen et al.: "Efficient and rapid generation of induced pluripotent stem cells from human keratinocytes" Nat Biotech vol. 11, 2008, pp. 1276-1284 (9 pages).
Aasen et al.: "Isolation and cultivation of human keratinocytes from skin or plucked hair for the generation of induced pluripotent stem cells" Nat Protocol vol. 5, 2010, pp. 371-382 (12 pages).
Staerk et al.: "Reprogramming of Human Peripheral Blood Cells to Induced Pluripotent Stem Cells" Cell Stem Cell vol. 7, 2010, pp. 20-24 (5 pages).
Seki et al.: "Generation of induced pluripotent stem cells from a small amount of human peropheral blood using a combination of activated T cells and Sendai virus" Nat Protocol vol. 7, 2012, pp. 718-728 (11 pages).
Muller et al.: "Improved cardiac gene transfer by transcriptional and transductional targeting of adeno-associated viral vectors" Cardiovasc Res vol. 70, 2006, pp. 70-78 (9 pages).
Kaya et al.: "Comparison of IL-10 and MCP-1-7ND gene transfer with AAV9 vectors for protection from murine autoimmune myocarditis" Cardiovasc Res vol. 91, 2011, pp. 116-123 (8 pages).
Grimm et al.: "Helper Virus-Free, Optically Controllable, and Two-Plasmid-Based Production of Adeno-associated Virus Vectors of Serotypes 1 to 6" Mol Therapy vol. 7, 2003, pp. 839-850 (12 pages).
Grieger et al.: "Production and characterization of adeno-associated viral vectors" Nat Protoc vol. 1, 2006, pp. 1412-1428 (17 pages).
Hauswirth et al.: "Production and purification of recombinant adeno-associated virus" Methods Enzymol vol. 316, 2000, pp. 743-761 (19 pages).

* cited by examiner

A

B

C

A

B

C

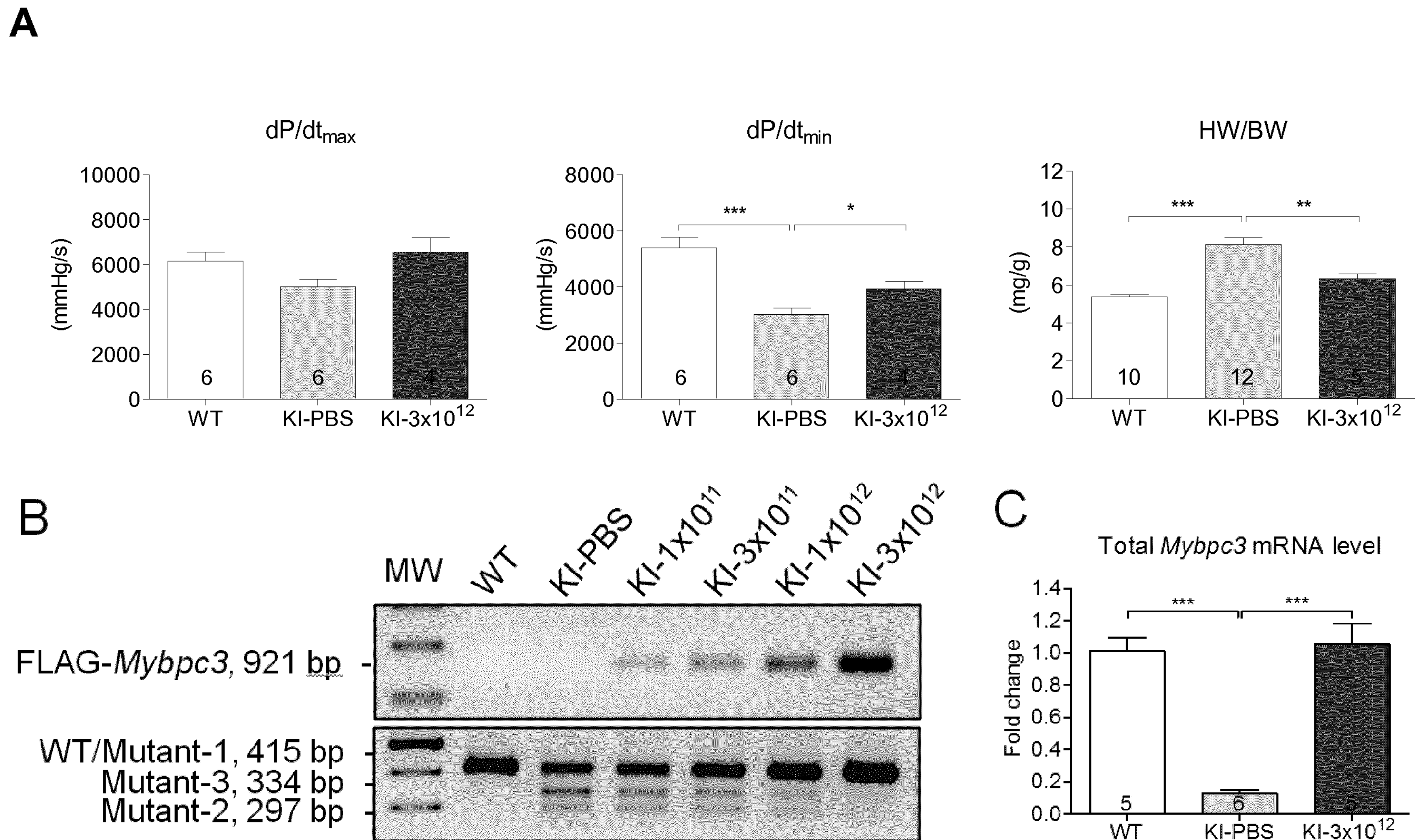
Figure 7.1

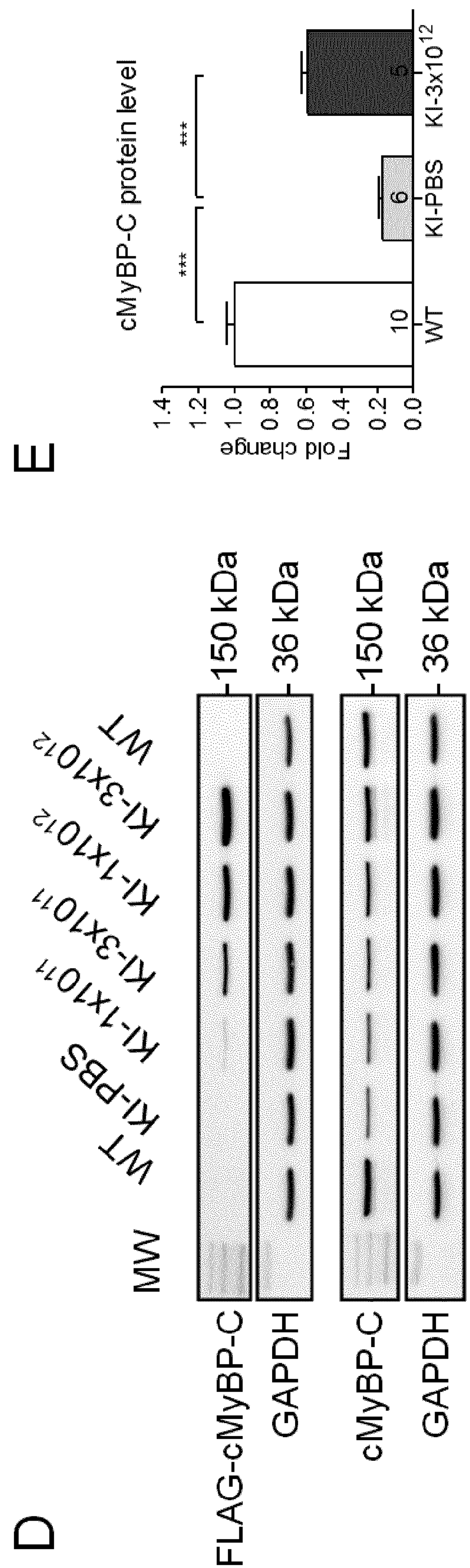
Figure 7.2

SEQUENCE LISTING

```
<160> NUMBER OF SEQ ID NOS: 35

<210> SEQ ID NO 1
<211> LENGTH: 4200
<212> TYPE: DNA
<213> ORGANISM: Homo sapiens

<400> SEQUENCE: 1

catggtgagt gcctggtgtg acgtctctca ggatgcctga gccggggaag aagccagtct      60

cagcctttag caagaagcca cggtcagtgg aagtggccgc aggcagccct gccgtgttcg     120

aggccgagac agagcgggca ggagtgaagg tgcgctggca gcgcggaggc agtgacatca     180

gcgccagcaa caagtacggc ctggccacag agggcacacg gcatacgctg acagtgcggg     240

aagtgggccc tgccgaccag ggatcttacg cagtcattgc tggctcctcc aaggtcaagt     300

tcgacctcaa ggtcatagag gcagagaagg cagagcccat gctggcccct gcccctgccc     360

ctgctgaggc cactggagcc cctggagaag ccccggcccc agccgctgag ctgggagaaa     420

gtgccccaag tcccaaaggg tcaagctcag cagctctcaa tggtcctacc cctggagccc     480

ccgatgaccc cattggcctc ttcgtgatgc ggccacagga tggcgaggtg accgtgggtg     540

gcagcatcac cttctcagcc cgcgtggccg gcgccagcct cctgaagccg cctgtggtca     600

agtggttcaa gggcaaatgg gtggacctga gcagcaaggt gggccagcac ctgcagctgc     660

acgacagcta cgaccgcgcc agcaaggtct atctgttcga gctgcacatc accgatgccc     720

agcctgcctt cactggcagc taccgctgtg aggtgtccac caaggacaaa tttgaatgct     780
```

-continued

```
ccaacttcaa tctcactgtc cacgaggcca tgggcaccgg agacctggac ctcctatcag    840
ccttccgccg cacgagcctg gctggaggtg gtcggcggat cagtgatagc catgaggaca    900
ctgggattct ggacttcagc tcactgctga aaaagagaga cagtttccgg accccgaggg    960
actcgaagct ggaggcacca gcagaggagg acgtgtggga gatcctacgg caggcacccc   1020
catctgagta cgagcgcatc gccttccagt acggcgtcac tgacctgcgc ggcatgctaa   1080
agaggctcaa gggcatgagg cgcgatgaga agaagagcac agcctttcag aagaagctgg   1140
agccggccta ccaggtgagc aaaggccaca agatccggct gaccgtggaa ctggctgacc   1200
atgacgctga ggtcaaatgg ctcaagaatg gccaggagat ccagatgagc ggcagcaagt   1260
acatctttga gtccatcggt gccaagcgta ccctgaccat cagccagtgc tcattggcgg   1320
acgacgcagc ctaccagtgc gtggtgggtg gcgagaagtg tagcacggag ctctttgtga   1380
aagagccccc tgtgctcatc acgcgcccct tggaggacca gctggtgatg gtggggcagc   1440
gggtggagtt tgagtgtgaa gtatcggagg agggggcgca agtcaaatgg ctgaaggacg   1500
gggtggagct gacccgggag gagaccttca aataccggtt caagaaggac gggcagagac   1560
accacctgat catcaacgag gccatgctgg aggacgcggg gcactatgca ctgtgcacta   1620
gcgggggcca ggcgctgcgt gagctcattg tgcaggaaaa gaagctggag gtgtaccaga   1680
gcatcgcaga cctgatggtg ggcgcaaagg accaggcggt gttcaaatgt gaggtctcag   1740
atgagaatgt tcggggtgtg tggctgaaga atgggaagga gctggtgccc gacagccgca   1800
taaaggtgtc ccacatcggg cgggtccaca aactgaccat tgacgacgtc acacctgccg   1860
acgaggctga ctacagcttt gtgcccgagg gcttcgcctg caacctgtca gccaagctcc   1920
acttcatgga ggtcaagatt gacttcgtac ccaggcagga acctcccaag atccacctgg   1980
actgcccagg ccgcatacca gacaccattg tggttgtagc tggaaataag ctacgtctgg   2040
acgtccctat ctctggggac cctgctccca ctgtgatctg gcagaaggct atcacgcagg   2100
ggaataaggc cccagccagg ccagccccag atgccccaga ggacacaggt gacagcgatg   2160
agtgggtgtt tgacaagaag ctgctgtgtg agaccgaggg ccgggtccgc gtggagacca   2220
ccaaggaccg cagcatcttc acggtcgagg gggcagagaa ggaagatgag ggcgtctaca   2280
cggtcacagt gaagaaccct gtgggcgagg accaggtcaa cctcacagtc aaggtcatcg   2340
acgtgccaga cgcacctgcg gcccccaaga tcagcaacgt gggagaggac tcctgcacag   2400
tacagtggga gccgcctgcc tacgatggcg ggcagcccat cctgggctac atcctggagc   2460
gcaagaagaa gaagagctac cggtggatgc agctgaactt cgacctgatt caggagctga   2520
gtcatgaagc gcggcgcatg atcgagggcg tggtgtacga gatgcgcgtc tacgcggtca   2580
acgccatcgg catgtccagg cccagccctg cctcccagcc cttcatgcct atcggtcccc   2640
ccagcgaacc cacccacctg gcagtagagg acgtctctga caccacggtc tccctcaagt   2700
ggcggccccc agagcgcgtg ggagcaggag gcctggatgg ctacagcgtg gagtactgcc   2760
cagagggctg ctcagagtgg gtggctgccc tgcaggggct gacagagcac acatcgatac   2820
tggtgaagga cctgcccacg gggggcccggc tgcttttccg agtgcgggca cacaatatgg   2880
cagggcctgg agcccctgtt accaccacgg agccggtgac agtgcaggag atcctgcaac   2940
ggccacggct tcagctgccc aggcacctgc gccagaccat tcagaagaag gtcggggagc   3000
ctgtgaacct tctcatccct ttccagggca agccccggcc tcaggtgacc tggaccaaag   3060
aggggcagcc cctggcaggc gaggaggtga gcatccgcaa cagccccaca gacaccatcc   3120
tgttcatccg ggccgctcgc cgcgtgcatt caggcactta ccaggtgacg gtgcgcattg   3180
```

```
agaacatgga ggacaaggcc acgctggtgc tgcaggttgt tgacaagcca agtcctcccc   3240

aggatctccg ggtgactgac gcctggggtc ttaatgtggc tctggagtgg aagccacccc   3300

aggatgtcgg caacacggaa ctctggggt acacagtgca gaaagccgac aagaagacca    3360

tggagtggtt caccgtcttg gagcattacc gccgcaccca ctgcgtggtg ccagagctca   3420

tcattggcaa tggctactac ttccgcgtct tcagccagaa tatggttggc tttagtgaca   3480

gagcggccac caccaaggag cccgtcttta tccccagacc aggcatcacc tatgagccac   3540

ccaactataa ggccctggac ttctccgagg ccccaagctt cacccagccc ctggtgaacc   3600

gctcggtcat cgcgggctac actgctatgc tctgctgtgc tgtccggggt agccccaagc   3660

ccaagatttc ctggttcaag aatggcctgg acctgggaga agacgcccgc ttccgcatgt   3720

tcagcaagca gggagtgttg actctggaga ttagaaagcc ctgcccctt gacgggggca    3780

tctatgtctg cagggccacc aacttacagg gcgaggcacg gtgtgagtgc cgcctggagg   3840

tgcgagtgcc tcagtgacca ggctggctcc tggggatggc caggtacaac cggatgccag   3900

ccccgtgcca ggagcctgga gggaagttgg ggaaacccct ccctactgtt ggatgtatgt   3960

gtgacaagtg tgtctcctgt gctgcgatgg gggatcagca gggcagttgt cgggcagtcc   4020

tgagtgggtg ttgcacagac tggtccacag ggctcctgaa ggaagcccct ggatctttgg   4080

ggtaaaagga gggtggcctc aagaaacaat gtctggggac aggcctttct ggcctgctat   4140

gtcttcccaa tgtttattgg gcaataaaag ataagtgcag tcacagagaa ctcactcttc   4200
```

```
<210> SEQ ID NO 2
<211> LENGTH: 1274
<212> TYPE: PRT
<213> ORGANISM: Homo sapiens

<400> SEQUENCE: 2

Met Pro Glu Pro Gly Lys Lys Pro Val Ser Ala Phe Ser Lys Lys Pro
1               5                   10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Thr Val Arg Glu Val Gly Pro Ala Asp Gln Gly Ser Tyr Ala
65                  70                  75                  80

Val Ile Ala Gly Ser Ser Lys Val Lys Phe Asp Leu Lys Val Ile Glu
                85                  90                  95

Ala Glu Lys Ala Glu Pro Met Leu Ala Pro Ala Pro Ala Pro Ala Glu
            100                 105                 110

Ala Thr Gly Ala Pro Gly Glu Ala Pro Ala Pro Ala Ala Glu Leu Gly
        115                 120                 125

Glu Ser Ala Pro Ser Pro Lys Gly Ser Ser Ser Ala Ala Leu Asn Gly
    130                 135                 140

Pro Thr Pro Gly Ala Pro Asp Asp Pro Ile Gly Leu Phe Val Met Arg
145                 150                 155                 160

Pro Gln Asp Gly Glu Val Thr Val Gly Gly Ser Ile Thr Phe Ser Ala
                165                 170                 175

Arg Val Ala Gly Ala Ser Leu Leu Lys Pro Pro Val Val Lys Trp Phe
            180                 185                 190
```

```
Lys Gly Lys Trp Val Asp Leu Ser Ser Lys Val Gly Gln His Leu Gln
        195                 200                 205

Leu His Asp Ser Tyr Asp Arg Ala Ser Lys Val Tyr Leu Phe Glu Leu
    210                 215                 220

His Ile Thr Asp Ala Gln Pro Ala Phe Thr Gly Ser Tyr Arg Cys Glu
225                 230                 235                 240

Val Ser Thr Lys Asp Lys Phe Asp Cys Ser Asn Phe Asn Leu Thr Val
                245                 250                 255

His Glu Ala Met Gly Thr Gly Asp Leu Asp Leu Leu Ser Ala Phe Arg
            260                 265                 270

Arg Thr Ser Leu Ala Gly Gly Gly Arg Arg Ile Ser Asp Ser His Glu
        275                 280                 285

Asp Thr Gly Ile Leu Asp Phe Ser Ser Leu Leu Lys Lys Arg Asp Ser
    290                 295                 300

Phe Arg Thr Pro Arg Asp Ser Lys Leu Glu Ala Pro Ala Glu Glu Asp
305                 310                 315                 320

Val Trp Glu Ile Leu Arg Gln Ala Pro Pro Ser Glu Tyr Glu Arg Ile
                325                 330                 335

Ala Phe Gln Tyr Gly Val Thr Asp Leu Arg Gly Met Leu Lys Arg Leu
            340                 345                 350

Lys Gly Met Arg Arg Asp Glu Lys Lys Ser Thr Ala Phe Gln Lys Lys
        355                 360                 365

Leu Glu Pro Ala Tyr Gln Val Ser Lys Gly His Lys Ile Arg Leu Thr
    370                 375                 380

Val Glu Leu Ala Asp His Asp Ala Glu Val Lys Trp Leu Lys Asn Gly
385                 390                 395                 400

Gln Glu Ile Gln Met Ser Gly Ser Lys Tyr Ile Phe Glu Ser Ile Gly
                405                 410                 415

Ala Lys Arg Thr Leu Thr Ile Ser Gln Cys Ser Leu Ala Asp Asp Ala
            420                 425                 430

Ala Tyr Gln Cys Val Val Gly Gly Glu Lys Cys Ser Thr Glu Leu Phe
        435                 440                 445

Val Lys Glu Pro Pro Val Leu Ile Thr Arg Pro Leu Glu Asp Gln Leu
    450                 455                 460

Val Met Val Gly Gln Arg Val Glu Phe Glu Cys Glu Val Ser Glu Glu
465                 470                 475                 480

Gly Ala Gln Val Lys Trp Leu Lys Asp Gly Val Glu Leu Thr Arg Glu
                485                 490                 495

Glu Thr Phe Lys Tyr Arg Phe Lys Lys Asp Gly Gln Arg His His Leu
            500                 505                 510

Ile Ile Asn Glu Ala Met Leu Glu Asp Ala Gly His Tyr Ala Leu Cys
        515                 520                 525

Thr Ser Gly Gly Gln Ala Leu Ala Glu Leu Ile Val Gln Glu Lys Lys
    530                 535                 540

Leu Glu Val Tyr Gln Ser Ile Ala Asp Leu Met Val Gly Ala Lys Asp
545                 550                 555                 560

Gln Ala Val Phe Lys Cys Glu Val Ser Asp Glu Asn Val Arg Gly Val
                565                 570                 575

Trp Leu Lys Asn Gly Lys Glu Leu Val Pro Asp Ser Arg Ile Lys Val
            580                 585                 590

Ser His Ile Gly Arg Val His Lys Leu Thr Ile Asp Asp Val Thr Pro
        595                 600                 605

Ala Asp Glu Ala Asp Tyr Ser Phe Val Pro Glu Gly Phe Ala Cys Asn
```

```
    610                 615                 620

Leu Ser Ala Lys Leu His Phe Met Glu Val Lys Ile Asp Phe Val Pro
625                 630                 635                 640

Arg Gln Glu Pro Pro Lys Ile His Leu Asp Cys Pro Gly Arg Ile Pro
                645                 650                 655

Asp Thr Ile Val Val Val Ala Gly Asn Lys Leu Arg Leu Asp Val Pro
            660                 665                 670

Ile Ser Gly Asp Pro Ala Pro Thr Val Ile Trp Gln Lys Ala Ile Thr
        675                 680                 685

Gln Gly Asn Lys Ala Pro Ala Arg Pro Ala Pro Asp Ala Pro Glu Asp
    690                 695                 700

Thr Gly Asp Ser Asp Glu Trp Val Phe Asp Lys Lys Leu Leu Cys Glu
705                 710                 715                 720

Thr Glu Gly Arg Val Arg Val Glu Thr Thr Lys Asp Arg Ser Ile Phe
                725                 730                 735

Thr Val Glu Gly Ala Glu Lys Glu Asp Glu Gly Val Tyr Thr Val Thr
            740                 745                 750

Val Lys Asn Pro Val Gly Glu Asp Gln Val Asn Leu Thr Val Lys Val
        755                 760                 765

Ile Asp Val Pro Asp Ala Pro Ala Ala Pro Lys Ile Ser Asn Val Gly
    770                 775                 780

Glu Asp Ser Cys Thr Val Gln Trp Glu Pro Pro Ala Tyr Asp Gly Gly
785                 790                 795                 800

Gln Pro Ile Leu Gly Tyr Ile Leu Glu Arg Lys Lys Lys Lys Ser Tyr
                805                 810                 815

Arg Trp Met Arg Leu Asn Phe Asp Leu Ile Gln Glu Leu Ser His Glu
            820                 825                 830

Ala Arg Arg Met Ile Glu Gly Val Val Tyr Glu Met Arg Val Tyr Ala
        835                 840                 845

Val Asn Ala Ile Gly Met Ser Arg Pro Ser Pro Ala Ser Gln Pro Phe
    850                 855                 860

Met Pro Ile Gly Pro Pro Ser Glu Pro Thr His Leu Ala Val Glu Asp
865                 870                 875                 880

Val Ser Asp Thr Thr Val Ser Leu Lys Trp Arg Pro Pro Glu Arg Val
                885                 890                 895

Gly Ala Gly Gly Leu Asp Gly Tyr Ser Val Glu Tyr Cys Pro Glu Gly
            900                 905                 910

Cys Ser Glu Trp Val Ala Ala Leu Gln Gly Leu Thr Glu His Thr Ser
        915                 920                 925

Ile Leu Val Lys Asp Leu Pro Thr Gly Ala Arg Leu Leu Phe Arg Val
    930                 935                 940

Arg Ala His Asn Met Ala Gly Pro Gly Ala Pro Val Thr Thr Thr Glu
945                 950                 955                 960

Pro Val Thr Val Gln Glu Ile Leu Gln Arg Pro Arg Leu Gln Leu Pro
                965                 970                 975

Arg His Leu Arg Gln Thr Ile Gln Lys Lys Val Gly Glu Pro Val Asn
            980                 985                 990

Leu Leu Ile Pro Phe Gln Gly Lys  Pro Arg Pro Gln Val  Thr Trp Thr
        995                 1000                1005

Lys Glu  Gly Gln Pro Leu Ala  Gly Glu Glu Val Ser  Ile Arg Asn
    1010                 1015                1020

Ser Pro  Thr Asp Thr Ile Leu  Phe Ile Arg Ala Ala  Arg Arg Val
    1025                 1030                1035
```

```
His Ser  Gly Thr Tyr Gln Val  Thr Val Arg Ile Glu  Asn Met Glu
    1040                 1045                 1050

Asp Lys  Ala Thr Leu Val Leu  Gln Val Val Asp Lys  Pro Ser Pro
    1055                 1060                 1065

Pro Gln  Asp Leu Arg Val Thr  Asp Ala Trp Gly Leu  Asn Val Ala
    1070                 1075                 1080

Leu Glu  Trp Lys Pro Pro Gln  Asp Val Gly Asn Thr  Glu Leu Trp
    1085                 1090                 1095

Gly Tyr  Thr Val Gln Lys Ala  Asp Lys Lys Thr Met  Glu Trp Phe
    1100                 1105                 1110

Thr Val  Leu Glu His Tyr Arg  Arg Thr His Cys Val  Val Pro Glu
    1115                 1120                 1125

Leu Ile  Ile Gly Asn Gly Tyr  Tyr Phe Arg Val Phe  Ser Gln Asn
    1130                 1135                 1140

Met Val  Gly Phe Ser Asp Arg  Ala Ala Thr Thr Lys  Glu Pro Val
    1145                 1150                 1155

Phe Ile  Pro Arg Pro Gly Ile  Thr Tyr Glu Pro Pro  Asn Tyr Lys
    1160                 1165                 1170

Ala Leu  Asp Phe Ser Glu Ala  Pro Ser Phe Thr Gln  Pro Leu Val
    1175                 1180                 1185

Asn Arg  Ser Val Ile Ala Gly  Tyr Thr Ala Met Leu  Cys Cys Ala
    1190                 1195                 1200

Val Arg  Gly Ser Pro Lys Pro  Lys Ile Ser Trp Phe  Lys Asn Gly
    1205                 1210                 1215

Leu Asp  Leu Gly Glu Asp Ala  Arg Phe Arg Met Phe  Ser Lys Gln
    1220                 1225                 1230

Gly Val  Leu Thr Leu Glu Ile  Arg Lys Pro Cys Pro  Phe Asp Gly
    1235                 1240                 1245

Gly Ile  Tyr Val Cys Arg Ala  Thr Asn Leu Gln Gly  Glu Ala Arg
    1250                 1255                 1260

Cys Glu  Cys Arg Leu Glu Val  Arg Val Pro Gln
    1265                 1270
```

<210> SEQ ID NO 3
<211> LENGTH: 4163
<212> TYPE: DNA
<213> ORGANISM: Mus musculus

<400> SEQUENCE: 3

```
agtccctcct tgggtggcct gcttgatgcc tggtgtgact gttctcaaga tgccggagcc     60

agggaagaaa ccagtgtcag ccttcaacaa gaagccaagg tcagcggagg tgaccgctgg    120

cagtgctgcc gtgttcgagg ctgagacgga gcggtcaggc gtgaaggtgc ggtggcagcg    180

ggatggcagc gacatcaccg ccaatgacaa gtatggtttg gcagcagagg gcaagcgaca    240

cacactgaca gtgcgggatg cgagccctga tgaccagggt tcctacgcgg tcattgcagg    300

ctcctcaaag gtcaagtttg acctcaaggt cacagagcca gcccctccag agaaggcaga    360

atctgaagtt gctccaggag cccccaaaga agtccctgct ccagccactg agttggaaga    420

aagtgtctca agtcctgaag ggtcagtctc ggtaacccag gatggctcag ctgcagagca    480

tcagggagcc cctgatgacc ctattggcct ctttctgatg cgaccacagg atggtgaggt    540

gaccgtgggc ggcagcattg tcttctcagc ccgagtggct ggggccagcc tcctgaaacc    600

gcctgtggtc aagtggttca agggcaagtg ggtggacctg agcagcaaag tgggccagca    660
```

```
cctgcagctg catgacagct atgacagagc cagcaaggtc tacttgtttg agttgcacat    720
cacagatgct cagaccactt ctgctggggg ctaccgctgt gaggtgtcta ccaaggacaa    780
atttgacagc tgtaacttca acctcactgt ccatgaggcc attggttctg gagacctgga    840
cctcagatca gctttccgac gcacgagcct ggcgggagca ggtcggagaa ccagtgacag    900
ccatgaagat gctgggactc tggactttag ttccctgctg aagaagagag acagtttccg    960
gagggactca aagctggagg cacctgctga agaagacgtg tgggagatcc tgagacaggc   1020
accgccgtca gaatatgagc gcatcgcctt ccagcacgga gtcacagacc ttcgaggcat   1080
gctgaagagg ctcaagggca tgaagcagga tgaaaagaag agcacagcct ttcagaagaa   1140
gctggagcct gcctaccagg taaacaaggg ccacaagatt cggcttactg tggaactggc   1200
tgatccggac gccgaagtca agtggcttaa gaatggacag gagatccaga tgagtggcag   1260
caagtacatc ttcgagtccg tcggtgccaa gcgcaccctg accatcagcc agtgctcact   1320
ggctgacgac gcagcctacc agtgtgtggt ggggggcgag aagtgcagca cggagctctt   1380
tgtcaaagag cccccggtgc tgatcactcg gtccctggaa gaccagctgg tgatggtggg   1440
tcagcgggtg gagtttgagt gtgaggtctc agaagaaggg gcccaagtca aatggctgaa   1500
ggatggggtt gagctgacac gtgaggagac cttcaaatac cggttcaaga aagatgggcg   1560
gaaacaccac ttgatcatca atgaagcaac cctggaggat gcaggacact atgcagtacg   1620
cacaagtgga ggccagtcac tggctgagct cattgtgcaa gagaagaagt tggaggtata   1680
ccaaagcatc gcggacctgg cagtgggagc caaggaccag gctgtgttta agtgtgaggt   1740
ttcagatgag aatgtacgcg gcgtgtggct gaagaatggg aaggaactgg tgcctgacaa   1800
ccgcataaag gtgtcccata taggccgggt ccacaaactg accattgacg atgtcacacc   1860
tgctgatgag gctgactaca gctttgtccc tgaagggttt gcctgcaacc tgtctgccaa   1920
gctccacttc atggaggtca agattgactt tgtgcctagg caggaacctc ccaagatcca   1980
cttggattgt cccggcagca caccagacac cattgtggtt gttgctggga acaagttacg   2040
cctggatgtc cctatttctg gagaccctgc tcccactgtg gtctggcaga agactgtaac   2100
acaggggaag aaggcctcaa ctgggccaca ccctgatgcc ccagaagatg ctggtgctga   2160
tgaggagtgg gtgtttgata agaagctgtt gtgtgagact gagggccggg tccgggtgga   2220
gaccaccaaa gaccgcagcg tctttacagt cgaaggggca gagaaggaag atgaaggtgt   2280
ctacacagtc acagtaaaga accccgtggg cgaggaccag gtcaacctca cagtcaaggt   2340
catcgatgtc ccagatgctc ctgcggcccc taagatcagc aacgtgggcg aggactcctg   2400
cactgtgcag tgggaaccgc ctgcctatga tggcgggcag ccggtcctgg gatacatcct   2460
ggagcgcaag aagaaaaaga gctacaggtg gatgaggctc aactttgatc tgctgcggga   2520
gctgagccac gaggcgaggc gcatgatcga gggtgtagcc tatgagatgc gagtctacgc   2580
agtcaatgcc gtgggaatgt ccaggcccag ccctgcctct cagcccttca tgcctattgg   2640
gcccccctggc gaaccaaccc acttggctgt ggaggatgtg tcagacacca ctgtctcact   2700
caagtggcgg cccccagagc gcgtgggggc cggtggcctg gacggataca gcgtggagta   2760
ctgccaggag ggatgctccg agtggacacc tgctctgcag ggctgacag agcgcacatc   2820
gatgctggtg aaggacctac ccactggggc acggctgctg ttccgagtac gggcacacaa   2880
tgtggcaggt cctggaggcc ctatcgtcac caaggagcct gtgacagtgc aggagatact   2940
gcaacgacca cggctccaac tgcccagaca cctgcgccag accatccaga agaaagttgg   3000
ggagcctgtg aacctcctca tccctttcca gggcaaaccc cggcctcagg tgacctggac   3060
```

```
caaagagggg cagcccctgg caggtgagga ggtgagcatc cggaacagcc ccacagacac   3120

gatcttgttc atccgagctg cccgccgcac ccactcgggc acctaccagg tgacagttcg   3180

cattgagaac atggaggaca aggcaacgct gatcctgcag attgtggaca agccaagtcc   3240

tccccaggat atccggatcg ttgagacttg ggtttcaat gtggctctgg agtggaagcc    3300

accccaagat gatggcaata cagagatctg ggttatact gtacagaaag ctgacaagaa    3360

gaccatggag tggttcacgg ttttggaaca ctaccgacgc actcactgtg tggtatcaga   3420

gcttatcatt ggcaatggct actacttccg ggtcttcagc cataacatgg tgggttccag   3480

tgacaaagct gccgccacca aggagccagt ctttattcca agaccaggca tcacatatga   3540

gccacccaaa tacaaggccc tggacttctc tgaggcccca agcttcaccc agcccttggc   3600

aaatcgctcc atcattgcag gctataatgc catcctctgc tgtgctgtcc gaggtagtcc   3660

taagcccaag atttcctggt tcaagaatgg cctggatctg ggagaagatg ctcgcttccg   3720

catgttctgc aagcagggag tattgaccct ggagatcagg aaaccctgcc cctatgatgg   3780

tggtgtctat gtctgcaggg ccaccaactt gcagggcgag gcacagtgtg agtgccgcct   3840

ggaggtgcga gttcctcagt gaccaggatg gctccccaga gatggctagg tacaaatgga   3900

tgccaggctg tgtaccagac cggaagggag ttggaggagc accctttttct gctactgcat  3960

gtgtgtgtgc aactgtgcat cctggaagga ctggccagca gtgacaccag gcaggtctgc   4020

tgggttctga agaaactgac cctaaggata atgttaatac tgggagcata aagtgtgtgg   4080

gcttcagaag tggtgactgg ggacaggccc ttttggctgg ctcattgtgt aggagcaata   4140

aaagatctgt gccattcctg ggg                                           4163
```

<210> SEQ ID NO 4
<211> LENGTH: 1278
<212> TYPE: PRT
<213> ORGANISM: Mus musculus

<400> SEQUENCE: 4

```
Met Pro Gly Val Thr Val Leu Lys Met Pro Glu Pro Gly Lys Lys Pro
1               5                   10                  15

Val Ser Ala Phe Asn Lys Lys Pro Arg Ser Ala Glu Val Thr Ala Gly
            20                  25                  30

Ser Ala Ala Val Phe Glu Ala Glu Thr Glu Arg Ser Gly Val Lys Val
        35                  40                  45

Arg Trp Gln Arg Asp Gly Ser Asp Ile Thr Ala Asn Asp Lys Tyr Gly
    50                  55                  60

Leu Ala Ala Glu Gly Lys Arg His Thr Leu Thr Val Arg Asp Ala Ser
65                  70                  75                  80

Pro Asp Asp Gln Gly Ser Tyr Ala Val Ile Ala Gly Ser Ser Lys Val
                85                  90                  95

Lys Phe Asp Leu Lys Val Thr Glu Pro Ala Pro Pro Glu Lys Ala Glu
            100                 105                 110

Ser Glu Val Ala Pro Gly Ala Pro Lys Glu Val Pro Ala Pro Ala Thr
        115                 120                 125

Glu Leu Glu Glu Ser Val Ser Ser Pro Glu Gly Ser Val Ser Val Thr
    130                 135                 140

Gln Asp Gly Ser Ala Ala Glu His Gln Gly Ala Pro Asp Asp Pro Ile
145                 150                 155                 160

Gly Leu Phe Leu Met Arg Pro Gln Asp Gly Glu Val Thr Val Gly Gly
                165                 170                 175
```

```
Ser Ile Val Phe Ser Ala Arg Val Ala Gly Ala Ser Leu Leu Lys Pro
            180                 185                 190

Pro Val Val Lys Trp Phe Lys Gly Lys Trp Val Asp Leu Ser Ser Lys
        195                 200                 205

Val Gly Gln His Leu Gln Leu His Asp Ser Tyr Asp Arg Ala Ser Lys
    210                 215                 220

Val Tyr Leu Phe Glu Leu His Ile Thr Asp Ala Gln Thr Thr Ser Ala
225                 230                 235                 240

Gly Gly Tyr Arg Cys Glu Val Ser Thr Lys Asp Lys Phe Asp Ser Cys
                245                 250                 255

Asn Phe Asn Leu Thr Val His Glu Ala Ile Gly Ser Gly Asp Leu Asp
            260                 265                 270

Leu Arg Ser Ala Phe Arg Arg Thr Ser Leu Ala Gly Ala Gly Arg Arg
        275                 280                 285

Thr Ser Asp Ser His Glu Asp Ala Gly Thr Leu Asp Phe Ser Ser Leu
    290                 295                 300

Leu Lys Lys Arg Asp Ser Phe Arg Arg Asp Ser Lys Leu Glu Ala Pro
305                 310                 315                 320

Ala Glu Glu Asp Val Trp Glu Ile Leu Arg Gln Ala Pro Pro Ser Glu
                325                 330                 335

Tyr Glu Arg Ile Ala Phe Gln His Gly Val Thr Asp Leu Arg Gly Met
            340                 345                 350

Leu Lys Arg Leu Lys Gly Met Lys Gln Asp Glu Lys Lys Ser Thr Ala
        355                 360                 365

Phe Gln Lys Lys Leu Glu Pro Ala Tyr Gln Val Asn Lys Gly His Lys
    370                 375                 380

Ile Arg Leu Thr Val Glu Leu Ala Asp Pro Asp Ala Glu Val Lys Trp
385                 390                 395                 400

Leu Lys Asn Gly Gln Glu Ile Gln Met Ser Gly Ser Lys Tyr Ile Phe
                405                 410                 415

Glu Ser Val Gly Ala Lys Arg Thr Leu Thr Ile Ser Gln Cys Ser Leu
            420                 425                 430

Ala Asp Asp Ala Ala Tyr Gln Cys Val Val Gly Gly Glu Lys Cys Ser
        435                 440                 445

Thr Glu Leu Phe Val Lys Glu Pro Pro Val Leu Ile Thr Arg Ser Leu
    450                 455                 460

Glu Asp Gln Leu Val Met Val Gly Gln Arg Val Glu Phe Glu Cys Glu
465                 470                 475                 480

Val Ser Glu Glu Gly Ala Gln Val Lys Trp Leu Lys Asp Gly Val Glu
                485                 490                 495

Leu Thr Arg Glu Glu Thr Phe Lys Tyr Arg Phe Lys Lys Asp Gly Arg
            500                 505                 510

Lys His His Leu Ile Ile Asn Glu Ala Thr Leu Glu Asp Ala Gly His
        515                 520                 525

Tyr Ala Val Arg Thr Ser Gly Gly Gln Ser Leu Ala Glu Leu Ile Val
    530                 535                 540

Gln Glu Lys Lys Leu Glu Val Tyr Gln Ser Ile Ala Asp Leu Ala Val
545                 550                 555                 560

Gly Ala Lys Asp Gln Ala Val Phe Lys Cys Glu Val Ser Asp Glu Asn
                565                 570                 575

Val Arg Gly Val Trp Leu Lys Asn Gly Lys Glu Leu Val Pro Asp Asn
            580                 585                 590
```

```
Arg Ile Lys Val Ser His Ile Gly Arg Val His Lys Leu Thr Ile Asp
        595                 600                 605

Asp Val Thr Pro Ala Asp Glu Ala Asp Tyr Ser Phe Val Pro Glu Gly
    610                 615                 620

Phe Ala Cys Asn Leu Ser Ala Lys Leu His Phe Met Glu Val Lys Ile
625                 630                 635                 640

Asp Phe Val Pro Arg Gln Glu Pro Pro Lys Ile His Leu Asp Cys Pro
                645                 650                 655

Gly Ser Thr Pro Asp Thr Ile Val Val Val Ala Gly Asn Lys Leu Arg
            660                 665                 670

Leu Asp Val Pro Ile Ser Gly Asp Pro Ala Pro Thr Val Val Trp Gln
        675                 680                 685

Lys Thr Val Thr Gln Gly Lys Lys Ala Ser Thr Gly Pro His Pro Asp
    690                 695                 700

Ala Pro Glu Asp Ala Gly Ala Asp Glu Glu Trp Val Phe Asp Lys Lys
705                 710                 715                 720

Leu Leu Cys Glu Thr Glu Gly Arg Val Arg Val Glu Thr Thr Lys Asp
                725                 730                 735

Arg Ser Val Phe Thr Val Glu Gly Ala Glu Lys Glu Asp Glu Gly Val
            740                 745                 750

Tyr Thr Val Thr Val Lys Asn Pro Val Gly Glu Asp Gln Val Asn Leu
        755                 760                 765

Thr Val Lys Val Ile Asp Val Pro Asp Ala Pro Ala Ala Pro Lys Ile
    770                 775                 780

Ser Asn Val Gly Glu Asp Ser Cys Thr Val Gln Trp Glu Pro Pro Ala
785                 790                 795                 800

Tyr Asp Gly Gly Gln Pro Val Leu Gly Tyr Ile Leu Glu Arg Lys Lys
                805                 810                 815

Lys Lys Ser Tyr Arg Trp Met Arg Leu Asn Phe Asp Leu Leu Arg Glu
            820                 825                 830

Leu Ser His Glu Ala Arg Arg Met Ile Glu Gly Val Ala Tyr Glu Met
        835                 840                 845

Arg Val Tyr Ala Val Asn Ala Val Gly Met Ser Arg Pro Ser Pro Ala
    850                 855                 860

Ser Gln Pro Phe Met Pro Ile Gly Pro Pro Gly Glu Pro Thr His Leu
865                 870                 875                 880

Ala Val Glu Asp Val Ser Asp Thr Thr Val Ser Leu Lys Trp Arg Pro
                885                 890                 895

Pro Glu Arg Val Gly Ala Gly Gly Leu Asp Gly Tyr Ser Val Glu Tyr
            900                 905                 910

Cys Gln Glu Gly Cys Ser Glu Trp Thr Pro Ala Leu Gln Gly Leu Thr
        915                 920                 925

Glu Arg Thr Ser Met Leu Val Lys Asp Leu Pro Thr Gly Ala Arg Leu
    930                 935                 940

Leu Phe Arg Val Arg Ala His Asn Val Ala Gly Pro Gly Gly Pro Ile
945                 950                 955                 960

Val Thr Lys Glu Pro Val Thr Val Gln Glu Ile Leu Gln Arg Pro Arg
                965                 970                 975

Leu Gln Leu Pro Arg His Leu Arg Gln Thr Ile Gln Lys Lys Val Gly
            980                 985                 990

Glu Pro Val Asn Leu Leu Ile Pro  Phe Gln Gly Lys Pro  Arg Pro Gln
        995                 1000                 1005

Val Thr  Trp Thr Lys Glu Gly  Gln Pro Leu Ala Gly  Glu Glu Val
```

```
    1010                1015                1020

Ser Ile  Arg Asn Ser Pro Thr  Asp Thr Ile Leu Phe  Ile Arg Ala
    1025                1030                1035

Ala Arg  Arg Thr His Ser Gly  Thr Tyr Gln Val Thr  Val Arg Ile
    1040                1045                1050

Glu Asn  Met Glu Asp Lys Ala  Thr Leu Ile Leu Gln  Ile Val Asp
    1055                1060                1065

Lys Pro  Ser Pro Pro Gln Asp  Ile Arg Ile Val Glu  Thr Trp Gly
    1070                1075                1080

Phe Asn  Val Ala Leu Glu Trp  Lys Pro Pro Gln Asp  Asp Gly Asn
    1085                1090                1095

Thr Glu  Ile Trp Gly Tyr Thr  Val Gln Lys Ala Asp  Lys Lys Thr
    1100                1105                1110

Met Glu  Trp Phe Thr Val Leu  Glu His Tyr Arg Arg  Thr His Cys
    1115                1120                1125

Val Val  Ser Glu Leu Ile Ile  Gly Asn Gly Tyr Tyr  Phe Arg Val
    1130                1135                1140

Phe Ser  His Asn Met Val Gly  Ser Ser Asp Lys Ala  Ala Ala Thr
    1145                1150                1155

Lys Glu  Pro Val Phe Ile Pro  Arg Pro Gly Ile Thr  Tyr Glu Pro
    1160                1165                1170

Pro Lys  Tyr Lys Ala Leu Asp  Phe Ser Glu Ala Pro  Ser Phe Thr
    1175                1180                1185

Gln Pro  Leu Ala Asn Arg Ser  Ile Ile Ala Gly Tyr  Asn Ala Ile
    1190                1195                1200

Leu Cys  Cys Ala Val Arg Gly  Ser Pro Lys Pro Lys  Ile Ser Trp
    1205                1210                1215

Phe Lys  Asn Gly Leu Asp Leu  Gly Glu Asp Ala Arg  Phe Arg Met
    1220                1225                1230

Phe Cys  Lys Gln Gly Val Leu  Thr Leu Glu Ile Arg  Lys Pro Cys
    1235                1240                1245

Pro Tyr  Asp Gly Gly Val Tyr  Val Cys Arg Ala Thr  Asn Leu Gln
    1250                1255                1260

Gly Glu  Ala Gln Cys Glu Cys  Arg Leu Glu Val Arg  Val Pro Gln
    1265                1270                1275
```

<210> SEQ ID NO 5
<211> LENGTH: 544
<212> TYPE: DNA
<213> ORGANISM: Homo sapiens

<400> SEQUENCE: 5

```
ctcagtccat taggagccag tagcctggaa gatgtcttta cccccagcat cagttcaagt     60

ggagcagcac ataactcttg ccctctgcct tccaagattc tggtgctgag acttatggag    120

tgtcttggag gttgccttct gccccccaac cctgctccca gctggccctc ccaggcctgg    180

gttgctggcc tctgctttat caggattctc aagagggaca gctggtttat gttgcatgac    240

tgttccctgc atatctgctc tggttttaaa tagcttatct gagcagctgg aggaccacat    300

gggcttatat ggcgtggggt acatgttcct gtagccttgt ccctggcacc tgccaaaata    360

gcagccaaca ccccccaccc ccaccgccat ccccctgccc cacccgtccc ctgtcgcaca    420

ttcctccctc cgcagggctg gctcaccagg ccccagccca catgcctgct taaagccctc    480

tccatcctct gcctcaccca gtccccgctg agactgagca gacgcctcca ggatctgtcg    540
```

gcag 544

<210> SEQ ID NO 6
<211> LENGTH: 222
<212> TYPE: DNA
<213> ORGANISM: Artificial Sequence
<220> FEATURE:
<223> OTHER INFORMATION: polyadenylation signal

<400> SEQUENCE: 6
cagacatgat aagatacatt gatgagtttg gacaaaccac aactagaatg cagtgaaaaa 60
aatgctttat ttgtgaaatt tgtgatgcta ttgctttatt tgtaaccatt ataagctgca 120
ataaacaagt taacaacaac aattgcattc attttatgtt tcaggttcag ggggagatgt 180
gggaggtttt ttaaagcaag taaaacctct acaaatgtgg ta 222

<210> SEQ ID NO 7
<211> LENGTH: 133
<212> TYPE: DNA
<213> ORGANISM: Artificial Sequence
<220> FEATURE:
<223> OTHER INFORMATION: chimeric intron

<400> SEQUENCE: 7
gtaagtatca aggttacaag acaggtttaa ggagaccaat agaaactggg cttgtcgaga 60
cagagaagac tcttgcgttt ctgataggca cctattggtc ttactgacat ccactttgcc 120
tttctctcca cag 133

<210> SEQ ID NO 8
<211> LENGTH: 9026
<212> TYPE: DNA
<213> ORGANISM: Artificial Sequence
<220> FEATURE:
<223> OTHER INFORMATION: vector construct

<400> SEQUENCE: 8
ctagaattca cgcgtctcag tccattagga gccagtagcc tggaagatgt ctttaccccc 60
agcatcagtt caagtggagc agcacataac tcttgccctc tgccttccaa gattctggtg 120
ctgagactta tggagtgtct tggaggttgc cttctgcccc ccaaccctgc tcccagctgg 180
ccctcccagg cctgggttgc tggcctctgc tttatcagga ttctcaagag ggacagctgg 240
tttatgttgc atgactgttc cctgcatatc tgctctggtt ttaaatagct tatctgagca 300
gctggaggac cacatgggct tatatggcgt ggggtacatg ttcctgtagc cttgtccctg 360
gcacctgcca aaatagcagc caacaccccc cacccccacc gccatccccc tgccccaccc 420
gtcccctgtc gcacattcct ccctccgcag ggctggctca ccaggcccca gcccacatgc 480
ctgcttaaag ccctctccat cctctgcctc acccagtccc cgctgagact gagcagacgc 540
ctccaggatc tgtcggcaga agctttattg cggtagttta tcacagttaa attgctaacg 600
cagtcagtgc ttctgacaca acagtctcga acttaagctg cagaagttgg tcgtgaggca 660
ctgggcaggt aagtatcaag gttacaagac aggtttaagg agaccaatag aaactgggct 720
tgtcgagaca gagaagactc ttgcgtttct gataggcacc tattggtctt actgacatcc 780
actttgcctt tctctccaca ggtgtccact cccagttcaa ttacagctct taaggctaga 840
gtacttaata cgactcacta taggctagcc tcgagatgga ttacaaggat gacgacgata 900
agcctggtgt gactgttctc aagatgccgg agccagggaa gaaaccagtg tcagccttca 960
acaagaagcc aaggtcagcg gaggtgaccg ctggcagtgc tgccgtgttc gaggctgaga 1020

```
cggagcggtc aggcgtgaag gtgcggtggc agcgggatgg cagcgacatc accgccaatg   1080
acaagtatgg tttggcagca gagggcaagc gacacacact gacagtgcgg gatgcgagcc   1140
ctgatgacca gggttcctac gcggtcattg caggctcctc aaaggtcaag tttgacctca   1200
aggtcacaga gccagcccct ccagagaagg cagaatctga agttgctcca ggagccccca   1260
aagaagtccc tgctccagcc actgagttgg aagaaagtgt ctcaagtcct gaaggtcagt   1320
ctcggtaacc caggatggct cagctgcaga gcatcaggga gcccctgatg accctattgg   1380
cctctttctg atgcgaccac aggatggtga ggtgaccgtg ggcggcagca ttgtcttctc   1440
agcccgagtg gctggggcca gcctcctgaa accgcctgtg gtcaagtggt tcaagggcaa   1500
gtgggtggac ctgagcagca aagtgggcca gcacctgcag ctgcatgaca gctatgacag   1560
agccagcaag gtctacttgt ttgagttgca catcacagat gctcagacca cttctgctgg   1620
gggctaccgc tgtgaggtgt ctaccaagga caaatttgac agctgtaact tcaacctcac   1680
tgtccatgag gccattggtt ctggagacct ggacctcaga tcagctttcc gacgcacgag   1740
cctggcggga gcaggtcgga gaaccagtga cagccatgaa gatgctggga ctctggactt   1800
tagttccctg ctgaagaaga gagacagttt ccggagggac tcaaagctgg aggcacctgc   1860
tgaagaagac gtgtgggaga tcctgagaca ggcaccgccg tcagaatatg agcgcatcgc   1920
cttccagcac ggagtcacag accttcgagg catgctgaag aggctcaagg gcatgaagca   1980
ggatgaaaag aagagcacag cctttcagaa gaagctggag cctgcctacc aggtaaacaa   2040
gggccacaag attcggctta ctgtggaact ggctgatccg gacgccgaag tcaagtggct   2100
taagaatgga caggagatcc agatgagtgg cagcaagtac atcttcgagt ccgtcggtgc   2160
caagcgcacc ctgaccatca gccagtgctc actggctgac gacgcagcct accagtgtgt   2220
ggtgggggc gagaagtgca gcacggagct ctttgtcaaa gagcccccgg tgctgatcac   2280
tcggtccctg gaagaccagc tggtgatggt gggtcagcgg gtggagtttg agtgtgaggt   2340
ctcagaagaa ggggcccaag tcaaatggct gaaggatggg gttgagctga cacgtgagga   2400
gaccttcaaa taccggttca agaaagatgg gcggaaacac cacttgatca tcaatgaagc   2460
aaccctggag gatgcaggac actatgcagt acgcacaagt ggaggccagt cactggctga   2520
gctcattgtg caagagaaga agttggaggt ataccaaagc atcgcggacc tggcagtggg   2580
agccaaggac caggctgtgt ttaagtgtga ggtttcagat gagaatgtac gcggcgtgtg   2640
gctgaagaat gggaaggaac tggtgcctga caaccgcata aaggtgtccc atataggccg   2700
ggtccacaaa ctgaccattg acgatgtcac acctgctgat gaggctgact acagctttgt   2760
ccctgaaggg tttgcctgca acctgtctgc caagctccac ttcatggagg tcaagattga   2820
ctttgtgcct aggcaggaac ctcccaagat ccacttggat tgtcccggca gcacaccaga   2880
caccattgtg gttgttgctg ggaacaagtt acgcctggat gtccctattt ctggagaccc   2940
tgctcccact gtggtctggc agaagactgt aacacagggg aagaaggcct caactgggcc   3000
acaccctgat gccccagaag atgctggtgc tgatgaggag tgggtgtttg ataagaagct   3060
gttgtgtgag actgagggcc gggtccgggt ggagaccacc aaagaccgca gcgtctttac   3120
agtcgaaggg gcagagaagg aagatgaagg tgtctacaca gtcacagtaa agaaccccgt   3180
gggcgaggac caggtcaacc tcacagtcaa ggtcatcgat gtcccagatg ctcctgcggc   3240
ccctaagatc agcaacgtgg gcgaggactc ctgcactgtg cagtgggaac cgcctgccta   3300
tgatggcggg cagccggtcc tgggatacat cctggagcgc aagaagaaaa agagctacag   3360
```

-continued

```
gtggatgagg ctcaactttg atctgctgcg ggagctgagc cacgaggcga ggcgcatgat   3420
cgagggtgta gcctatgaga tgcgagtcta cgcagtcaat gccgtgggaa tgtccaggcc   3480
cagccctgcc tctcagccct tcatgcctat tgggccccct ggcgaaccaa cccacttggc   3540
tgtggaggat gtgtcagaca ccactgtctc actcaagtgg cggcccccag agcgcgtggg   3600
ggccggtggc ctggacggat acagcgtgga gtactgccag gagggatgct ccgagtggac   3660
acctgctctg caggggctga cagagcgcac atcgatgctg gtgaaggacc tacccactgg   3720
ggcacggctg ctgttccgag tacgggcaca caatgtggca ggtcctggag gccctatcgt   3780
caccaaggag cctgtgacag tgcaggagat actgcaacga ccacggctcc aactgcccag   3840
acacctgcgc cagaccatcc agaagaaagt tggggagcct gtgaacctcc tcatcccttt   3900
ccagggcaaa ccccggcctc aggtgacctg gaccaaagag gggcagcccc tggcaggtga   3960
ggaggtgagc atccggaaca gccccacaga cacgatcttg ttcatccgag ctgcccgccg   4020
cacccactcg ggcacctacc aggtgacagt tcgcattgag aacatggagg acaaggcaac   4080
gctgatcctg cagattgtgg acaagccaag tcctccccag gatatccgga tcgttgagac   4140
ttggggtttc aatgtggctc tggagtggaa gccaccccaa gatgatggca atacagagat   4200
ctggggttat actgtacaga aagctgacaa gaagaccatg gagtggttca cggttttgga   4260
acactaccga cgcactcact gtgtggtatc agagcttatc attggcaatg gctactactt   4320
ccgggtcttc agccataaca tggtgggttc cagtgacaaa gctgccgcca ccaaggagcc   4380
agtctttatt ccaagaccag gcatcacata tgagccaccc aaatacaagg ccctggactt   4440
ctctgaggcc ccaagcttca cccagccctt ggcaaatcgc tccatcattg caggctataa   4500
tgccatcctc tgctgtgctg tccgaggtag tcctaagccc aagatttcct ggttcaagaa   4560
tggcctggat ctgggagaag atgctcgctt ccgcatgttc tgcaagcagg gagtattgac   4620
cctggagatc aggaaaccct gccccctatga tggtggtgtc tatgtctgca gggccaccaa   4680
cttgcagggc gaggcacagt gtgagtgccg cctggaggtg cgagttcctc agtgaccagg   4740
gatccgtcga cgcggccgct tccctttagt gagggttaat gcttcgagca gacatgataa   4800
gatacattga tgagtttgga caaaccacaa ctagaatgca gtgaaaaaaa tgctttattt   4860
gtgaaatttg tgatgctatt gctttatttg taaccattat aagctgcaat aaacaagtta   4920
acaacaacaa ttgcattcat tttatgtttc aggttcaggg ggagatgtgg gaggtttttt   4980
aaagcaagta aaacctctac aaatgtggta aaatccgata agggactaga gcatggctac   5040
gtagataagt agcatggcgg gttaatcatt aactacaagg aacccctagt gatggagttg   5100
gccactccct ctctgcgcgc tcgctcgctc actgaggccg ggcgaccaaa ggtcgcccga   5160
cgcccgggct ttgcccgggc ggcctcagtg agcgagcgag cgcgccagct ggcgtaatag   5220
cgaagaggcc cgcaccgatc gcccttccca acagttgcgc agcctgaatg gcgaatggcg   5280
attccagacg attgagcgtc aaaatgtagg tatttccatg agcgtttttc cgttgcaatg   5340
gctggcggta atattgttct ggatattacc agcaaggccg atagtttgag ttcttctact   5400
caggcaagtg atgttattac taatcaaaga agtattgcga caacggttaa tttgcgtgat   5460
ggacagactc ttttactcgg tggcctcact gattataaaa acacttctca ggattctggc   5520
gtaccgttcc tgtctaaaat ccctttaatc ggcctcctgt ttagctcccg ctctgattct   5580
aacgaggaaa gcacgttata cgtgctcgtc aaagcaacca tagtacgcgc cctgtagcgg   5640
cgcattaagc gcggcgggtg tggtggttac gcgcagcgtg accgctacac ttgccagcgc   5700
cctagcgccc gctcctttcg ctttcttccc ttcctttctc gccacgttcg ccggctttcc   5760
```

```
ccgtcaagct ctaaatcggg ggctcccttt agggttccga tttagtgctt tacggcacct   5820
cgaccccaaa aaacttgatt agggtgatgg ttcacgtagt gggccatcgc cctgatagac   5880
ggtttttcgc cctttgacgt tggagtccac gttctttaat agtggactct tgttccaaac   5940
tggaacaaca ctcaacccta tctcggtcta ttcttttgat ttataaggga ttttgccgat   6000
ttcggcctat tggttaaaaa atgagctgat ttaacaaaaa tttaacgcga attttaacaa   6060
aatattaacg tctacaattt aaatatttgc ttatacaatc ttcctgtttt tggggctttt   6120
ctgattatca accggggtac atatgattga catgctagtt ttacgattac cgttcatcga   6180
ttctcttgtt tgctccagac tctcaggcaa tgacctgata gcctttgtag agacctctca   6240
aaaatagcta ccctctccgg catgaattta tcagctagaa cggttgaata tcatattgat   6300
ggtgatttga ctgtctccgg cctttctcac ccgtttgaat ctttacctac acattactca   6360
ggcattgcat ttaaaatata tgagggttct aaaaattttt atccttgcgt tgaaataaag   6420
gcttctcccg caaaagtatt acagggtcat aatgtttttg gtacaaccga tttagcttta   6480
tgctctgagg ctttattgct taattttgct aattctttgc cttgcctgta tgatttattg   6540
gatgttggaa tcgcctgatg cggtattttc tccttacgca tctgtgcggt atttcacacc   6600
gcatatggtg cactctcagt acaatctgct ctgatgccgc atagttaagc cagccccgac   6660
acccgccaac acccgctgac gcgccctgac gggcttgtct gctcccggca tccgcttaca   6720
gacaagctgt gaccgtctcc gggagctgca tgtgtcagag gttttcaccg tcatcaccga   6780
aacgcgcgag acgaaagggc ctcgtgatac gcctattttt ataggttaat gtcatgataa   6840
taatggtttc ttagacgtca ggtggcactt ttcggggaaa tgtgcgcgga acccctattt   6900
gtttattttt ctaaatacat tcaaatatgt atccgctcat gagacaataa ccctgataaa   6960
tgcttcaata atattgaaaa aggaagagta tgagtattca acatttccgt gtcgccctta   7020
ttcccttttt tgcggcattt tgccttcctg tttttgctca cccagaaacg ctggtgaaag   7080
taaaagatgc tgaagatcag ttgggtgcac gagtgggtta catcgaactg gatctcaaca   7140
gcggtaagat ccttgagagt tttcgccccg aagaacgttt tccaatgatg agcactttta   7200
aagttctgct atgtggcgcg gtattatccc gtattgacgc cgggcaagag caactcggtc   7260
gccgcataca ctattctcag aatgacttgg ttgagtactc accagtcaca gaaaagcatc   7320
ttacggatgg catgacagta agagaattat gcagtgctgc cataaccatg agtgataaca   7380
ctgcggccaa cttacttctg acaacgatcg gaggaccgaa ggagctaacc gcttttttgc   7440
acaacatggg ggatcatgta actcgccttg atcgttggga accggagctg aatgaagcca   7500
taccaaacga cgagcgtgac accacgatgc ctgtagcaat ggcaacaacg ttgcgcaaac   7560
tattaactgg cgaactactt actctagctt cccggcaaca attaatagac tggatggagg   7620
cggataaagt tgcaggacca cttctgcgct cggcccttcc ggctggctgg tttattgctg   7680
ataaatctgg agccggtgag cgtgggtctc gcggtatcat tgcagcactg gggccagatg   7740
gtaagccctc ccgtatcgta gttatctaca cgacggggag tcaggcaact atggatgaac   7800
gaaatagaca gatcgctgag ataggtgcct cactgattaa gcattggtaa ctgtcagacc   7860
aagtttactc atatatactt tagattgatt taaaacttca tttttaattt aaaaggatct   7920
aggtgaagat cctttttgat aatctcatga ccaaaatccc ttaacgtgag ttttcgttcc   7980
actgagcgtc agaccccgta gaaaagatca aaggatcttc ttgagatcct ttttttctgc   8040
gcgtaatctg ctgcttgcaa acaaaaaaac caccgctacc agcggtggtt tgtttgccgg   8100
```

```
atcaagagct accaactctt tttccgaagg taactggctt cagcagagcg cagataccaa   8160

atactgtcct tctagtgtag ccgtagttag gccaccactt caagaactct gtagcaccgc   8220

ctacatacct cgctctgcta atcctgttac cagtggctgc tgccagtggc gataagtcgt   8280

gtcttaccgg gttggactca agacgatagt taccggataa ggcgcagcgg tcgggctgaa   8340

cggggggttc gtgcacacag cccagcttgg agcgaacgac ctacaccgaa ctgagatacc   8400

tacagcgtga gctatgagaa agcgccacgc ttcccgaagg gagaaaggcg gacaggtatc   8460

cggtaagcgg cagggtcgga acaggagagc gcacgaggga gcttccaggg ggaaacgcct   8520

ggtatcttta tagtcctgtc gggtttcgcc acctctgact tgagcgtcga tttttgtgat   8580

gctcgtcagg ggggcggagc ctatggaaaa acgccagcaa cgcggccttt ttacggttcc   8640

tggccttttg ctggcctttt gctcacatgt tctttcctgc gttatcccct gattctgtgg   8700

ataaccgtat taccgccttt gagtgagctg ataccgctcg ccgcagccga acgaccgagc   8760

gcagcgagtc agtgagcgag gaagcggaag agcgcccaat acgcaaaccg cctctccccg   8820

cgcgttggcc gattcattaa tgcagcagct gcgcgctcgc tcgctcactg aggccgcccg   8880

ggcaaagccc gggcgtcggg cgacctttgg tcgcccggcc tcagtgagcg agcgagcgcg   8940

cagagaggga gtggccaact ccatcactag gggttccttg tagttaatga ttaacccgcc   9000

atgctactta tctacgtagc catgct                                        9026


<210> SEQ ID NO 9
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 9

ggattacaag gatgacgacg a                                               21


<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10

tccagagtcc cagcatcttc                                                 20


<210> SEQ ID NO 11
<211> LENGTH: 59
<212> TYPE: DNA
<213> ORGANISM: Artificial Sequence
<220> FEATURE:
<223> OTHER INFORMATION: oligonucleotide primer

<400> SEQUENCE: 11

ttcgacctcg agatggatta caaggatgac gacgataagc ctggtgtgac tgttctcaa      59


<210> SEQ ID NO 12
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 12

ttcgacggat ccctggtcac tgaggaactc                                      30
```

<210> SEQ ID NO 13
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 13
aaaaaaacgc gtctcagtcc attaggagcc agtagc 36

<210> SEQ ID NO 14
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 14
cccccccaag cttctgccga cagatcctgg aggcg 35

<210> SEQ ID NO 15
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 15
ctcagtccat taggagccag t 21

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
aaggcaacct ccaagacact 20

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 17
ggattacaag gatgacgacg a 21

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
tccagagtcc cagcatcttc 20

<210> SEQ ID NO 19
<211> LENGTH: 20
<212> TYPE: DNA
<213> ORGANISM: Artificial Sequence
<220> FEATURE:

<223> OTHER INFORMATION: oligonucleotide primer

<400> SEQUENCE: 19
cctggtgtga ctgttctcaa 20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 20
tccagagtcc cagcatcttc 20

<210> SEQ ID NO 21
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 21
ctcaagctca tggctacact cttctc 26

<210> SEQ ID NO 22
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 22
agagcagaca ctgtttggaa gga 23

<210> SEQ ID NO 23
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 23
gatgcgagcc ctgatgac 18

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
gacttgagac actttcttcc 20

<210> SEQ ID NO 25
<211> LENGTH: 16
<212> TYPE: DNA
<213> ORGANISM: Artificial Sequence
<220> FEATURE:
<223> OTHER INFORMATION: oligonuleotide probe

<400> SEQUENCE: 25
ctcactgtcc ataagg 16

<210> SEQ ID NO 26
<211> LENGTH: 14
<212> TYPE: DNA
<213> ORGANISM: Artificial Sequence
<220> FEATURE:
<223> OTHER INFORMATION: oligonuleotide probe

<400> SEQUENCE: 26
ccagcaagag gcca 14

<210> SEQ ID NO 27
<211> LENGTH: 25
<212> TYPE: DNA
<213> ORGANISM: Artificial Sequence
<220> FEATURE:
<223> OTHER INFORMATION: oligonuleotide probe

<400> SEQUENCE: 27
tcggagaacc agcccctgct agctc 25

<210> SEQ ID NO 28
<211> LENGTH: 3895
<212> TYPE: DNA
<213> ORGANISM: homo sapiens

<400> SEQUENCE: 28
atgcctgagc cggggaagaa gccagtctca gcttttagca agaagccacg gtcagtggaa 60
gtggccgcag gcagccctgc cgtgttcgag gccgagacag agcgggcagg agtgaaggtg 120
cgctggcagc gcggaggcag tgacatcagc gccagcaaca agtacggcct ggccacagag 180
ggcacacggc atacgctgac agtgcgggaa gtgggccctg ccgaccaggg atcttacgca 240
gtcattgctg gctcctccaa ggtcaagttc gacctcaagg tcatagaggc agagaaggca 300
gagcccatgc tggcccctgc ccctgcccct gctgaggcca ctggagcccc tggagaagcc 360
ccggccccag ccgctgagct gggagaaagt gccccaagtc ccaaagggtc aagctcagca 420
gctctcaatg gtcctacccc tggagccccc gatgacccca ttggcctctt cgtgatgcgg 480
ccacaggatg gcgaggtgac cgtggaggcc atgggcaccg gagacctgga cctcctatca 540
gccttccgcc gcacgagcct ggctggaggt ggtcggcgga tcagtgatag ccatgaggac 600
actgggattc tggacttcag ctcactgctg aaaaagagag acagtttccg gaccccgagg 660
gactcgaagc tggaggcacc agcagaggag gacgtgtggg agatcctacg gcaggcaccc 720
ccatctgagt acgagcgcat cgccttccag tacggcgtca ctgacctgcg cggcatgcta 780
aagaggctca agggcatgag gcgcgatgag aagaagagca cagcctttca gaagaagctg 840
gagccggcct accaggtgag caaaggccac aagatccggc tgaccgtgga actggctgac 900
catgacgctg aggtcaaatg gctcaagaat ggccaggaga tccagatgag cggcagcaag 960
tacatctttg agtccatcgg tgccaagcgt accctgacca tcagccagtg ctcattggcg 1020
gacgacgcag cctaccagtg cgtggtgggt ggcgagaagt gtagcacgga gctctttgtg 1080
aaagagcccc ctgtgctcat cacgcgcccc ttggaggacc agctggtgat ggtggggcag 1140
cgggtggagt ttgagtgtga agtatcggag gagggggcgc aagtcaaatg gctgaaggac 1200
ggggtggagc tgacccggga ggagaccttc aaataccggt tcaagaagga cgggcagaga 1260
caccacctga tcatcaacga ggccatgctg gaggacgcgg ggcactatgc actgtgcact 1320
agcgggggcc aggcgctggc tgagctcatt gtgcaggaaa agaagctgga ggtgtaccag 1380
agcatcgcag acctgatggt gggcgcaaag gaccaggcgg tgttcaaatg tgaggtctca 1440

```
gatgagaatg ttcggggtgt gtggctgaag aatgggaagg agctggtgcc cgacagccgc   1500
ataaaggtgt cccacatcgg gcgggtccac aaactgacca ttgacgacgt cacacctgcc   1560
gacgaggctg actacagctt tgtgcccgag ggcttcgcct gcaacctgtc agccaagctc   1620
cacttcatgg aggtcaagat tgacttcgta cccaggcagg aacctcccaa gatccacctg   1680
gactgcccag gccgcatacc agacaccatt gtggttgtag ctggaaataa gctacgtctg   1740
gacgtcccta tctctgggga ccctgctccc actgtgatct ggcagaaggc tatcacgcag   1800
gggaataagg ccccagccag gccagcccca gatgccccag aggacacagg tgacagcgat   1860
gagtgggtgt ttgacaagaa gctgctgtgt gagaccgagg gccgggtccg cgtggagacc   1920
accaaggacc gcagcatctt cacggtcgag gggcagagaa aggaagatga gggcgtctac   1980
acggtcacag tgaagaaccc tgtgggcgag gaccaggtca acctcacagt caaggtcatc   2040
gacgtgccag acgcacctgc ggcccccaag atcagcaacg tgggagagga ctcctgcaca   2100
gtacagtggg agccgcctgc ctacgatggc gggcagccca tcctgggcta catcctggag   2160
cgcaagaaga agaagagcta ccggtggatg cggctgaact tcgacctgat tcaggagctg   2220
agtcatgaag cgcggcgcat gatcgagggc gtggtgtacg agatgcgcgt ctacgcggtc   2280
aacgccatcg gcatgtccag gcccagccct gcctcccagc ccttcatgcc tatcggtccc   2340
cccagcgaac ccacccacct ggcagtagag gacgtctctg acaccacggt ctccctcaag   2400
tggcggcccc cagagcgcgt gggagcagga ggcctggatg gctacagcgt ggagtactgc   2460
ccagagggct gctcagagtg ggtggctgcc ctgcaggggc tgacagagca cacatcgata   2520
ctggtgaagg acctgcccac gggggcccgg ctgcttttcc gagtgcgggc acacaatatg   2580
gcagggcctg gagcccctgt taccaccacg gagccggtga cagtgcagga gatcctgcaa   2640
cggccacggc ttcagctgcc caggcacctg cgccagacca ttcagaagaa ggtcggggag   2700
cctgtgaacc ttctcatccc tttccagggc aagccccggc ctcaggtgac ctggaccaaa   2760
gaggggcagc ccctggcagg cgaggaggtg agcatccgca acagccccac agacaccatc   2820
ctgttcatcc gggccgctcg ccgcgtgcat tcaggcactt accaggtgac ggtgcgcatt   2880
gagaacatgg aggacaaggc cacgctggtg ctgcaggttg ttgacaagcc aagtcctccc   2940
caggatctcc gggtgactga cgcctggggt cttaatgtgg ctctggagtg gaagccaccc   3000
caggatgtcg gcaacacgga gctctggggg tacacagtgc agaaagccga caagaagacc   3060
atggagtggt tcaccgtctt ggagcattac cgccgcaccc actgcgtggt gccagagctc   3120
atcattggca atggctacta cttccgcgtc ttcagccaga atatggttgg ctttagtgac   3180
agagcggcca ccaccaagga gcccgtcttt atccccagac caggcatcac ctatgagcca   3240
cccaactata aggccctgga cttctccgag gccccaagct tcacccagcc cctggtgaac   3300
cgctcggtca tcgcgggcta cactgctatg ctctgctgtg ctgtccgggg tagccccaag   3360
cccaagattt cctggttcaa gaatggcctg gacctgggag aagacgcccg cttccgcatg   3420
ttcagcaagc agggagtgtt gactctggag attagaaagc cctgcccctt tgacgggggc   3480
atctatgtct gcagggccac caacttacag ggcgaggcac ggtgtgagtg ccgcctggag   3540
gtgcgagtgc ctcagtgacc aggctggctc ctggggatgg ccaggtacaa ccggatgcca   3600
gccccgtgcc aggagcctgg agggaagttg gggaaacccc tccctactgt tggatgtatg   3660
tgtgacaagt gtgtctcctg tgctgcgatg gggggatcagc agggcagttg tcgggcagtc   3720
ctgagtgggt gttgcacaga ctggtccaca gggctcctga aggaagcccc tggatctttg   3780
gggtaaaagg agggtggcct caagaaacaa tgtctgggga caggcctttc tggcctgcta   3840
```

tgtcttccca atgtttattg ggcaataaaa gataagtgca gtcacagaga actca 3895

<210> SEQ ID NO 29
<211> LENGTH: 30
<212> TYPE: DNA
<213> ORGANISM: artificial
<220> FEATURE:
<223> OTHER INFORMATION: DNA sequence encoding Myc

<400> SEQUENCE: 29
gagcaaaagc ttattagcga ggaagatctg 30

<210> SEQ ID NO 30
<211> LENGTH: 10
<212> TYPE: PRT
<213> ORGANISM: artificial
<220> FEATURE:
<223> OTHER INFORMATION: Myc-tag protein sequence

<400> SEQUENCE: 30

Glu Gln Lys Leu Ile Ser Glu Glu Asp Leu
1 5 10

<210> SEQ ID NO 31
<211> LENGTH: 576
<212> TYPE: DNA
<213> ORGANISM: Human cytomegalovirus

<400> SEQUENCE: 31
tagtaatcaa ttacggggtc attagttcat agcccatata tggagttccg cgttacataa 60
cttacggtaa atggcccgcc tggctgaccg cccaacgacc cccgcccatt gacgtcaata 120
atgacgtatg ttcccatagt aacgccaata gggactttcc attgacgtca atgggtggag 180
tatttacggt aaactgccca cttggcagta catcaagtgt atcatatgcc aagtacgccc 240
cctattgacg tcaatgacgg taaatggccc gcctggcatt atgcccagta catgacctta 300
tgggactttc ctacttggca gtacatctac gtattagtca tcgctattac catggtgatg 360
cggttttggc agtacatcaa tgggcgtgga tagcggtttg actcacgggg atttccaagt 420
ctccacccca ttgacgtcaa tgggagtttg ttttggcacc aaaatcaacg ggactttcca 480
aaatgtcgta acaactccgc cccattgacg caaatgggcg gtaggcgtgt acggtgggag 540
gtctatataa gcagagctgg tttagtgaac cgtcag 576

<210> SEQ ID NO 32
<211> LENGTH: 1285
<212> TYPE: PRT
<213> ORGANISM: artificial
<220> FEATURE:
<223> OTHER INFORMATION: Myc-tagged human cMyBP-C protein

<400> SEQUENCE: 32

Met Glu Gln Lys Leu Ile Ser Glu Glu Asp Leu Asn Ser Pro Glu Pro
1 5 10 15

Gly Lys Lys Pro Val Ser Ala Phe Ser Lys Lys Pro Arg Ser Val Glu
20 25 30

Val Ala Ala Gly Ser Pro Ala Val Phe Glu Ala Glu Thr Glu Arg Ala
35 40 45

Gly Val Lys Val Arg Trp Gln Arg Gly Gly Ser Asp Ile Ser Ala Ser
50 55 60

Asn Lys Tyr Gly Leu Ala Thr Glu Gly Thr Arg His Thr Leu Thr Val

-continued

```
65                  70                  75                  80

Arg Glu Val Gly Pro Ala Asp Gln Gly Ser Tyr Ala Val Ile Ala Gly
                85                  90                  95

Ser Ser Lys Val Lys Phe Asp Leu Lys Val Ile Glu Ala Glu Lys Ala
            100                 105                 110

Glu Pro Met Leu Ala Pro Ala Pro Ala Pro Ala Glu Ala Thr Gly Ala
        115                 120                 125

Pro Gly Glu Ala Pro Ala Pro Ala Ala Glu Leu Gly Glu Ser Ala Pro
    130                 135                 140

Ser Pro Lys Gly Ser Ser Ser Ala Ala Leu Asn Gly Pro Thr Pro Gly
145                 150                 155                 160

Ala Pro Asp Asp Pro Ile Gly Leu Phe Val Met Arg Pro Gln Asp Gly
                165                 170                 175

Glu Val Thr Val Gly Gly Ser Ile Thr Phe Ser Ala Arg Val Ala Gly
            180                 185                 190

Ala Ser Leu Leu Lys Pro Pro Val Val Lys Trp Phe Lys Gly Lys Trp
        195                 200                 205

Val Asp Leu Ser Ser Lys Val Gly Gln His Leu Gln Leu His Asp Ser
    210                 215                 220

Tyr Asp Arg Ala Ser Lys Val Tyr Leu Phe Glu Leu His Ile Thr Asp
225                 230                 235                 240

Ala Gln Pro Ala Phe Thr Gly Ser Tyr Arg Cys Glu Val Ser Thr Lys
                245                 250                 255

Asp Lys Phe Asp Cys Ser Asn Phe Asn Leu Thr Val His Glu Ala Met
            260                 265                 270

Gly Thr Gly Asp Leu Asp Leu Leu Ser Ala Phe Arg Arg Thr Ser Leu
        275                 280                 285

Ala Gly Gly Gly Arg Arg Ile Ser Asp Ser His Glu Asp Thr Gly Ile
    290                 295                 300

Leu Asp Phe Ser Ser Leu Leu Lys Lys Ser Ser Ser Phe Arg Thr Pro
305                 310                 315                 320

Arg Asp Ser Lys Leu Glu Ala Pro Ala Glu Glu Asp Val Trp Glu Ile
                325                 330                 335

Leu Arg Gln Ala Pro Pro Ser Glu Tyr Glu Arg Ile Ala Phe Gln Tyr
            340                 345                 350

Gly Val Thr Asp Leu Arg Gly Met Leu Lys Arg Leu Lys Gly Met Arg
        355                 360                 365

Arg Asp Glu Lys Lys Ser Thr Ala Phe Gln Lys Lys Leu Glu Pro Ala
    370                 375                 380

Tyr Gln Val Ser Lys Gly His Lys Ile Arg Leu Thr Val Glu Leu Ala
385                 390                 395                 400

Asp His Asp Ala Glu Val Lys Trp Leu Lys Asn Gly Gln Glu Ile Gln
                405                 410                 415

Met Ser Gly Arg Tyr Ile Phe Glu Ser Ile Gly Ala Lys Arg Thr Leu
            420                 425                 430

Thr Ile Ser Gln Cys Ser Leu Ala Asp Asp Ala Ala Tyr Gln Cys Val
        435                 440                 445

Val Gly Gly Glu Lys Cys Ser Thr Glu Leu Phe Val Lys Glu Pro Pro
    450                 455                 460

Val Leu Ile Thr Arg Pro Leu Glu Asp Gln Leu Val Met Val Gly Gln
465                 470                 475                 480

Arg Val Glu Phe Glu Cys Glu Val Ser Glu Glu Gly Ala Gln Val Lys
                485                 490                 495
```

```
Trp Leu Lys Asp Gly Val Glu Leu Thr Arg Glu Glu Thr Phe Lys Tyr
            500                 505                 510

Arg Phe Lys Lys Asp Gly Gln Arg His His Leu Ile Ile Asn Glu Ala
        515                 520                 525

Met Leu Glu Asp Ala Gly His Tyr Ala Leu Cys Thr Ser Gly Gly Gln
    530                 535                 540

Ala Leu Ala Glu Leu Ile Val Gln Glu Lys Lys Leu Glu Val Tyr Gln
545                 550                 555                 560

Ser Ile Ala Asp Leu Met Val Gly Ala Lys Asp Gln Ala Val Phe Lys
                565                 570                 575

Cys Glu Val Ser Asp Glu Asn Val Arg Gly Val Trp Leu Lys Asn Gly
            580                 585                 590

Lys Glu Leu Val Pro Asp Ser Arg Ile Lys Val Ser His Ile Gly Arg
        595                 600                 605

Val His Lys Leu Thr Ile Asp Asp Val Thr Pro Ala Asp Glu Ala Asp
    610                 615                 620

Tyr Ser Phe Val Pro Glu Gly Phe Ala Cys Asn Leu Ser Ala Lys Leu
625                 630                 635                 640

His Phe Met Glu Val Lys Ile Asp Phe Val Pro Arg Gln Glu Pro Pro
                645                 650                 655

Lys Ile His Leu Asp Cys Pro Gly Arg Ile Pro Asp Thr Ile Val Val
            660                 665                 670

Val Ala Gly Asn Lys Leu Arg Leu Asp Val Pro Ile Ser Gly Asp Pro
        675                 680                 685

Ala Pro Thr Val Ile Trp Gln Lys Ala Ile Thr Gln Gly Asn Lys Ala
    690                 695                 700

Pro Ala Arg Pro Ala Pro Asp Ala Pro Glu Asp Thr Gly Asp Ser Asp
705                 710                 715                 720

Glu Trp Val Phe Asp Lys Lys Leu Leu Cys Glu Thr Glu Gly Arg Val
                725                 730                 735

Arg Val Glu Thr Thr Lys Asp Arg Ser Ile Phe Thr Val Glu Gly Ala
            740                 745                 750

Glu Lys Glu Asp Glu Gly Val Tyr Thr Val Thr Val Lys Asn Pro Val
        755                 760                 765

Gly Glu Asp Gln Val Asn Leu Thr Val Lys Val Ile Asp Val Pro Asp
    770                 775                 780

Ala Pro Ala Ala Pro Lys Ile Ser Asn Val Gly Glu Asp Ser Cys Thr
785                 790                 795                 800

Val Gln Trp Glu Pro Pro Ala Tyr Asp Gly Gly Gln Pro Ile Leu Gly
                805                 810                 815

Tyr Ile Leu Glu Arg Lys Lys Lys Lys Ser Tyr Arg Trp Met Arg Leu
            820                 825                 830

Asn Phe Asp Leu Ile Gln Glu Leu Ser His Glu Ala Arg Arg Met Ile
        835                 840                 845

Glu Gly Val Val Tyr Glu Met Arg Val Tyr Ala Val Asn Ala Ile Gly
    850                 855                 860

Met Ser Arg Pro Ser Pro Ala Ser Gln Pro Phe Met Pro Ile Gly Pro
865                 870                 875                 880

Pro Ser Glu Pro Thr His Leu Ala Val Glu Asp Val Ser Asp Thr Thr
                885                 890                 895

Val Ser Leu Lys Trp Arg Pro Pro Glu Arg Val Gly Ala Gly Gly Leu
            900                 905                 910
```

```
Asp Gly Tyr Ser Val Glu Tyr Cys Pro Glu Gly Cys Ser Glu Trp Val
        915                 920                 925

Ala Ala Leu Gln Gly Leu Thr Glu His Thr Ser Ile Leu Val Lys Asp
    930                 935                 940

Leu Pro Thr Gly Ala Arg Leu Leu Phe Arg Val Arg Ala His Asn Met
945                 950                 955                 960

Ala Gly Pro Gly Ala Pro Val Thr Thr Thr Glu Pro Val Thr Val Gln
                965                 970                 975

Glu Ile Leu Gln Arg Pro Arg Leu Gln Leu Pro Arg His Leu Arg Gln
            980                 985                 990

Thr Ile Gln Lys Lys Val Gly Glu  Pro Val Asn Leu Leu  Ile Pro Phe
        995                 1000                 1005

Gln Gly  Lys Pro Arg Pro Gln  Val Thr Trp Thr Lys  Glu Gly Gln
    1010                 1015                 1020

Pro Leu  Ala Gly Glu Glu Val  Ser Ile Arg Asn Ser  Pro Thr Asp
    1025                 1030                 1035

Thr Ile  Leu Phe Ile Arg Ala  Ala Arg Arg Val His  Ser Gly Thr
    1040                 1045                 1050

Tyr Gln  Val Thr Val Arg Ile  Glu Asn Met Glu Asp  Lys Ala Thr
    1055                 1060                 1065

Leu Val  Leu Gln Val Val Asp  Lys Pro Ser Pro Pro  Gln Asp Leu
    1070                 1075                 1080

Arg Val  Thr Asp Ala Trp Gly  Leu Asn Val Ala Leu  Glu Trp Lys
    1085                 1090                 1095

Pro Pro  Gln Asp Val Gly Asn  Thr Glu Leu Trp Gly  Tyr Thr Val
    1100                 1105                 1110

Gln Lys  Ala Asp Lys Lys Thr  Met Glu Trp Phe Thr  Val Leu Glu
    1115                 1120                 1125

His Tyr  Arg Arg Thr His Cys  Val Val Pro Glu Leu  Ile Ile Gly
    1130                 1135                 1140

Asn Gly  Tyr Tyr Phe Arg Val  Phe Ser Gln Asn Met  Val Gly Phe
    1145                 1150                 1155

Ser Asp  Arg Ala Ala Thr Thr  Lys Glu Pro Val Phe  Ile Pro Arg
    1160                 1165                 1170

Pro Gly  Ile Thr Tyr Glu Pro  Pro Asn Tyr Lys Ala  Leu Asp Phe
    1175                 1180                 1185

Ser Glu  Ala Pro Ser Phe Thr  Gln Pro Leu Val Asn  Arg Ser Val
    1190                 1195                 1200

Ile Ala  Gly Tyr Thr Ala Met  Leu Cys Cys Ala Val  Arg Gly Ser
    1205                 1210                 1215

Pro Lys  Pro Lys Ile Ser Trp  Phe Lys Asn Gly Leu  Asp Leu Gly
    1220                 1225                 1230

Glu Asp  Ala Arg Phe Arg Met  Phe Ser Lys Gln Gly  Val Leu Thr
    1235                 1240                 1245

Leu Glu  Ile Arg Lys Pro Cys  Pro Phe Asp Gly Gly  Ile Tyr Val
    1250                 1255                 1260

Cys Arg  Ala Thr Asn Leu Gln  Gly Glu Ala Arg Cys  Glu Cys Arg
    1265                 1270                 1275

Leu Glu  Val Arg Val Pro Gln
    1280                 1285
```

<210> SEQ ID NO 33
<211> LENGTH: 22
<212> TYPE: DNA

-continued

```
<213> ORGANISM: artificial
<220> FEATURE:
<223> OTHER INFORMATION: Forward primer for exogenous MYBPC3 (in myc
      sequence)

<400> SEQUENCE: 33

gcaaaagctt attagcgagg aa                                            22


<210> SEQ ID NO 34
<211> LENGTH: 19
<212> TYPE: DNA
<213> ORGANISM: artificial
<220> FEATURE:
<223> OTHER INFORMATION: Reverse primer for exogenous MYBPC3 (in exon 2)

<400> SEQUENCE: 34

caggccgtac ttgttgctg                                                19


<210> SEQ ID NO 35
<211> LENGTH: 20
<212> TYPE: DNA
<213> ORGANISM: artificial
<220> FEATURE:
<223> OTHER INFORMATION: Forward primer for total MYBPC3 (in exon 1)

<400> SEQUENCE: 35

ggggaagaag ccagtctcag                                               20
```

GENE-THERAPY VECTORS FOR TREATING CARDIOMYOPATHY

RELATED APPLICATIONS

This application is a divisional of U.S. Ser. No. 14/785,188, filed Oct. 16, 2015, now U.S. Pat. No. 10,501,756, which is the U.S. National Stage of International Patent Application No. PCT/EP2014/057984, filed Apr. 17, 2014, each of which is hereby incorporated by reference in its entirety, and which claim priority to European Patent Application Nos. 13164212.6, filed Apr. 17, 2013, and 13198201.9, filed Dec. 18, 2013.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

The present invention relates to a gene therapy vector which is useful in the treatment or prevention of hypertrophic cardiomyopathy in a subject in need thereof. The gene therapy vector of the invention comprises a nucleic acid sequence encoding a cardiac sarcomeric protein and a cardiomyocyte-specific promoter which is operably linked to said nucleic acid sequence. The invention furthermore relates to a cell which comprises the gene therapy vector. Pharmaceutical compositions which comprise the gene therapy vector and/or a cell comprising said vector are also provided. In another aspect, the invention relates to a method for treating or preventing hypertrophic cardiomyopathy in a subject by introducing the gene therapy vector of the invention into a subject in need of treatment.

BACKGROUND OF THE INVENTION

While considerable progress has been made in the prevention of heart diseases that are caused by environmental factors, such as nicotine, hypercholesterolemia or diabetes, and in the symptomatic treatment of heart conditions, there is still a need for methods that improve the treatment of inherited cardiomyopathies. Among the cardiomyopathies that are caused by genetic factors are hypertrophic cardiomyopathy (HCM), dilated cardiomyopathy (DCM), and arrhythmogenic right ventricular cardiomyopathy (ARVC).

HCM is the most prevalent myocardial disease characterized by unexplained left ventricular hypertrophy in the absence of another cardiac or systemic disease that itself would be capable of producing the magnitude of hypertrophy evident in a given patient. HCM is associated with initially normal systolic, but impaired diastolic function (Elliott et al., 2008, Eur Heart J 29:270-276; Gersch et al., 2011, J Thorac Cardiovasc Surg 142:e153-203). HCM has a particularly high prevalence of about 1:500 in the general population (Maron et al., 1995, Circulation 92:785-789), and it is the leading cause of sudden cardiac death in younger people, particularly in athletes. Although HCM is a life-threatening disease, no curative treatment exists to date (Carrier et al., 2010, Cardiovasc Res 85:330-338; Schlossarek et al., 2011, J Mol Cell Cardiol 50:613-20).

HCM is an autosomal-dominant disease which is known to be caused by more than 1000 different mutations in at least 10 genes that encode components of the cardiac sarcomere, such as cardiac myosin binding protein C (MYBPC3), β-myosin heavy chain (MYH7), cardiac troponin T (TNNT2), cardiac troponin I (TNNI3), myosin ventricular essential light chain 1 (MYL3), myosin ventricular regulatory light chain 2 (MYL2), cardiac α actin (ACTC), α-tropomyosin (TPM1), titin (TTN), four-and-a-half LIM protein 1 (FHL1) (Richard et al., 2003, Circulation 107:2227-2232; Schlossarek et al., 2011, J Mol Cell Cardiol 50:613-20; Friedrich et al., 2012, Hum Mol Genet 21:3237-54). Most mutations are missense mutations which encode full-length mutant polypeptides. The most known exceptions are MYBPC3 and FHL1, which exhibit mainly frameshift mutations leading to C-terminal truncated proteins.

The most frequently mutated gene in HCM is MYBPC3 which encodes cardiac myosin binding protein C (cMyBP-C) (Bonne et al., 1995, Nature Genet 11:438-440; Watkins et al., N Engl J Med., 2011, 364:1643-56). cMyBP-C is a major component of the A-band of the sarcomere, where it interacts with myosin, actin and titin (Schlossarek et al., 2011, J Mol Cell Cardiol 50:613-20). In humans and mice cMyBP-C is exclusively detected in the heart (Fougerousse et al, 1998, Circ Res 82:130-133) and is involved in the regulation of cardiac contraction and relaxation (Pohlmann et al., 2007, Circ Res Circ Res 101, 928-38; Schlossarek et al., 2011, J Mol Cell Cardiol 50:613-20). About 70% of the mutations in the MYBPC3 gene result in a frameshift and produce C-terminal truncated proteins (Carrier et al., 1997, Circ Res 80:427-434). Truncated proteins are unstable and have never been detected in myocardial tissue of patients (Marston et al., 2009, Circ Res 105:219-222; van Dijk et al., 2009, Circulation 119:1473-1483; van Dijk et al., 2012, Circ Heart Fail 5:36-46).

Therefore, a reduced level of cMyBP-C protein is one argument that haploinsufficiency is a likely disease mechanism of HCM. An insufficient amount of full-length cMyBP-C could produce an imbalance in the stoichiometry of the thick filament components and alter sarcomeric structure and function. Haploinsufficiency is also involved in mouse and cat models of HCM that carry either missense or frameshift mutations (Meurs et al., 2005, Hum Mol Genet 14:3587-3593; Vignier et al., 2009, Circ Res 105:239-248). In addition, in both cats and mice, there is evidence for the presence of mutant cMyBP-C (full-length or truncated), even at low level. Therefore, a second likely disease mechanism is the generation of toxic polypeptide inducing a dominantnegative effect, most probably by competing with the wild-type (WT) gene product.

Current drug-based treatments of HCM are merely empiric, can alleviate the symptoms but do not treat the genetic cause underlying the disease. Clearly, a gene-based or RNA-based therapy would be the only curative treatment for HCM. Gene therapeutic approaches have successfully been tested in connection with non-genetic cardiac diseases (Jessup et al., 2011, Circulation 124:304-313).

US applications 2005/0276804 and 2007/0292438 disclose that cMyBP-C is associated with genetic cardiac disorders. However, US 2005/0276804 suggests a reduction of retinol binding protein or retinoid to treat these disorders. US 2007/0292438 is limited to the disclosure of different mouse models having disruptions in various genes.

US applications 2004/0086876 and US 2002/0127548 disclose the diagnosis of mutations in the human MYBPC3 gene which are associated with HCM. Further, these applications suggest treating HCM by administration of a nucleic acid which encodes a non-mutated cMyBP-C to the patient.

Merkulov et al., 2012, Circ Heart Fail, 5:635-644 disclose the transfer of the murine Mybpc3 gene into the myocardium of cMyBP-C-deficient (cMyBP-$C^{-/-}$) mice. The authors assume that the absence of cMyBP-C results in dysfunction and hypertrophy. The gene transfer improved systolic and diastolic contractile function and led to reductions in left ventricular wall thickness in the cMyBP-C-deficient (cMyBP-$C^{-/-}$) mice.

Vignier et al., 2009, Circ Res 105:239-248 developed a Mybpc3-targeted knock-in (KI) mouse model carrying a G>A point mutation that results in different mutant mRNAs and proteins originating from abnormal gene transcription and splicing. It was shown that exogenous stress, such as adrenergic stress or aging, leads to a saturation and finally to an impairment of the ubiquitinproteasome system (UPS) in the KI mice and potentially to a subsequent accumulation of the mutant cMyBP-C polypeptides.

The present inventors found that in subjects suffering from HCM due to a heteroallelic mutation acting in a dominant-negative fashion in a gene encoding a cardiac sarcomeric protein, the introduction of a gene transfer vector which provides the corresponding non-mutated gene not only restores normal levels of the sarcomeric protein, but also minimizes the deleterious effects of toxic mutant polypeptides that are otherwise generated through transcription of mutant allele(s).

A vector-induced expression of an exogenous wild-type (WT) gene under the control of a cardiomyocyte-specific promoter thus overcomes the dominant-negative effect of the mutant protein in a subject which carries a mutated MYBPC3 allele and is not toxic, because, surprisingly, expression of the normal allele via the gene therapy vector effectively reduces the expression of the endogenous mutant allele. This effect is considered to occur as a cardiac cell-autonomous phenomenon due to tight intracellular control of the homeostasis and turnover of sarcomeric proteins.

DESCRIPTION OF THE INVENTION

The invention relates to novel therapeutic approaches for treating or preventing HCM. It is known that mutations in a number of genes which encode cardiac sarcomeric proteins lead to a reduced level of functional full-length sarcomeric protein. This is due to frameshift mutations which produce truncated mutant polypeptides, which are normally degraded by the ubiquitin-proteasome system (UPS). However, under conditions of exogenous stress, the function of the UPS may be disturbed which results in the accumulation of the mutant polypeptides, which can thus be incorporated into the sarcomere and act as a poison peptide in a dominant-negative fashion on the wildtype cMyBP-C, contributing to the pathogenesis of HCM (Vignier et al., 2009, see above). Similar observations have been made for the four-and-a-half LIM protein 1 (Friedrich et al., 2012, Hum Mol Genet 21:3237-3254). A Mybpc3-targeted knock-out, which does not produce any mutant cMyBP-C polypeptides, did not show any impairment of the UPS under the same conditions (Schlossarek et al., 2012, Basic Res Cardiol 107:1-13; Schlossarek et al., 2012, J Muscle Res Cell Motil 33: 5-15.

It is shown herein that gene transfer of wild-type cDNA, which encodes a functional version of a cardiac sarcomeric protein (such as cMyBP-C), via a gene therapy vector into a subject which carries the mutation in the gene of said cardiac sarcomeric protein, not only restores the normal level of the protein in the myocardium (i.e. the muscle tissue of the heart which is constituted by cardiomyocytes), but also prevents the production of toxic mRNAs and/or toxic polypeptides that would otherwise result from expression of the mutated allele encoding the cardiac sarcomeric protein in the genome of said subject. It was also observed that the introduction of high amounts of the gene therapy vector is not associated with a high risk for the patient to be treated, since it was not found to result in excessive amounts of the exogenous wild-type (WT) protein within the cells. Unexpectedly, the expression of cardiac sarcomeric proteins appears to be stochiometrically tightly regulated in the cell which means that it is not possible to provide the exogenous protein in amounts that could be harmful to the patient. Accordingly, the invention provides a simple and safe method for the treatment of HCM in a subject.

The combined effects of providing sufficient levels of normal cDNA resulting in adequate production of the cardiac sarcomeric protein and suppression of the toxic mRNAs/polypeptides result in an effective treatment of HCM. Without wishing to be bound by theory, it is assumed that the exogenous gene expression through the gene therapy vector reduces endogenous expression from the mutated allele by competing for sarcomeric-specific transcription factors.

In a first aspect, the invention therefore provides a gene therapy vector for expressing an exogenous nucleic acid sequence comprising:

(a) a nucleic acid sequence encoding a functional cardiac sarcomeric protein and, (b) a cardiomyocyte-specific promoter which is operably linked to said nucleic acid sequence.

The gene therapy vector is suitable for use in treating or preventing HCM in a mammalian subject in need of treatment, preferably a human subject. The subject in need of treatment is one that carries a mutation in the corresponding gene encoding said cardiac sarcomeric protein which contributes to HCM. After administration into the subject to be treated, the vector provides for the expression of the encoded cardiac sarcomeric protein in the subject, preferably in the myocardium of said subject.

The cardiac sarcomeric protein to be expressed in the subject is known to be associated with HCM, i.e. mutations in the gene encoding the cardiac sarcomeric protein which lead to expression of a non-functional protein variant, e.g. a full-length or truncated variant or mutant, eventually cause HCM. To date mutations in at least ten different genes encoding cardiac sarcomeric proteins are known to cause HCM. The sarcomere is the basic unit of a muscle and is defined as the segment between two adjacent Z-discs. According to the invention, the sarcomeric protein to be expressed by the gene therapy vector is a cardiac sarcomeric protein which means that the protein naturally occurs in the sarcomere of the cardiac muscle.

The cardiac sarcomeric protein to be expressed in the subject may be a structural or regulatory protein which is present in the cardiac sarcomere. The protein is preferably selected from the group consisting of β-myosin heavy chain (encoded by the gene MYH7, RefSeqGene NG_007884.1), myosin ventricular essential light chain 1 (encoded by the gene MYL3, RefSeqGene NG_007555.2), myosin ventricular regulatory light chain 2 (encoded by the gene MYL2, RefSeqGene NG_007554.1), cardiac α actin (encoded by the gene ACTC1, RefSeqGene NG_007553.1), α-tropomyosin (encoded by the gene TPM1, RefSeqGene NG_007557.1), cardiac troponin T (encoded by the gene TNNT2, RefSeqGene NG_007556.1), cardiac troponin I (encoded by the gene TNNI3, RefSeqGene NG_007866.2), cardiac myosin binding protein C (encoded by the gene MYBPC3, RefSeqGene NG_007667.1), titin (encoded by the gene TTN, RefSeqGene NG_011618.1), and four-and-a-half LIM protein 1 (encoded by the gene FHL1, RefSeqGene NG_015895.1) (Richard et al., 2003, Circulation 107: 2227-2232; Friedrich et al., 2012, Hum Mol Genet, 21:3237-54).

It is preferred that the cardiac sarcomeric protein to be expressed by the gene therapy vector of the invention is cardiac myosin-binding protein C (cMyBP-C). The protein can be derived from different species, such as mouse, cat, pig or monkey. In one preferred embodiment of the invention, the cMyBP-C protein to be expressed is a murine cMyBP-C, preferably a murine cMyBP-C having the amino acid sequence depicted in SEQ ID NO:4 (NCBI accession number: NP_032679.2) of the enclosed sequence listing or a sequence having at least 80% sequence identity thereto. The nucleotide sequence encoding the murine cMyBP-C of SEQ ID NO:4 is depicted in SEQ ID NO:3 (NCBI accession number: NM_008653.2).

The present invention particularly envisages the treatment of human patients suffering from HCM. Thus, in another preferred embodiment of the invention, the nucleic acid inserted in the vector which encodes a human cMyBP-C protein is of human origin. Preferably, the human cMyBP-C protein has the amino acid sequence depicted in SEQ ID NO:2 (NCBI accession number: NP_000247.2) or a sequence having at least 80% sequence identity thereto. The nucleotide sequence encoding the human cMyBP-C protein is shown in SEQ ID NO:1 (NM_000256.2).

The protein to be expressed may also be a functional variant of one of the above-mentioned proteins which exhibits a significant amino acid sequence identity compared to the original protein.

Preferably, the amino acid identity amounts to at least 60%, 65%, 70%, 75%, 80%, 85%, 90%, 95%, 96%, 97%, 98%, or 99%. Preferably, the amino acid identity of the variant is at least 70%, 80% or 90%. In this context, the term "functional variant" means that the variant of the sarcomeric protein is capable of fulfilling the function of the naturally occurring cardiac sarcomeric protein, e.g. providing structural/functional support.

Functional variants of a cardiac sarcomeric protein may include, for example, proteins which differ from their naturally occurring counterparts by one or more amino acid substitutions, deletions or additions. For example, a variant protein of the human cMyBP-C protein depicted in SEQ ID NO:2 may have an amino acid sequence with 2, 3, 4, 5, 6, or up to 10, 20, 30 or more positions which have been substituted by another amino acid relative to SEQ ID NO:2. For example, the functional variant may e.g. be selected from the group consisting of the naturally occurring Mybpc3 splice variant lacking exons 5 and 6, termed variant 4 (as shown in SEQ ID NO:28).

The amino acid substitutions can be conservative or non-conservative. It is preferred that the substitutions are conservative substitutions, i.e. a substitution of an amino acid residue by an amino acid of similar polarity, which acts as a functional equivalent. Preferably, the amino acid residue used as a substitute is selected from the same group of amino acids as the amino acid residue to be substituted. For example, a hydrophobic residue can be substituted with another hydrophobic residue, or a polar residue can be substituted with another polar residue having the same charge.

Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

Also considered as variants are proteins which differ from their naturally occurring counterparts by one or more (e.g. 2, 3, 4, 5, 10, or 15) additional amino acids. These additional amino acids may be present within the amino acid sequence of the original sarcomeric protein (i.e. as an insertion), or they may be added to one or both termini of the protein. Basically, insertions can take place at any position if the addition of amino acids does not impair the capability of the polypeptide to fulfill the function of the naturally occurring cardiac sarcomeric protein and/or rescue the haploinsufficiency in the treated subject. Moreover, variants of sarcomeric proteins also comprise proteins in which, compared to the original polypeptide, one or more amino acids are lacking. Such deletions may affect any amino acid position provided that it does not impair the ability to fulfill the normal function of the cardiac sarcomeric protein and/or rescue the haploinsufficiency.

Finally, variants of the cardiac sarcomeric proteins also refer to proteins which differ from the naturally occurring protein by structural modifications, such as modified amino acids. According to the invention, modified amino acids are amino acids which have been modified either by natural processes, such as processing or post-translational modifications, or by chemical modification processes known in the art. Typical amino acid modifications comprise phosphorylation, glycosylation, acetylation, O-Linked N-acetylglucosamination, glutathionylation, acylation, branching, ADP ribosylation, crosslinking, disulfide bridge formation, formylation, hydroxylation, carboxylation, methylation, demethylation, amidation, cyclization and/or covalent or non-covalent bonding to phosphotidylinositol, flavine derivatives, lipoteichonic acids, fatty acids or lipids. Such modifications have been extensively described in the literature, e.g., in Proteins: Structure and Molecular Properties, T. Creighton, 2$^{nd}$ edition, W. H. Freeman and Company, New York (1993). In a preferred embodiment of the invention, the nucleic acid sequence encodes a constitutively phosphorylated isoform of human cMyBP-C. It has been shown that these isoforms are particularly cardioprotective (Sadayappan et al. (2005), Circ Res 97:1156-1163; Sadayappan et al., 2006; Proc Natl Acad Sci USA 103:16918-16923).

The gene therapy vector is preferably for treating or preventing HCM in a subject in need thereof. The subject to be treated with the vectors can be a subject that has been diagnosed with HCM, a subject with an increased risk for developing HCM, or a subject predisposed to develop HCM. In a preferred aspect of the invention, the subject is a human subject diagnosed with HCM as a result of a mutation in at least one of the alleles of a gene encoding a cardiac sarcomeric protein which is known to be associated with HCM.

In another preferred aspect of the invention, the subject which is treated with the vector of the invention carries a gene mutation that impairs the function of said cardiac sarcomeric protein and, as a result of the mutation, produces one or more dysfunctional protein species which originate from the cardiac sarcomeric protein.

In another preferred aspect of the invention, the mutation in the cardiac sarcomeric protein causes haploinsufficiency in said subject. Haploinsufficiency designates a state of a diploid organism, which is characterized by one dysfunctional allele, wherein the remaining functional allele does not produce a sufficient level of the gene product to generate the wild-type phenotype.

The present invention is based on the surprising insight that the phenotype of HCM can be effectively ameliorated or eradicated by administration of a gene therapy vector which provides an intact, exogenous version of the wild-type gene which compensates for the mutated allele in the genome of the subject to be treated. It was unexpectedly found that an accumulation of toxic mRNA and/or polypeptides (both of which derive from the mutated allele) can be effectively prevented. Thus, in one embodiment, the described gene therapy vector is for use in a method of treating or preventing hypertrophic cardiomyopathy in a mammalian subject, wherein said subject produces one or more dysfunctional protein species which originate from the cardiac sarcomeric protein and, optionally, wherein administration of said therapy results in the reduction of one or more of the dysfunctional protein species. "Reduction" refers to a level of one or more of the dysfunctional protein species which is reduced by more than 20%, 30%, 40%, 50%, 60%, 70%, 80%, or 90%, compared to the level before administration. In a preferred embodiment, the level of one or more of the dysfunctional protein species is reduced by more than 20% compared to the level before administration.

Preferably, the "level of one or more of the dysfunctional protein species" is the level of all dysfunctional species of the sarcomeric protein combined, i.e. the overall level of dysfunctional species of the sarcomeric protein.

HCM describes a deterioration of the heart muscle which results in a decreased integrity. This may lead to heart rhythm disorder and ultimately to heart failure. HCM is a genetically and clinically heterogeneous disease of the sarcomere characterized inter alia by a thickening of the muscular walls in the ventricular septum and left ventricle in the absence of another cardiac or systemic disease that itself would be capable of producing the magnitude of hypertrophy evident in a given patient. As a consequence of the wall thickening, the left ventricle outflow tract may be narrowed. Characteristics of HCM are myocyte hypertrophy, myocellular disarray, interstitial fibrosis, small vessel coronary disease, and/or left ventricular outflow obstruction. HCM is associated with initially normal systolic, but impaired diastolic function in majority of cases. Thus, in a preferred embodiment of the invention, the gene therapy vector is for treating or preventing HCM in a subject in need thereof, wherein HCM is characterized by a thickening of the muscular walls in the ventricular septum and/or left ventricle and diastolic dysfunction.

When expressing a cardiac sarcomeric protein, e.g. one of the proteins mentioned above, exogenously in the subject to which the therapeutic vector has been administered, it may turn out that it is not necessary to express the full-length protein to compensate for the dysfunctional mutant protein expressed from the mutated allele. Instead, it may be sufficient to express only a functional fragment of the full-length sarcomeric protein or its variants as defined above. Thus, the present invention also comprises the use of functional fragments of the cardiac sarcomeric protein or their variants for treating or preventing HCM in a subject in need thereof. As used herein, fragments of cardiac sarcomeric proteins of the invention are proteins which differ from the naturally occurring protein by the lack of one or several amino acids at the N-terminus and/or the C-terminus, wherein at least part of the ability to fulfill the normal function of the naturally occurring cardiac sarcomeric protein is retained.

The nucleic acid sequence encoding the cardiac sarcomeric protein is administered to the subject to be treated in the form of a gene therapy vector, i.e. a nucleic acid construct which comprises the coding sequence, including the translation and termination codons, next to other sequences required for providing expression of the exogenous nucleic acid such as promoters, kozak sequences, polyA signals and the like. Gene therapy vectors for expressing an exogenous nucleic acid sequence in a subject are well known in the art.

For example, the gene therapy vector may be part of a mammalian expression system. Useful mammalian expression systems and expression constructs have been described in the prior art.

Also, several mammalian expression systems are distributed by different manufacturers and can be employed in the present invention, such as plasmid- or viral vector based systems, e.g. LENTI-Smart™ (InvivoGen), GenScript™ Expression vectors, pAdVAntage™ (Promega), ViraPower™ Lentiviral, Adenoviral Expression Systems (Invitrogen) and adeno-associated viral expression systems (Cell Biolabs).

The gene therapy vector of the invention can be, for example, a viral or non-viral expression vector which is suitable for introducing the exogenous nucleic acid into a cell for subsequent expression of the protein encoded by said nucleic acid. The vector should be specifically adapted to provide expression of the encoded sarcomeric protein in a cardiomyocyte. In a preferred embodiment the vector provides specific expression of the encoded sarcomeric protein in cardiomyocytes. The expression is "specific" when the expression is at least 2-fold higher than in other non-cardiac cell type or cardiac cell which is not a cardiomyocte.

The expression vector can be an episomal vector, i.e. one that is capable of self-replicating autonomously within the host cell, or an integrating vector, i.e. one which stably incorporates into the genome of the cell. The expression in the host cell can be constitutive or regulated (e.g. inducible). Preferably, the functional exogenous cardiac sarcomeric protein is located intracellularly, preferably in the sarcomere of the host cell.

A gene therapy vector of the invention will normally comprise a promoter which is functionally linked to the nucleic acid encoding the sarcomeric protein. The promoter sequence must be compact and ensure a strong expression. Preferably, the promoter provides for an expression of the sarcomeric protein in the myocardium of the patient that has been treated with the gene therapy vector. More preferably, the promoter provides for a specific expression of the sarcomeric protein in the myocardium of the patient. The expression is "specific" when the expression is at least 2-fold higher than in cells do not belong to the myocardium. It is further preferred that substantially no sarcomeric protein is expressed in cells that do not belong to the myocardium. "Substantially no" in this context means that less than 10%, less than 5%, less than 1% of the sarcomeric protein that is expressed from the vector is expressed in cells that do not belong to the myocardium.

Suitable promoters include, for example, the muscle creatine kinase (MCK), the cytomegalovirus enhancer+myosin light chain 2 promoter (CMV-MLC2, or CMV-MLC1.5, CMV-MLC260), the phosphoglycerate kinase (PGK), and the cardiac troponin T promoter (TNNT2), and any other sarcomere-specific promoters. Preferably, these promoters are derived from human genes.

In a particularly preferred embodiment, the gene therapy vector comprises a cardiac-specific promoter which is operably linked to the nucleic acid sequence encoding the cardiac sarcomeric protein. As used herein, a "cardiac-specific promoter" refers to a promoter whose activity in cardiac cells is at least 2-fold higher than in any other non-cardiac cell type. Preferably, a cardiac-specific promoter suitable for being used in the vector of the invention has an activity in cardiac cells which is at least 5-fold, at least 10-fold, at least 15-fold, at least 20-fold, at least 25-fold, or at least 50-fold higher compared to its activity in a non-cardiac cell type.

In a further preferred embodiment, the gene therapy vector comprises a cardiomyocyte-specific promoter which is operably linked to the nucleic acid sequence encoding the cardiac sarcomeric protein. A "cardiomyocyte-specific promoter", as used herein, specifies a promoter whose activity in cardiomyocytes is at least 2-fold higher than in any other non-cardiac cell type or cardiac cell which is not a cardiomyocte. Preferably, a cardiomyocte-specific promoter suitable for being used in the vector of the invention has an activity in cardiomyocytes which is at least 5-fold, at least 10-fold, at least 15-fold, at least 20-fold, at least 25-fold, or at least 50-fold higher compared to its activity in a non-cardiac cell type or a cardiac cell type which is not a cardiomyocte.

Preferably, the cardiac-specific or cardiomyocyte-specific promoter is a human promoter. As can be seen from the enclosed examples, one promoter that has been proven useful for the vectors of the invention is a cardiac troponin T promoter (TNNT2), such as the human TNNT2 promoter set forth in SEQ ID NO:5. Accordingly, the cardiomyocyte-specific promoter of the invention preferably comprises the sequence of SEQ ID NO:5 or a functional equivalent sequence having at least 80%, more preferably 90%, 95%, 96%, 97%, 98%, 99%, sequence identity thereto. In a preferred embodiment, the gene therapy vector comprises a TNNT2 promoter operably linked to the nucleic acid sequence encoding the cardiac sarcomeric protein. In a further preferred embodiment, the gene therapy vector comprises the human TNNT2 promoter of SEQ ID NO:5 operably linked to the nucleic acid sequence encoding the cardiac sarcomeric protein. Other cardiac-specific promoters include the alpha myosin heavy chain promoter, the myosin light chain 2v promoter, the alpha myosin heavy chain promoter, the alpha-cardiac actin promoter, the alpha-tropomyosin promoter, the cardiac troponin C promoter, the cardiac troponin I promoter, the cardiac myosin-binding protein C promoter, and the sarco/endoplasmic reticulum $Ca^{2+}$-ATPase (SERCA) promoter (e.g. isoform 2 of this promoter (SERCA2)).

Cardiac muscle tissue is striated muscle tissue that has repeating sarcomeres. Thus, in a further embodiment the gene therapy vector comprises a striated muscle promoter, such as the desmin promoter.

The cardiac-specific or cardiomyocyte-specific promoter is operably linked to the nucleic acid sequence encoding the cardiac sarcomeric protein which means that the promoter is combined with the coding nucleic acid so as to enable the expression of said coding nucleic acid under the control of the promoter in cardiac myocytes cells when integrated into the genome of the cell or present as an extragenomic nucleic acid construct in the cell.

As an optional component, the gene therapy vector can include an enhancer element for increasing the expression level of the sarcomeric protein. Examples include the SV40 early gene enhancer and the enhancer of the long terminal repeat (LTR) of Rous Sarcoma Virus (Gorman et al. (1982) Proc. Natl. Acad. Sci. 79:6777). The vector also optionally comprises transcription termination sequences and polyadenylation sequences for improved expression of the human and/or non-human antigen(s). Suitable transcription terminator and polyadenylation signals can, for example, be derived from SV40 (Sambrook et al (1989), Molecular Cloning: A Laboratory Manual). Preferably, a SV40 polyadenylation signal comprising or consisting of the sequence of SEQ ID NO:6 is used in the vector of the invention. Any other element which is known in the art to support efficiency or specificity of expression may be added to the expression vector, such as the Woodchuck hepatitis post-transcriptional regulatory element (wPRE). To increase the cardiac specificity, other elements can be introduced to inactivate the expression of genes in other tissues, such as sequences encoding miRNAs such as miR122 (Geisler et al., 2011, Gene Therapy 18:199-209). To visualize the exogenous gene expression in the heart, other optional elements can be introduced such as tag sequences (myc, FLAG, HA, His, and the like), or fluorochromes such as GFP, YFP, RFP.

To further increase the gene expression level, a chimeric intron can be introduced into the gene therapy vector of the invention. A "chimeric intron" as used herein refers to an intron that comprises parts of at least two different introns which have been derived from two different genes. Particularly preferred chimeric introns for use in the gene therapy vector of the present invention comprise, e.g. intron sequences from the human beta globin gene and human immunoglobulin G (IgG). An exemplary intron is depicted in SEQ ID NO:7. Preferably, the chimeric intron is inserted immediately downstream from the promoter. It has e.g. been shown that insertion of the beta globin/Ig intron immediately downstream of the PGK promoter increases gene expression about 37-fold (Dominguez et al., 2011, Hum Mol Genet 20:681-693).

The gene therapy vector can be constructed and cloned by standard methods known in the art, such as recombinant DNA technology or chemical synthesis. Standard cloning methods are described e.g. in Sambrook et al., 1989, Molecular Cloning: A Laboratory Manual, Cold Spring Harbour Lab Press.

In a particularly preferred aspect, the gene therapy vector is a viral expression vector. Viral vectors for use in the present invention typically comprise a viral genome in which a portion of the native sequence has been deleted in order to introduce a heterogeneous polynucleotide without destroying the infectivity of the virus. Due to the specific interaction between virus components and host cell receptors, viral vectors are highly suitable for efficient transfer of genes into target cells. Suitable viral vectors for facilitating gene transfer into a mammalian cell are well known in the art and can be derived from different types of viruses, for example, from a retrovirus, adenovirus, adeno-associated virus (AAV), orthomyxovirus, paramyxovirus, papovavirus, picornavirus, lentivirus, herpes simplex virus, vaccinia virus, pox virus or alphavirus. For an overview of the different viral vector systems, see Nienhuis et al., Hematology, Vol. 16: Viruses and Bone Marrow, N. S. Young (ed.), 353-414 (1993).

For example, retroviral vectors may be used. Retroviral vectors normally function by transducing and integrating the selected polynucleotide into the genome of the target cell. The retroviral vectors can be derived from any of the subfamilies. For example, vectors from Murine Sarcoma Virus, Bovine Leukemia, Virus Rous Sarcoma Virus, Murine Leukemia Virus, Mink-Cell FocusInducing Virus, Reticuloendotheliosis Virus, or Avian Leukosis Virus can be used. The skilled person will be able to combine portions derived from different retroviruses, such as LTRs, tRNA binding sites, and packaging signals to provide a recombinant retroviral vector. These retroviral vectors are then normally used for producing transduction competent retroviral vector particles. For this purpose, the vectors are introduced into suitable packaging cell lines, such as those described in U.S. Pat. No. 5,591,624. Retrovirus vectors can also be constructed for site-specific integration into the DNA of the host cell by incorporating a chimeric integrase enzyme into the retroviral particle. See, for example, WO 96/37626.

According to the invention, it is particularly preferred that the gene therapy vector is an adenoassociated viral (AVV) vector, such as an AAV vector selected from the group consisting of serotype 1, 2, 3, 4, 5, 6, 7, 8, 9, and 10 or chimeric AAV derived thereof, which will be even better suitable for high efficiency transduction in the tissue of interest (Wu et al., 2006, Mol Therapy 14:316-27; Bowles et al., 2012, Mol Therapy 20:443-455). Upon transfection, AAV elicits only a minor immune reaction (if any) in the host. Moreover, in contrast to other vector systems AAV vectors are also able to efficiently pass from the blood into terminally differentiated cardiomyocytes. In this respect the AAV system is superior e.g. to the use of lentivirus. Therefore, AAV is highly suited for gene therapy approaches. For transduction in mice, AAV serotype 6 and AAV serotype 9 are particularly suitable. For gene transfer into a human, AAV serotypes 1, 6, 8 and 9 are preferred. Thus, in a preferred embodiment of the invention, the gene therapy vector is an AAV serotype 6 vector. In a further preferred embodiment, the gene therapy vector is an AAV serotype 8 vector. Finally, it is most preferred that the gene therapy vector is an AAV serotype 9 vector. The AAV serotype 9 vector is particularly well suited for the induction of expression in cells of the myocardium/cardiomyocytes.

It was assumed in the prior art that the capacity of AAV for packaging a therapeutic gene is limited to approximately 4.9 kbp, while longer sequences lead to truncation of AAV particles (Wu et al., 2010, Mol Ther 18:80-86). However, it is demonstrated herein that packaging of an oversized DNA sequence of 5.4 kbp (including two inverted terminal repeats (ITRs), the FLAG-tagged Mybpc3 cDNA under the control of the human TNNT2 promoter, a chimeric intron and the SV40 polyadenylation signal) does not affect the production of the AAV serotype 6 or 9. Titers of $1\text{-}7\times10^{12}$ vector genomes per mL were achieved and the vectors induced marked expression of the FLAG-Mybpc3 gene in isolated mouse cardiac myocytes and in the mouse heart in vivo. Thus, in a preferred embodiment, the gene therapy vector comprises a polynucleotide sequence having a size of at least 4.0 kbp, at least 4.5 kbp, at least 5 kbp, at least 5.1 kbp, at least 5.2 kbp, at least 5.3 kbp, at least 5.4 kbp, at least 5.5 kbp or at least 5.6 kbp. In one embodiment, the gene therapy vector comprises a polynucleotide sequence having a size of at least 4.5 kbp. It is particularly preferred that the gene therapy vector comprises a polynucleotide sequence having a size of at least 5 kbp. In a further embodiment the gene therapy vector comprises a polynucleotide sequence having a size of at least 5.3 kbp.

Moreover, the gene therapy vectors of the invention preferably combine the advantages of a highly efficient and pharmaceutically acceptable transfection vector, such as AAV, with a cardiomyocyte-/myocardium-specific expression of the encoded cardiac sarcomeric protein, through a cardiac-specific promoter. Therefore, it is preferred that the gene therapy vector is an AAV vector that comprises a cardiac-specific promoter which is operably linked to the nucleic acid sequence encoding the cardiac sarcomeric protein. In a first preferred embodiment, the AAV vector is an AAV serotype 6. In a second preferred embodiment, the AAV vector is an AAV serotype 8. In a third preferred embodiment, the AAV vector is an AAV serotype 9. It is particularly preferred that the cardiac-specific promoter in any of these embodiments is the human TNNT2 of SEQ ID NO:5 or a functional equivalent sequence having at least 80%, more preferably 90%, 95%, 96%, 97%, 98%, 99%, sequence identity thereto. For example, the gene therapy vector is an AAV 9 vector that comprises a cardiac-specific promoter which is operably linked to the nucleic acid sequence encoding the cardiac sarcomeric protein, wherein the cardiac-specific promoter in any of these embodiments is the human TNNT2 of SEQ ID NO:5 or a functional equivalent sequence having at least 80%, more preferably 90%, 95%, 96%, 97%, 98%, 99%, sequence identity thereto.

As outlined above, the cardiac sarcomeric protein that is encoded by the gene therapy vector is preferably cardiac myosin-binding protein C (cMyBP-C). As shown in the below examples, a gene therapy vector combining the advantages of an AAV vector, a cardiomyocyte-specific promoter and expression of cardiac myosin-binding protein C is highly efficient in the treatment of patients suffering from HCM.

Thus, in a preferred embodiment, the gene therapy vector is an AAV serotype 9 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding a cMyBP-C, preferably a murine cMyBP-C having the amino acid sequence depicted in SEQ ID NO:4 or a sequence having at least 80% sequence identity thereto, or the human cMyBP-C protein having the amino acid sequence depicted in SEQ ID NO:2 or a sequence having at least 80% sequence identity thereto. In a more preferred embodiment, the gene therapy vector is an AAV serotype 9 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding the human cMyBP-C protein having the amino acid sequence depicted in SEQ ID NO:2 or a sequence having at least 80% sequence identity thereto.

Thus, in another embodiment, the gene therapy vector is an AAV serotype 6 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding a cMyBP-C, preferably a murine cMyBP-C having the amino acid sequence depicted in SEQ ID NO:4 or a sequence having at least 80% sequence identity thereto, or the human cMyBP-C protein having the amino acid sequence depicted in SEQ ID NO:2 or a sequence having at least 80% sequence identity thereto.

In a more preferred embodiment, the gene therapy vector is an AAV serotype 6 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding the human cMyBP-C protein having the amino acid sequence depicted in SEQ ID NO:2 or a sequence having at least 80% sequence identity thereto.

Thus, in another embodiment, the gene therapy vector is an AAV serotype 8 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding a cMyBP-C, preferably a murine cMyBP-C having the amino acid sequence depicted in SEQ ID NO:4 or a sequence having at least 80% sequence identity thereto, or the human cMyBP-C protein having the amino acid sequence depicted in SEQ ID NO:2 or a sequence having at least 80% sequence identity thereto. In a more preferred embodiment, the gene therapy vector is an AAV serotype 8 vector that comprises the human TNNT2 promoter of SEQ ID NO:5 or a functionally equivalent sequence having at least 80%, more preferably 90%, 95%, 96%, 97%, 98%, 99%, sequence identity thereto, wherein the promoter is operably linked to a nucleic acid sequence encoding the human cMyBP-C protein having the amino acid sequence depicted in SEQ ID NO:2 or a sequence having at least 80% sequence identity thereto.

Recombinant viral vectors can be generated according to standard techniques. For example, recombinant adenoviral or adeno-associated viral vectors can be propagated in human 293 cells (which provide E1A and E1B functions in trans) to titers in the range of $10^7$-$10^{13}$ viral particles/mL. Prior to their in vivo application viral vectors may be desalted by gel filtration methods, such as sepharose columns, and purified by subsequent filtering. Purification reduces potential deleterious effects in the subject to which the vectors are administered. The administered virus is substantially free of wild-type and replication-competent virus. The purity of the virus can be proven by suitable methods, such as sodium dodecyl sulfate-polyacrylamide gel electrophoresis (SDS-PAGE) followed by silver staining. This is applicable for both AAV and adenoviral vectors.

As described in the below examples, transduction of the gene therapy vectors of the invention into the subject to be treated can be achieved by systemic application, e.g., by intravenous, intraarterial or intraperitoneal delivery of a vector in analogy to what has been shown in animal models (Katz et al., 2012, Gene Ther 19:659-669. In a preferred embodiment, the gene therapy vectors are for use in the described method of treating or preventing hypertrophic cardiomyopathy, wherein the gene therapy vector is administered systemically.

Alternatively, the gene therapy vectors of the invention can be delivered by direct administration to the heart tissue, e.g. by intracoronary administration. In a preferred embodiment, the gene therapy vectors are administered as a single dose by antegrade epicardial coronary artery infusion over a 10-minute period in a cardiac catheterization laboratory after angiography (percutaneous intracoronary delivery without vessel balloon occlusion) with the use of standard 5F or 6F guide or diagnostic catheters (Jaski et al., 2009, J Card Fail 15:171-181).

In another preferred embodiment, tissue transduction of the myocardium is achieved by cathetermediated intramyocardial delivery (Gao et al., 2011, Hum Gene Ther 22:979-84). Importantly, this latter form of delivery can also be used to transfer vector-free cDNA coupled or not to transduction-enhancing carriers into myocardium. Cell-derived exosomes or microparticles with cardiac tropism can also be used to transport the vectors of the invention (Lee et al., 2012, Hum Mol Genet 21:R125-134). A suitable dose of AAV for humans would be in the range of about $1\times10^{10}$ to $1\times10^{14}$ virus particles, and in particular about $1\times10^{12}$.

Apart from viral vectors, non-viral expression constructs may also be used for introducing a gene encoding a functional cardiac sarcomeric protein or a functioning variant or fragment thereof into a cell or a human subject. Non-viral expression vectors which permit the in vivo expression of protein in the target cell include, for example, vectors such as pBK-CMV, pcDNA3.1, and pZeoSV (Invitrogen, Stratagene). Suitable methods for the transfer of non-viral vectors into target cells are, for example, the lipofection method, the calcium-phosphate co-precipitation method, the DEAE-dextran method and direct DNA introduction methods using micro-glass tubes and the like. Prior to the introduction of the vector, the cardiac muscle cells may be treated with a permeabilization agent, such as phosphatidylcholine, streptolysins, sodium caprate, decanoylcarnitine, tartaric acid, lysolecithin, Triton X-100, and the like.

Alternatively, isolated cells that have been removed from a subject, for example, by a biopsy procedure, may be transfected with the vector in an ex vivo procedure. The cells can then be reimplanted into or otherwise administered to a subject, preferably into the subject from whom they were obtained. In another aspect, the invention thus relates to an isolated cell, such as a cardiomyocyte or a stem cell, which has been transduced with the gene therapy vector of the invention. After transduction of the vector, the cell expresses the cardiac sarcomeric protein that was encoded by the vector. The cell preferably is a cardiac cell, such as a cardiomyocyte, or a cardiomyocyte derived from induced pluripotent stem cell (iPSC). The cell may also be a stem cell, preferably an embryonal or pluripotent adult stem cell, more preferably an endogenous cardiac stem cells (eCSCs) or an iPSC derived from fibroblasts (Okita et al., 2007, Nature 448:313-7; Yu et al., 207, Science 318:1917-20; Maekawa et al., 2011, Nature 474: 225-229), from keratinocytes (Aasen et al., 2008, Nat Biotech 11:1276-1284; Aasen & Belmonte, 2010, Nat Protocol 5:371-382) or from blood cells (Staerk et al., 2010, Stem Cell Stem 7: 20-24; Seki et al., 2012, Nat Protocol 7:718-728).

It is furthermore preferred that the cell is a human cell. The likelihood of rejection of transplanted cells is reduced when the subject from whom the cell is explanted is genetically similar to the subject to whom the cell is administered. Therefore, the cell of the invention is preferably an autologous cell that is transduced with the gene therapy vector of the invention ex vivo. After transduction of the autologous cell, the cell is reintroduced into the subject by appropriate administration means, such as transplantation or infusion.

The cell is preferably for use in a method of treating or preventing HCM in a subject, wherein mutations in the gene encoding said cardiac sarcomeric protein are associated with HCM and the subject carries a gene mutation that impairs the function of said cardiac sarcomeric protein.

The invention further relates to a pharmaceutical composition comprising the gene therapy vector of the invention. In a preferred embodiment, the composition is for use in a method of treating or preventing HCM in a subject having a dysfunctional cardiac sarcomeric protein.

Methods for the preparation of pharmaceutical compositions that contain gene therapy vectors are well known by those working in the field ofpharmaceutics. Typically, such compositions are prepared either as liquid solutions or suspensions. The pharmaceutical composition of the invention can include commonly used pharmaceutically acceptable excipients, such as diluents and carriers. In particular, the composition comprises a pharmaceutically acceptable carrier, e.g., water, saline, Ringer's Solutions, or dextrose solution. Further examples of suitable carriers are described in standard textbooks, for example, in "Remington's Pharmaceutical Sciences", Mack Pub. Co., New Jersey (1991). In addition to the carrier, the composition may also contain emulsifying agents, pH buffering agents, stabilizers, dyes and the like.

The pharmaceutical composition will comprise a therapeutically effective gene dose. A therapeutically effective gene dose is one that is capable of preventing or treating cardiomyopathy in a subject, without being toxic to the subject. Prevention or treatment of cardiomyopathy can be assessed as a change in a phenotypic characteristic associated with cardiomyopathy, such change being effective to prevent or treat cardiomyopathy. Phenotypic characteristics associated with cardiomyopathy are for example left ventricular (LV) hypertrophy, reduced fractional shortening, interstitial fibrosis as well as diastolic and systolic dysfunction. A therapeutically effective gene dose typically elicits a positive change in the phenotype of HCM, i.e. a change that approximates the phenotype of the subject suffering from HCM to the phenotype of a healthy subject which does not carry a HCM gene mutation. Thus, a therapeutically effective gene dose is typically one that, when administered in a physiologically tolerable composition, is sufficient to improve or prevent the pathogenic heart phenotype in the treated subject.

In yet another aspect, the invention relates to methods for treating or preventing HCM in a subject by introducing a gene therapy vector for expressing an exogenous nucleic acid sequence in a subject, said vector comprising:

(a) a nucleic acid sequence encoding a cardiac sarcomeric protein as defined elsewhere herein, and
(b) a cardiomyocyte-specific promoter which is operably linked to said nucleic acid sequence, wherein mutations in the gene encoding said cardiac sarcomeric protein are associated with HCM and said subject carries a gene mutation that impairs the function of said cardiac sarcomeric protein.

BRIEF DESCRIPTION OF THE FIGURES

FIG. 7 (FIG. 7.1 shows graphs/blots A-C; FIG. 7.2 shows graphs/blots D-E): Long-term Mybpc3 gene therapy in Mybpc3-targeted knock-in mice. Different doses of adeno-associated virus serotype 9 (AAV9)-Mybpc3 ($1\times10^{11}$, $3\times10^{11}$, $1\times10^{12}$ and $3\times10^{12}$ vector genomes (vg)/mouse) or PBS were administered to 1-day-old Mybpc3-targeted knock-in (KI) mice, before the appearance of the cardiac disease phenotype. All data were obtained after 34 weeks. (A) Analysis of systolic (=dP/dtmax) and diastolic (=dP/dtmin) function and determination of the heart weight to body weight ratio (HW/BW) were performed in 34-week-old WT, KI treated with PBS and KI mice treated with the highest dose of $3\times10^{12}$ vg. (B) RT-PCR for evaluation of the mRNA levels of exogenous FLAG-tagged Mybpc3 (upper panel) and total Mybpc3 (lower panel). RNA was extracted from ventricular tissues and pooled in each group (n=5-10/group). The size of the PCR-amplified bands is shown on the left side. (C) Total Mybpc3 mRNA level determined by RT-qPCR performed in 34-week-old WT, KI treated with PBS and KI mice treated with the highest dose of $3\times10^{12}$ vg. (D) Western blot for evaluation of the protein levels of exogenous FLAGtagged cMyBP-C (upper panels) and total cMyBP-C (lower panels). Ventricular protein extracts from each group were pooled for the analysis. Blots were stained with antibodies directed against the FLAG epitope or total cMyBP-C (upper part in each condition). An antibody directed against GAPDH was used as loading control (lower parts in each condition). (E) Quantification of cMyBP-C protein level normalized to GAPDH and related to WT.

EXAMPLES

Example 1: Consequences of a G>A Transition in Homozygous Mybpc3-Targeted Knock-in Mice For both ex vivo and in vivo studies, a knock-in mouse carrying a G>A transition in the Mybpc3 gene (Mybpc3-targeted knock-in; KI) has been developed by gene targeting using the Cre/lox system (Vignier et al., 2009, Circ Res 105:239-248). Briefly, a 8105 bp-fragment containing the 5' part of mouse Mybpc3 gene, which covers 1747 bp upstream of exon 1 up to exon 15, was obtained by long-range PCR or cloning from a FIX II genomic library derived from a 129/Svj mouse strain, and then cloned into the pBluescript® II KS+vector (Stratagene). The G>A transition on the last nucleotide of exon 6 was obtained by site-directed mutagenesis (Stratagene) on a 258 bp PCR fragment, which was then cloned into the Eco47RI/Nsi I sites.

The phenotype of KI mice appeared normal and they were viable for up to two years (Vignier et al., 2009, Circ Res, 105:239-248). Echocardiography was performed on wild-type (WT) and homozygous KI mice using the Vevo 2100 System (VisualSonics, Toronto, Canada). Mice were anesthetized with isofluorane (1-2%) and fixed to a warming platform in a supine position. Bmode images were obtained using a MS400 transducer for adult mice and a MS550 transducer for neonatal mice. Images were obtained in a parasternal short and long axis view and dimensions of the left ventricle were measured in a short axis view in diastole and systole. KI mice exhibited left ventricular hypertrophy, reduced fractional shortening and interstitial fibrosis compared to WT mice at 3-4 months after birth (Vignier et al., 2009, Circ Res, 105:239-248).

Figure 1:
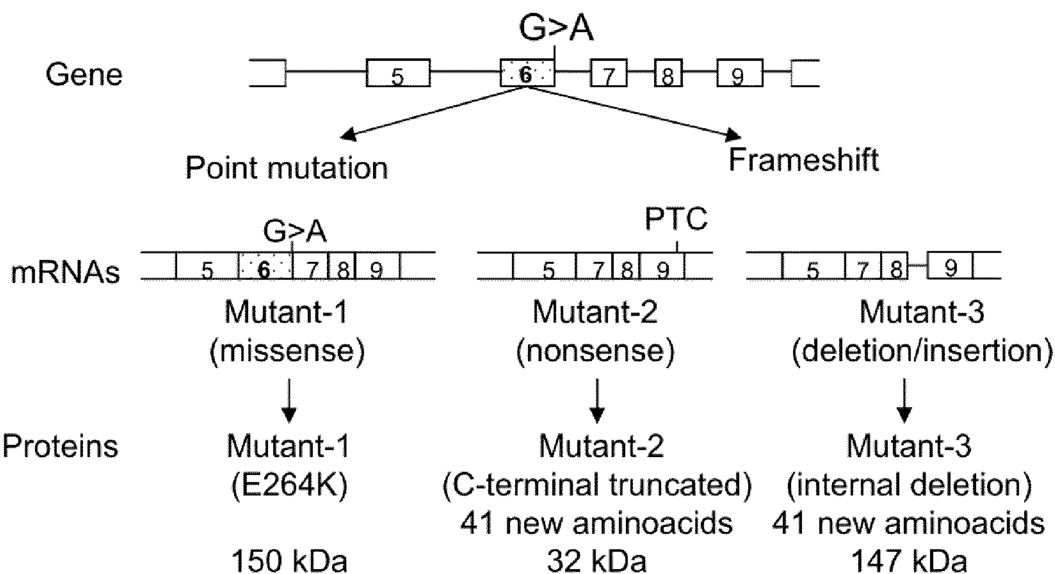
FIG. 1: Cardiac molecular analysis in Mybpc3-targeted knock-in (KI) and wild-type (WT) mice. (A) The G>A transition in the Mybpc3 gene was obtained using the Cre/lox system and resulted in three different mutant mRNAs in KI mice. (B) Total Mybpc3 mRNA level in WT and homozygous KI mouse ventricular tissue. (C) cMyBP-C protein level in WT and KI ventricular tissue, determined by Western blot using a specific antibody. Number of mice is indicated in the bars.
Figure 1:
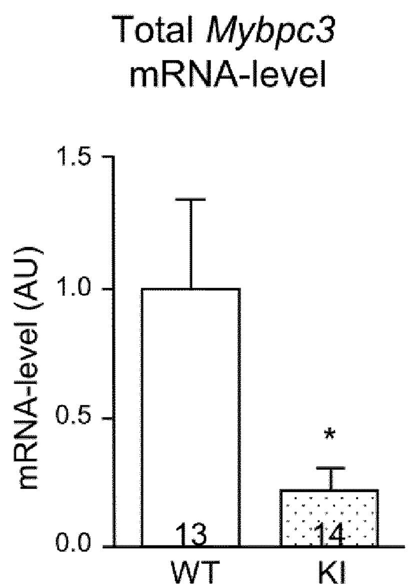
Figure 1:
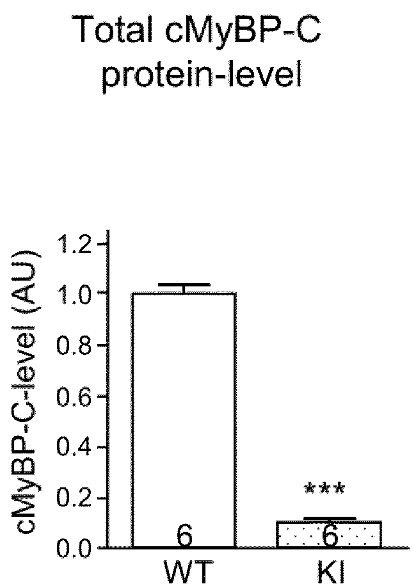

The G>A transition resulted in three different mutant mRNAs (see FIG. 1A). Mutant 1 (missense) contains the G>A transition and produces an E264K mutant protein of about 150 kDa. Mutant 2 (nonsense) is a result from the skipping of exon 6, which leads to a frameshift and a premature termination codon (PTC) in exon 9. The expected protein is 32 kDa. Mutant 3 also results from the skipping of exon 6 and a partial retention of intron 8, which restores the reading frame. In this case, a 147 kDa-mutant protein is produced. None of these mutants encodes a functional protein.

RNA or protein was extracted from ventricular tissue of homozygous KI and WT mice. Total RNA was isolated from ventricular tissue (30 mg) using the SV Total RNA Isolation System Kit (Promega) according to the manufacturer's instructions. RNA concentration, purity and quality were determined using the NanoDrop® ND-1000 spectrophotometer (Thermo Scientific). Reverse transcription (RT) was performed from 150-200 ng RNA using oligo-dT primers (SuperScript®-III kit, Life Technologies). Quantitative polymerase chain reaction (qPCR) was performed using primers #1 (forward: 5'-GGA TTA CAA GGA TGA CGA CGA-3'; SEQ ID NO:9) and #2 (reverse: 5'-TCC AGA GTC CCA GCA TCT TC-3'; SEQ ID NO:10) and SYBR green. The level of total Mybpc3 mRNA was 80% lower in homozygous KI mice than in wild WT mice (FIG. 1B).

Crude protein extract was obtained from about 15 mg of ventricular tissue homogenized in 5% SDS, 50 mM Tris-HCl, pH 7.5, 250 mM sucrose, 75 mM urea, 1 mM DTT at 4° C. and centrifuged at 13000 rpm for 2 min. The supernatant was collected and its concentration was determined using the BCA Protein Assay Kit (Pierce). Proteins were loaded on 10%-acrylamide/bisacrylamide (29:1) gels and electrotransferred on a 0.45 m pore size nitrocellulose membrane (Invitrogen). Membranes were stained with a polyclonal antibody directed against cMyBP-C(C0-C1 1:1,000). The secondary antibody was coupled to HRP (Sigma). Signal was revealed with SuperSignal® West Pico chemiluminescent substrate (Pierce) and acquired with a Chemilmager™ 5500 (Alpha Innotech). Quantification of the signal was done using the NIH Image 1.63 software. Homozygous Mybpc3-targeted knock-in mice expressed only low levels of mutant proteins (FIG. 1C).

The results show that the presence of low levels of cMyBP-C proteins (=haploinsufficiency), including mutant polypeptides (=poison-polypeptides) results in left ventricular hypertrophy and dysfunction, which are hallmarks of HCM.

Example 2: Generation of a FLAG-Mybpc3-Containing Vector

Figure 2:
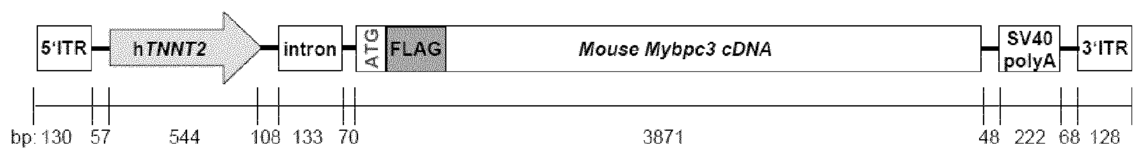
FIG. 2: Schematic linear (upper panel) and circular (lower panel) representations of the pGG2 vector expressing FLAG-tagged mouse Mybpc3 under the control of the human cardiac troponin T promoter (hTNNT2).
Figure 2:
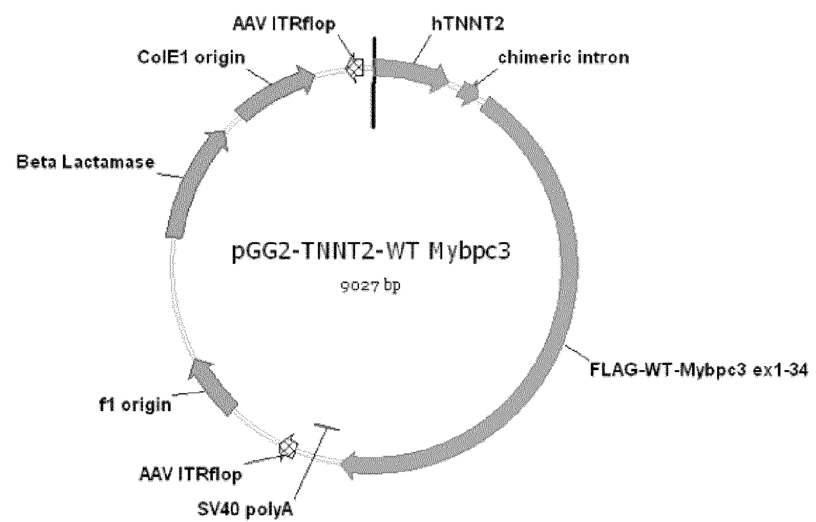

The vector pGG2-hTNNT2-WT-Mybpc3 was constructed by first amplifying the full-length FLAG-tagged mouse Mybpc3 cDNA (GenBank accession number NM_008653.2) including exons 1-34 by RT-PCR from mouse ventricular RNA using the forward primer #3 (5'-TTC GAC CTC GAG ATG GAT TAC AAG GAT GAC GAC GAT AAG CCT GGT GTG ACT GTT CTC AA-3'; SEQ ID NO: 11) containing the XhoI restriction site and the FLAG sequence and reverse primer #4 (5'-TTC GAC GGA TCC CTG GTC ACT GAG GAA CTC G-3'; SEQ ID NO:12) containing BamHI restriction site. The human cardiac troponin T (hTNNT2) 5' region from base −502 to +42 (GenBank accession number NG_007556.1; SEQ ID NO:5) was originally amplified from a human cDNA library by PCR using forward primer #5 (5'-AAA AAA ACG CGT CTC AGT CCA TTA GGA GCC AGT AGC-3'; SEQ ID NO:13) and reverse primer #6 (5'-CCC CCC CAA GCT TCT GCC GAC AGA TCC TGG AGG CG-3'; SEQ ID NO:14) enabling cloning with MluII/HindIII restriction enzymes in a plasmid containing a *renilla* luciferase reporter gene (pdsTNNT2(−502+42)-Rluc) and the chimeric (O-globin/Ig) intron, which has been shown to increase gene expression (Dominguez et al., 2011, Hum Mol Genet 20, 681-93). For generation of the pGG2-hTNNT2-WT-Mybpc3 plasmid the hTNNT2 promoter and the chimeric intron (SEQ ID NO:7; FIG. 2) were excised with the restriction enzymes EcoRI and NheI and ligated into the pGG2 plasmid vector containing the SV polyA signal (SEQ ID NO:6). Together the vector has a size of 9027 bp (FIG. 2), including 5.4 kbp of insert between two ITRs (FIG. 2), which exceeds the packaging capacity of adeno-associated virus (AAV; Wu et al., 2010, Mol Ther 18:80-86).

AAV6 and AAV9 pseudotyped vectors were produced with the two (AAV6; Muller et al., 2006, Cardiovasc Res 70:70-78) or the three (AAV9; Kaya et al., 2011, Cardiovasc Res 91:116-123) plasmids transfection method. AAV6 pseudotyped vectors were generated by co-transfection of HEK293T cells with the pGG2-hTNNT2-WT-Mybpc3 transfer plasmid and the AAV packaging plasmid pDP6rs, which provides the AAV2 rep and AAV6 cap genes and adenoviral helper functions (Grimm et al., 2003, Mol Ther, 7:839-850). AAV9 pseudotyped vectors were generated by triple-transfection of pGG2-hTNNT2-WT-Mybpc3 transfer plasmid with p5E18-VD2-9 and pDGdeltaVP encoding adenoviral helper functions (Kaya et al., 2011, Cardiovasc Res 91:116-23). Generation of recombinant AAV6 and AAV9 particles was carried out as described previously (Grieger et al., 2006, Nat Protoc 1:1412-1428), with some modifications. Plasmids were transfected into 293T HEK cells in cell stacks or in plates with a diameter of 15 cm using polyethylenimine (PEI) as described before (Hauswirth et al., 2000, Methods Enzymol 316:743-761). The HEK293T-AAV cells were cultivated in DMEM, High Glucose supplemented with 10% (v/v) heat-inactivated fetal calf serum, 0.1 mM MEM non-essential amino acids, 2 mM L-glutamine, 100 UI/ml penicillin and 100 μg/ml streptomycin. Tissue culture reagents were obtained from Life technologies. Cells were harvested after 72 h, washed three times with phosphate-buffered saline (PBS). After three freeze-thaw cycles, benzonase (Merck; 250 U/ml) was added for 1 h at 37° C. Cell debris was pelleted and vector-containing lysates were purified using iodixanol step gradients (Hauswirth et al., 2000, Methods Enzymol 316:743-761).

The genomic titers of DNase-resistant AAV particles were determined by qPCR using the SYBR Green qPCR Master MIX 2 (Fermentas) and an ABI PRISM® 7900HT cycler (Applied Biosystem) as reported before (Veldwijk et al., 2002, Mol Ther 6:272-278). Vectors were quantified using primers #7 (forward: 5'-CTC AGT CCA TTA GGA GCC AGT-3'; SEQ ID NO:15) and #8 (reverse: 5'-AAG GCA ACC TCC AAG ACA CT-3'; SEQ ID NO:16) specific for TNNT2 promoter sequence. Real-time PCR was performed in a total volume of 10 μl with 0.3 μM for each primer. The pdsAAV-TNNT2-eGFP plasmid was used as a copy number standard. A standard curve for quantification was generated by serial dilutions of the respective plasmid DNA. The cycling conditions were as follows: 50° C./2 min, 95° C./10 min, followed by 35 cycles of 95° C./15 sec and 60° C./60 sec. Calculations were done using the SDS 2.4 software (Applied Biosystem).

Example 3: Evaluation of Mybpc3 mRNA and cMyBP-C Protein Levels and Localisation after Gene Transfer in Cardiac Myocytes Isolated from Mybpc3-Targeted Neonatal KI Mice Neonatal mouse cardiac myocytes were isolated from neonatal mouse hearts as previously described (Vignier et al., 2009, Circ Res 105:239-248). Cardiac myocytes were immediately transduced with AAV6-FLAG-Mybpc3 under the control of hTNNT2 at a multiplicity of infection (MOI) of 3000 for 30 min at 37° C. in suspension prior to plating ($4.4\times10^5$ cells/well). Cardiac myocytes were kept in culture for 7 days at 37° C. and 10% $CO_2$ prior to harvesting.

HEK293 cells were plated at a density of $2\times10^5$ cells in 12-well dishes in DMEM (10% FCS, 1% penicillin-streptomycin) and incubated at 37° C. with 7% $CO_2$ until the recommended confluence of 50-70% was reached. The transient transfection of FLAG-Mybpc3 plasmid into adherent HEK293 cells was performed using the TurboFect transfection reagent (Fermentas) according to the manufacturer's protocol.

Figure 3:
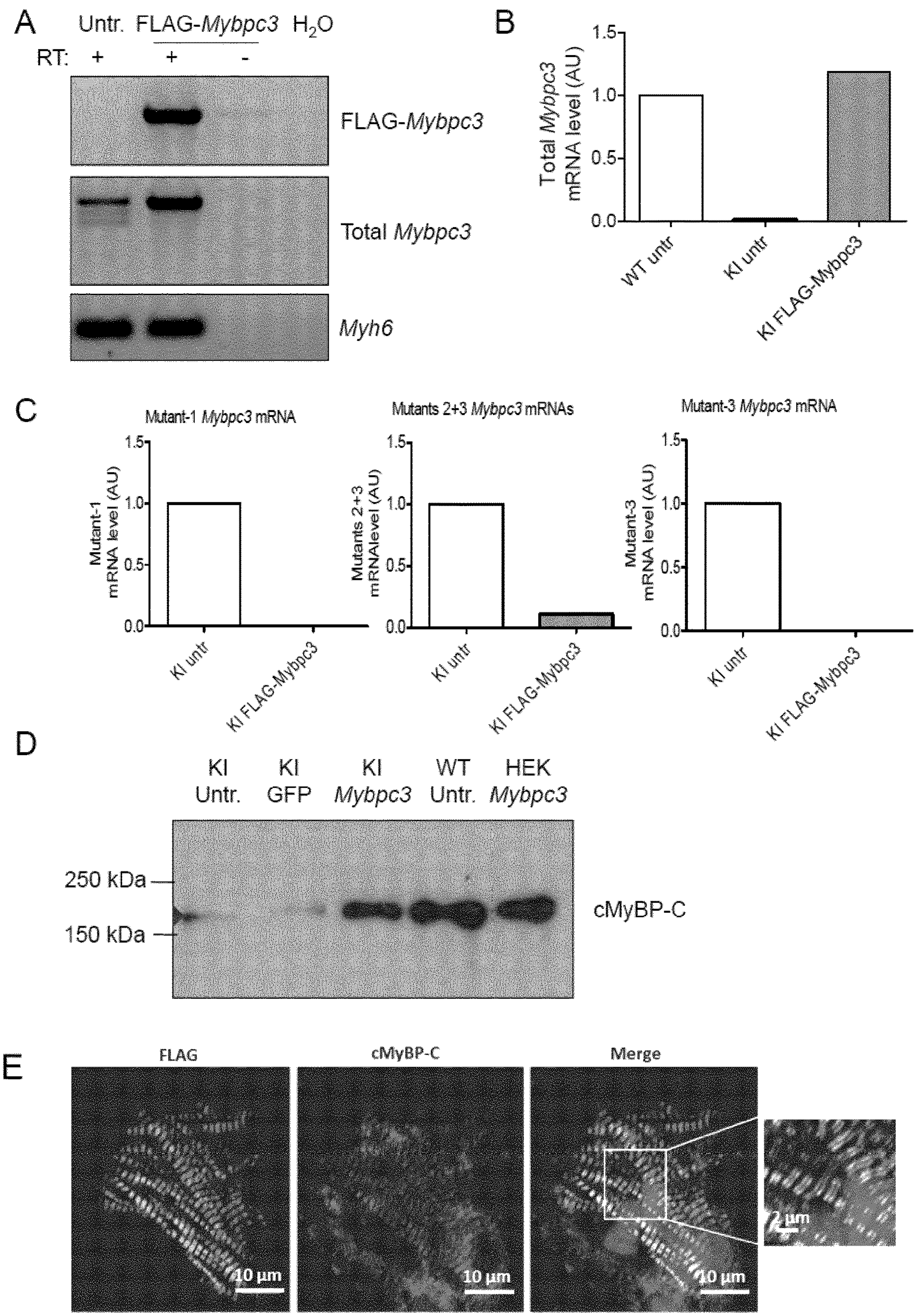
FIG. 3: AAV6-mediated FLAG-Mybpc3 gene transfer using adeno-associated virus serotype 6 in cardiac myocytes isolated from Mybpc3-targeted knock-in (KI) neonatal mice. (A) RTPCR of FLAG-Mybpc3 (exogenous Mybpc3 mRNA), total Mybpc3 (endogenous and exogenous Mybpc3 mRNAs) and Myh6 (encoding $\alpha$-myosin-heavy chain) mRNAs performed in KI ventricular RNA. "—RT" indicates no reverse transcriptase during the cDNA reaction. (B) RT-qPCR of total Mybpc3 evaluated in cardiac myocytes isolated from wild-type (WT) and KI neonatal mice, which were transduced (KI FLAG-Mybpc3) or untransduced (KI untr) with AAV6-FLAGMybpc3. (C) RT-qPCR detecting the different mutant Mybpc3 mRNAs. (D) Western blot performed with an anti-cMyBP-C antibody on protein lysates extracted from WT cardiac myocytes, KI cardiac myocytes, or from HEK293 (HEK) cells, which were transduced with GFP (GFP), or with FLAG-Mybpc3 (Mybpc3) or not transduced (untr.). (E) Immunofluorescence analysis of FLAG-Mybpc3-transduced KI neonatal mouse cardiomyocytes (NMCMs). Cardiac myocytes were fixed 7 days after transduction (MOI 3,000) and double-stained with anti-FLAG (FLAG) and anti-cMyBP-C (cMyBP-C) antibodies. Nuclei were stained with DRAQ5™. The merge picture including its higher magnification is shown on the right panel. Scale bars are indicated.

Total RNA was isolated from cultured cardiac myocytes using the SV Total RNA Isolation System Kit (Promega) according to the manufacturer's instructions. RNA concentration, purity and quality were determined using the NanoDrop® ND-1000 spectrophotometer (Thermo Scientific). RT was performed from 150-200 ng RNA using oligo-dT primers (SuperScript®-III kit, Life Technologies). As a control for genomic contamination a reaction without RT was performed. Touch-down PCR amplifications (65° C.-60° C.) were performed using AmpliTaq® Gold Polymerase (Applied Biosystems) in a total volume of 20 μl for 35 cycles with different primer pairs: FLAG-Mybpc3 mRNA was amplified using forward primer #9 (5'-GGA TTA CAA GGA TGA CGA CGA-3'; SEQ ID NO:17) and reverse primer #10 (5'-TCC AGA GTC CCA GCA TCT TC3'; SEQ ID NO:18); total Mybpc3 mRNA was amplified with forward primer #11 (5'-CCT GGT GTG ACT GTT CTC AA-3'; SEQ ID NO:19) and reverse primer #12 (5'-TCC AGA GTC CCA GCA TCT TC-3'; SEQ ID NO:20); Myh6 mRNA (encoding α-myosin heavy chain) was amplified with forward primer #13 (5'-CTC AAG CTC ATG GCT ACA CTC TTC TC-3'; SEQ ID NO:21) and reverse primer #14 (5'-AGA GCA GAC ACT GTT TGG AAG GA-3'; SEQ ID NO:22). PCR products were visualized on 1.5% agarose gels (FIG. 3A). In untransduced cells (Untr.), only mutant mRNAs were detected (total Mybpc3 panel). In contrast, after AAV6-FLAGMybpc3 gene transfer in KI cardiac myocytes, FLAG-Mybpc3 mRNA was detected (FLAGMybpc3 panel) and was associated with a reduced level of mutant mRNAs (total Mybpc3 panel). The level of Myh6 did not differ between the groups (Myh6 panel). Quantitative PCR using forward primer #15 (5'-GAT GCG AGC CCT GAT GAC-3'; SEQ ID NO:23) and reverse primer #16 (5'-GAC TTG AGA CAC TTT CTT CC-3'; SEQ ID NO:24) and SYBR green demonstrated further that the level of total Mybpc3 mRNA in KI cardiac myocytes transduced with AAV6-FLAG-Mybpc3 reached the level found in WT cardiac myocytes (FIG. 3B). Moreover, quantitative PCR using specific hydrolysing Taqman probes were performed to determine the level of the different mutant mRNAs: Mutant-1 was revealed with probe #1 (5'-VIC-CTC ACT GTC CAT AAG G-MGB-3'; SEQ ID NO:25), mutants 2+3 with probe #2 (5'-FAM-CCA GCA AGA GGC CA-MGB-3'; SEQ ID NO:26) and mutant 3 with probe #3 (5'-FAM-TCG GAG AAC CAG CCC CTG CTA GCT C-TAMRA-3'; SEQ ID NO:27). This shows that mutant-1 and mutant-3 mRNA are completely absent, whereas levels of mutant-2 mRNA are markedly reduced in KI cardiac myocytes from KI transduced with AAV6-FLAG-Mybpc3 (FIG. 3C).

Crude proteins from transduced cultured cardiac myocytes or transfected HEK293 cells were extracted in lysis buffer (30 mM Tris base pH 8.8, 5 mM EDTA, 30 mM NaF, 3% SDS, 10% glycerol) and protein concentration was determined by Bradford protein assay (BioRad). Total proteins (cardiac myocytes 30 μg/lane, HEK293 2.5 μg/lane) were separated on 10% SDS-polyacrylamide (29:1) minigels (BioRad) and transferred on PVDF membranes by electroblotting. Membranes were stained overnight with the primary antibody directed against the MyBP-C motif of cMyBP-C (1:1,000). After incubation with anti-rabbit (1:6,000, Sigma) peroxidase-conjugated secondary antibodies, proteins were visualized using Super Signal® West Dura detection reagent (Thermo Scientific) and signals were detected with the ChemiGenius$^2$ Bio Imaging System. Western blot analysis shows a specific cMyBP-C band in all lanes. Furthermore, the cMyBP-C levels in AAV6-FLAG-Mybpc3-transduced KI cardiac myocytes reached the levels found in untransduced WT cardiac myocytes (FIG. 3D).

Figure 4:
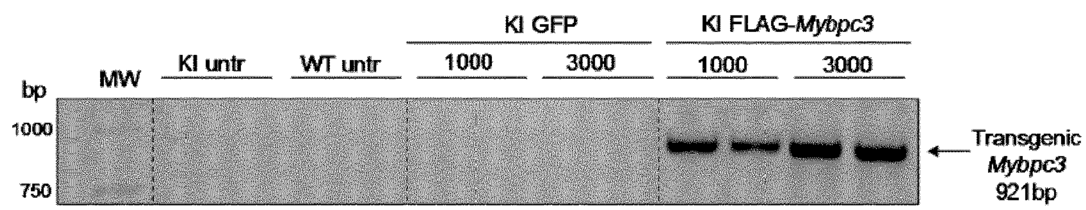
FIG. 4: AAV6-mediated FLAG-Mybpc3 gene transfer in engineered heart tissue (EHT) derived from Mybpc3-targeted knock-in (KI) cardiac cells. (A) RT-PCR from EHT RNA performed using specific primers to detect only FLAG-Mybpc3 mRNA. (B) RT-PCR of total Mybpc3 mRNA. (C) Spontaneous contractile activity of EHT determined at days 7, 9, 14 and 19 of culture. Data are expressed as mean±SEM. $^{*}P<0.05$ and $^{**}P<0.01$ vs. GFP; $^{\#}P<0.05$ and $^{\#\#}P<0.01$ vs Ctrl.
Figure 4:
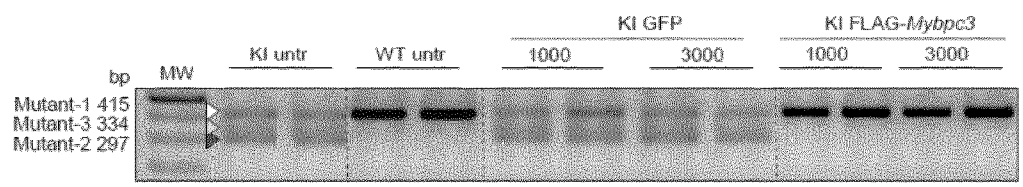
Figure 4:
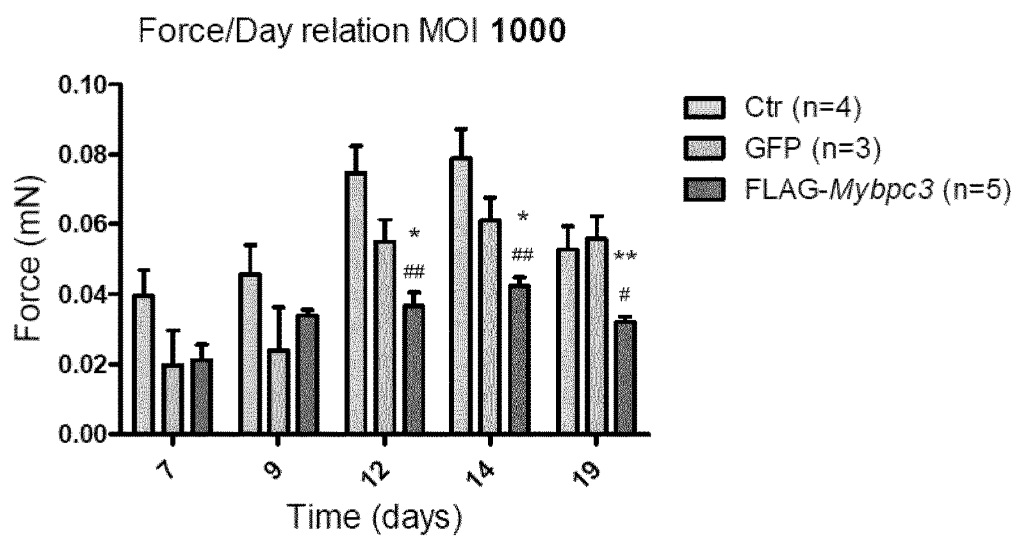

Immunofluorescence analysis was performed in order to examine the localization of the transgenic FLAG-tagged cMyBP-C protein (FIG. 4D). KI cardiac myocytes transduced with AAV6-TNNT2-FLAG-WT-Mybpc3 (MOI 3,000) were analyzed by confocal microscopy after fixation of the cells and staining with antibodies directed against the FLAG epitope and total full-length cMyBP-C protein. Immunofluorescence of transduced cardiac myocytes using the anti-cMyBP-C antibody showed the classic striation pattern of total cMyBP-C protein located in doublets in the A-band of the sarcomere (FIG. 4D, cMyBP-C). Furthermore, FLAG-positive signal (FIG. 4D; FLAG) colocalized with cMyBP-C protein striation, confirming the correct sarcomeric incorporation of the transgenic FLAG-tagged cMyBP-C protein.

These data demonstrate that Mybpc3 gene transfer in KI cardiac myocytes rescues cMyBP-C haploinsufficiency and at the same time prevents transcription of mutant alleles and accumulation of toxic mutant cMyBP-C proteins.

Example 4: Expression of Endogenous Mutant and Exogenous Wild-Type Mybpc3 after Gene Transfer in Engineered Heart Tissues Derived from Mybpc3-Targeted KI Neonatal Hearts Hearts derived from wild-type (WT) and Mybpc3-targeted knock-in (KI) neonatal mice were taken (postnatal day 0-1) for cell isolation using a trypsin/collagenase overnight digestion (Laugwitz et al., 2005, Nature 433:647-653; Moretti et al., 2006, Cell 127:1151-65). To generate engineered heart tissue (EHT), a reconstitution mix was prepared on ice as follows (final concentration): Unpurified $6.8\times10^6$ cells/ml, 5 mg/ml bovine fibrinogen (stock solution: 200 mg/ml plus aprotinin, 0.5 μg/mg fibrinogen in NaCl 0.9%, Sigma F4753), 100 μl/ml Matrigel (BD Bioscience 356235). 2×DMEM was added to match the volumes of fibrinogen and thrombin stock (100 U/ml, Sigma Aldrich T7513) to ensure isotonic conditions. Casting molds were prepared as previously described (Hansen et al., 2010, Circ Res 107:35-44).

AAV6-FLAG-Mybpc3 or AAV6-FLAG-GFP, or a control without virus was added directly into the EHT master mix before casting, at a MOI of 1000 or 3000. The volume of 2×DMEM was adapted to the volume of virus to maintain isotonic conditions. For each EHT a 97-glreconstitution mix was mixed briefly with 3 μl thrombin and pipetted into the agarose slot. For fibrinogen polymerization, the constructs were placed in a 37° C., 7% $CO_2$ humidified cell culture incubator for 2 h. The racks were transferred to 24-well plates filled with culture medium. EHTs were kept in a 37° C., 7% $CO_2$ humidified cell culture incubator. Cell culture medium was changed after 48 h and consisted of DMEM (Biochrom F0415), 10% horse serum (Gibco 26050), 2% chick embryo extract, 1% Penicillin/Streptomycin (Gibco 15140), insulin (10 μg/ml, SigmaAldrich 19278) and aprotinin (33 μg/ml, Sigma Aldrich A1153). On day 5 of the EHT culture, cytosine β-D-arabinofuranoside (25 μg/ml, Sigma-Aldrich C1768) was added to the culture medium for 48 h. Spontaneous contractile activity of EHTs was monitored from day 7 to day 19 via video-optical recording (Hansen, et al., 2010, Circ Res 107, 35-44). Contraction graphs were automatically recorded and evaluated. The CTMV software (Pforzheim, Germany) was used to measure spontaneous contractions of murine EHTs as recently published (Hansen et al., 2010, Circ Res 107:35-44; St6 hr et al., 2013, J Mol Cell Cardiol 63:189-98). For this purpose, the 24-well plate was placed in a cell incubator unit with control of $CO_2$, humidity and temperature, and a glass roof for monitoring purposes. A Basler camera (Type A 602f-2) was placed above the cell culture unit in a PC-controlled manner. During measuring time the distance between the ends of the muscle strip was recorded during contractions. The force was calculated according to a recently published equation (Vandenburgh et al., 2008, Muscle Nerve, 37:438-47) based on post geometry, elastic modulus of Sylgard 184 (Dow Corning) and delta of post distance (post deflection). Squares in recorded contraction graphs indicated the identified peaks, which were taken for frequency, average force, contraction and relaxation times (T1, T2, respectively) calculation. T1 and T2 were determined at 10% of peak maximum. At the end of the experiments, EHTs were removed from posts, and total RNA was extracted.

FLAG-Mybpc3 mRNA was amplified as described in the Example 3 and detected only in transduced EHTs, and its level increased with increasing MOI (FIG. 4A). In addition, PCR amplification of all types of Mybpc3 mRNAs (Total Mybpc3, as described in Example 3) revealed that (FIG. 4B): i) the different mutant mRNAs were detected at a similar level in both untransduced KI-EHT and in EHT transduced with AAV6-GFP; ii) FLAG-Mybpc3 gene transfer in KI EHTs lead to a single type of mRNA. The level of this mRNA did not differ from the level detected in WT-EHT. This shows that gene transfer of FLAG-Mybpc3 repaired the mRNA haploinsufficiency and reduced the content of mutant mRNAs in EHT derived from KI neonatal cardiac cells.

Spontaneous contractile activity of EHTs was monitored from day 7 to day 19 of culture via video optical recording (FIG. 4C). In all groups, maximum force was reached at 14 days. The developed force is higher in KI (about 65 giN) than in WT EHTs (about 40 giN, data not shown), indicating hypercontractility. The developed force was significantly lower after Mybpc3 gene transfer in KI EHT than in other groups (FIG. 4C), reaching levels previously found in WT EHTs.

Together, these data show that gene transfer of FLAG-Mybpc3 in EHT derived from KI neonatal cardiac cells rescues both the molecular phenotype (no haploinsufficiency and no mutant mRNAs) and the function (absence of hypercontractility).

Example 5: Expression of Endogenous Mutant and Exogenous Wild-Type Mybpc3 after Gene Transfer in Mybpc3-Targeted KI Neonatal Mice All experimental in vivo studies were in accordance with the guidelines for the care and use of laboratory animals published by the NIH (Publication No. 85-23, revised 1985) as well as the German Law for the Protection of Animals and accepted by the Ministry of Science and Public Health of the City State of Hamburg, Germany (Nr. 69/10).

AAV9-FLAG-Mybpc3 ($5\times10^{12}$ vector genomes (vg)) or PBS as a control were administered in 3-day-old mice via temporal vein injection using a 30-G needle (Sands and Barker, 1999, Lab Anim Sci, 49:328-330) as described previously (Dominguez et al., 2011, Hum Mol Genet 20:681-693). All mice recovered quickly from the injection. The cardiac phenotype was evaluated every week from 3 weeks of age by echocardiography (see details in Example 1). The mice were sacrificed at 7 weeks of age and different organs were extracted. RNA and proteins were extracted. FLAGMybpc3 and total Mybpc3 mRNAs in ventricles, liver and skeletal muscle were evaluated by RTPCR as described in Example 3 (FIG. 5A).

Figure 5:
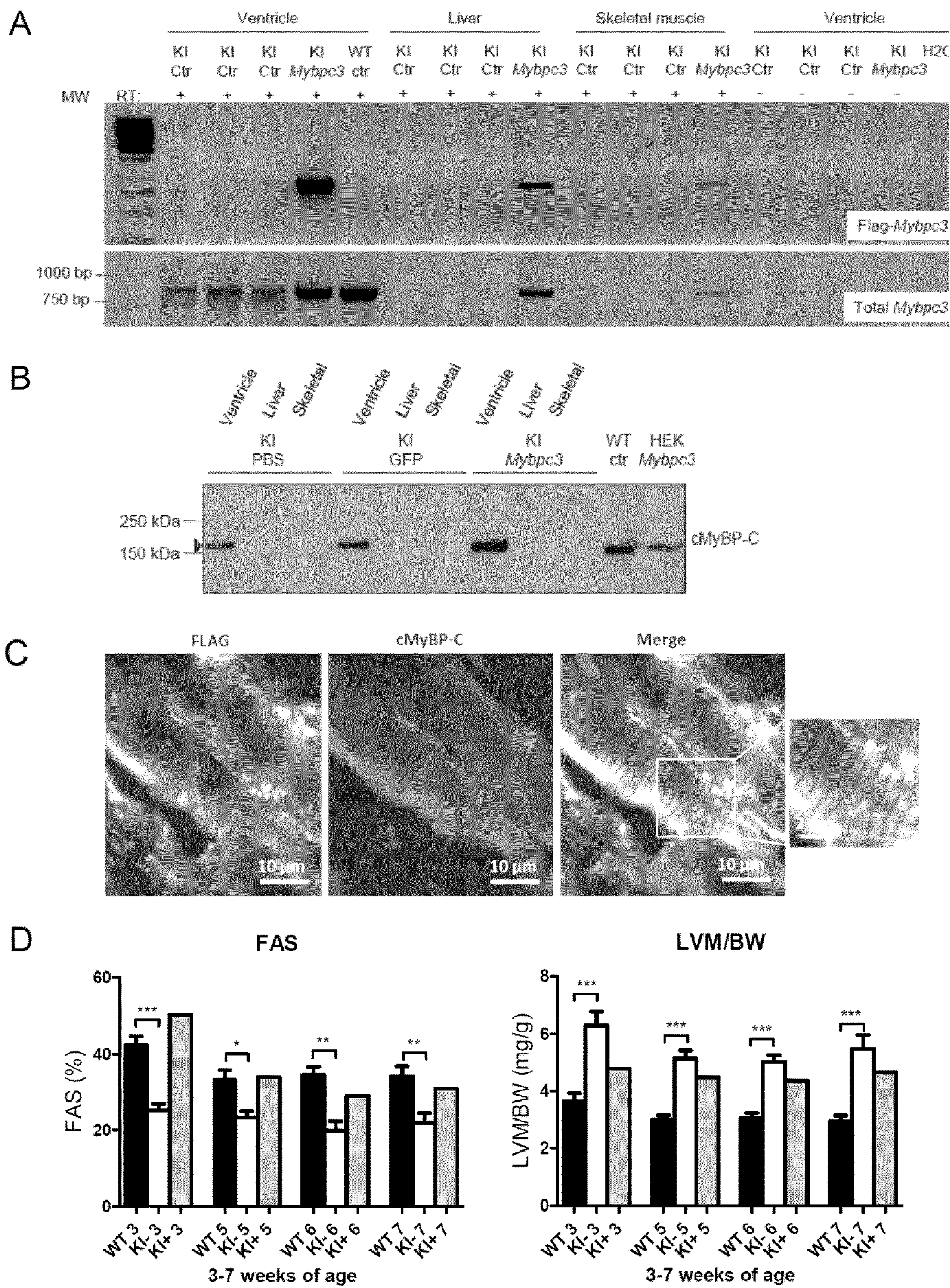
FIG. 5: AAV9-mediated FLAG-Mybpc3 gene transfer in neonatal Mybpc3-targeted knockin mouse. (A) RT-PCR of FLAG-tagged and total Mybpc3 mRNAs were evaluated by RT-PCR in ventricles, liver and skeletal muscle. Ctr: PBS administration. (B) cMyBP-C protein determination in Western blot of proteins extracted from ventricles, liver and skeletal muscle. (C) Immunofluorescence analysis of myocardial sections of AAV9-FLAG-Mybpc3-transduced KI mouse. AAV9-FLAG-Mybpc3 was administered into the temporal vein of 1-day-old KI mice for 7 weeks. Cryosections (10-µm thickness) were stained with antibodies directed against FLAG and cMyBP-C. The merge picture, including its higher magnification is shown on the right panel. Immunofluorescence analysis was performed by confocal microscopy with a 40×-oil objective. Scale bars are indicated. (D) Fractional area shortening (FAS) and left ventricular mass-to-body weight (LVM/BW) ratio were determined by echocardiography in wild-type (WT), PBS-treated knock-in (KI−) and KI injected with AAV9-FLAG-Mybpc3 (KI+). Evaluations were performed at 3, 5, 6 and 7 weeks of age. Data are expressed as mean±SEM. $^{*}P<0.05$, $^{}P<0.01$ and $^{*}P<0.001$ vs. WT mice.

The level of FLAG-Mybpc3 mRNA was much higher in the ventricles than in other organs (FIG. 5A, upper FLAG-Mybpc3 panel). In the ventricles, the different mutant Mybpc3 mRNAs were amplified in the control KI mice (FIG. 5A, lower total Mybpc3 panel), whereas a major unique band was detected in wild-type control mouse and in the KI mouse transduced with AAV9-FLAG-Mybpc3 (FIG. 5A, total Mybpc3 panel). A band was also detected in liver and skeletal muscle after FLAG-Mybpc3 gene transfer, although at a lower level than in the ventricles.

Western blot analyses was performed as described in Example 3 using an antibody directed against cMyBP-C and revealed that the cMyBP-C protein level after AAV9-FLAG-Mybpc3 gene transfer is higher than in PBS- or AAV9-GFP-injected KI mice and reached the level found in WT mouse (FIG. 5B). cMyBP-C protein was not detected in the liver and skeletal muscle after Mybpc3 gene transfer (FIG. 5B), due to the cardiac-specificity of the vector.

In order to examine the localization of the exogenously expressed FLAG-tagged cMyBP-C protein, immunofluorescence analysis was performed on ventricular cryosections of the KI mouse injected with AAV9-FLAG-Mybpc3 for 7 weeks using antibodies directed against FLAG epitope and total cMyBP-C protein. The staining showed the classic striation pattern of the cMyBP-C protein located in doublets in the A-band of the sarcomere (FIG. 5C; cMyBP-C), which entirely co-stained with the FLAG signal (FIG. 5C; FLAG). Nuclei were stained with DRAQ5™. Taken together, the overexpressed cMyBP-C protein was properly incorporated within the sarcomere and the majority of FLAG-positive-striated cardiomyocytes were co-stained with total cMyBP-C protein, suggesting that exogenous cMyBP-C protein replaced the endogenous mutant ones.

Echocardiographic analyses were performed as described in Example 1 above. Fractional area shortening (FAS) and left ventricular mass-to-body weight (LVM/BW) ratio were examined in wild-type (WT), PBS-injected knock-in (KI−) mice and KI mice injected with AAV9-FLAGMybpc3 (KI+) at 3, 5, 6 and 7 weeks of age. Evaluation of the cardiac function by echocardiography showed a rescue of the fractional area shortening (FAS) and a reduction of the left ventricular mass-to-body weight (LVM/BW) ratio after FLAG-Mybpc3 gene transfer (FIG. 5D).

Together, these data showed that a single administration of AAV9-FLAG-Mybpc3 in neonatal KI mice rescues the molecular phenotype (no cMyBP-C haploinsufficiency and no mutant polypeptides) and the functional phenotype (no left ventricular hypertrophy and dysfunction).

Example 6: Expression of Exogenous Wild-Type Myc-MYBPC3 in Human Cardiac Myocytes Derived from Induced-Pluripotent Stem Cells Induced pluripotent stem cells (iPSC) were generated by reprogramming of fibroblasts expanded from a skin biopsy of a human control individual. Cardiac myocyte differentiation was adapted from a protocol from the group of Gordon Keller (Yang L et al., 2008, Nature 22:524-8).

After differentiation, human cardiac myocytes were plated at a density of $2\times10^5$ cells/well in a 12-well plate for RNA and protein analysis, or $2.5\times10^4$ cells/chamber in a four chamber dish (35-mm diameter) for immunofluorescence analysis. Cardiac myocytes were transduced for 8 days with a myc-tagged MYBPC3 adenovirus encoding human myc-cMyBP-C (DNA sequence: SEQ ID NO:29 followed by SEQ ID NO:1) at different MOI.

Construction of the myc-tagged human MYBPC3 plasmid was described previously (Flavigny J et al., 1999, J Mol Biol 294, 443-456; Sarikas et al., 2005, Cardiovasc Res 66:33-44). Briefly, an ATG plus 30-nucleotide sequence (SEQ ID NO:29) encoding the myc epitope (SEQ ID NO:30) was inserted behind the CMV promoter (SEQ ID NO:31) and before the human MYBPC3 cDNA (SEQ ID NO: 1). The insert encodes a myc-tagged human cMyBP-C(SEQ ID NO:32). Recombinant adenovirus were generated by cloning the insert (myc-tagged human MYBPC3 cDNA) into the shuttle vector pAdTrack-CMV and subsequent cotransformation of this plasmid with pAdEasy-1 into *Escherichia coli* as described previously (He T et al., 1998 Proc Natl Acad Sci USA 95, 2509-2514). Expression of cMyBP-C is driven by the constitutively active CMV promoter (SEQ ID NO:31).

Figure 6:
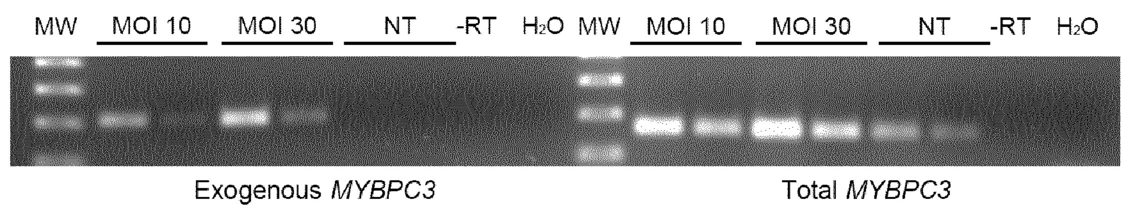
FIG. 6: Expression of exogenous human myc-MYBPC3 in human cardiac myocytes. Human cardiac myocytes were derived from human induced-pluripotent stem cells (iPSC) and transduced with adenovirus (MOI of 10 or 30) encoding myc-tagged human MYBPC3._(A) RT-PCR of exogenous myc-MYBPC3 in iPSC-derived human cardiac myocytes. Exogenous MYBPC3 mRNA was amplified with specific primers; total MYBPC3 mRNA amplified with primers that recognized both exogenous and endogenous MYBPC3. (B) Exogenous myc-cMyBP-C protein levels in human cardiac myocytes derived from iPSC. Western blot analysis was performed using antibody directed either the myc tag sequence (=exogenous myc-cMyBP-C) or against the CO-C1 domains of cMyBP-C (=total cMyBP-C). Positive control (+) corresponds to a sample of murine cardiac myocytes transduced with the same adenovirus. (C) Localization of exogenous human myccMyBP-C in human cardiac myocytes derived from iPSC, analysed by immunofluorescence; cMyBP-C: anti-cMyBP-C antibody; myc: anti-myc antibody, i.e. exogenous cMyBP-C. Scale bars are indicated in the figure. Abbreviations: NT, not transduced; MOI, multiplicity of infection; −RT, no reverse transcriptase.
Figure 6:
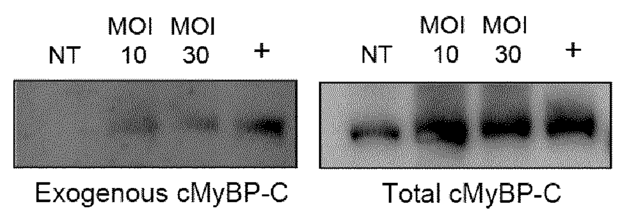
Figure 6:
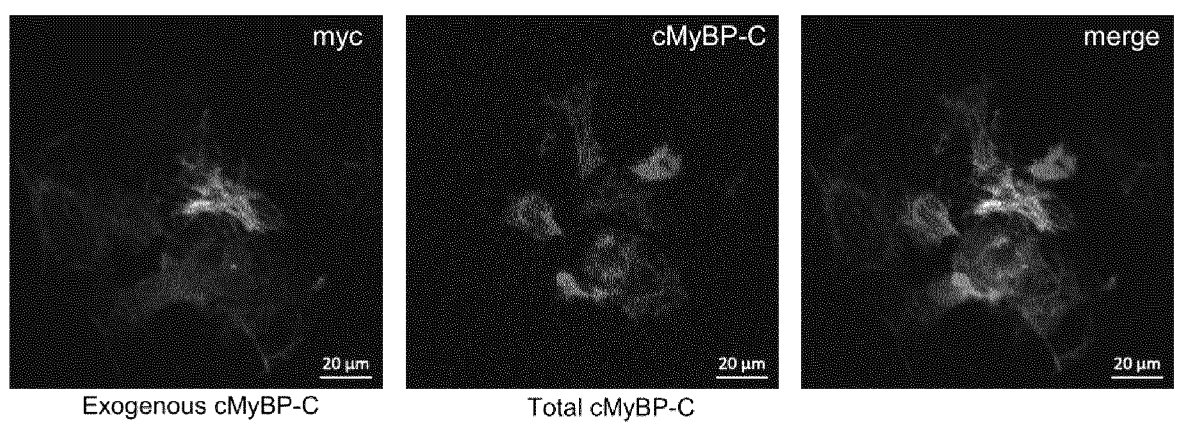

The evaluation of the transcription of the different MYBPC3 mRNAs (exogenous myc-MYBPC3 and total MYBPC3) in human cardiac myocytes was performed by RT-PCR as described before (FIG. 6A). Exogenous MYBPC3 mRNA was amplified with specific primers (Forward primer in the myc sequence, 5'-GCA AAA GCT TAT TAG CGA GGA A-3' (SEQ ID NO:33) and reverse primer in exon 2, 5'-CAG GCC GTA CTT GTT GCT G-3' (SEQ ID NO:34)), and total MYBPC3 mRNA with primers that recognized both exogenous and endogenous MYBPC3 (Forward primer in exon 1, 5'-GGG GAA GAA GCC AGT CTC AG-3' (SEQ ID NO:35) and reverse primer in exon 2, 5'-CAG GCC GTA CTT GTT GCT G-3' (SEQ ID NO:34)). The level of Myc-MYBPC3 mRNA increased with increasing virus dose (FIG. 6A, left panel). No Myc-MYBPC3 mRNA was detected in non-transduced cells (NT) and in negative controls lacking reverse transcriptase (RT).

Western blot analysis was performed as described before using antibodies directed either against the CO-C1 domains of cMyBP-C (FIG. 6B, total cMyBP-C, kindly given by collaborator) or against the myc tag (FIG. 6B, exogenous myc-cMyBP-C (rabbit polyclonal Sigma; catalog #C3956). The positive control (+) was a sample of murine cardiac myocytes transduced with the same virus. The level of total cMyBP-C was slightly increased after adenoviral gene transfer, whereas the myc-tagged cMyBP-C protein was absent in non-transduced (NT) sample and its level increased with increasing MOI (FIG. 6B).

Localization of exogenous myc-cMyBP-C in human cardiac myocytes derived from iPSC was analysed by immunofluorescence. Human cardiac myocytes were stained with anti-cMyBP-C antibody (FIG. 6C, cMyBP-C), which showed expected sarcomeric striations. Exogenous cMyBP-C was stained with the anti-myc antibody (FIG. 6C, myc). The anti-myc antibody binds to the myc tag, which is located at the N-terminus of the protein. It was observed that exogenous myc-tagged cMyBP-C was correctly incorporated into the sarcomere of human iPSC-derived cardiac myocytes as a doublet in the A band.

These data showed for the first time expression of exogenous human myc-MYBPC3 in human cardiac myocytes derived from iPSC. Expression of exogenous human myc-MYBPC3 resulted in a stable human cMyBP-C protein, which is incorporated into the sarcomere. Thus, overexpression of MYBPC3 cDNA may be used for gene therapy in human hypertrophic cardiomyopathy.

Example 7: Long-Term Mybpc3 Gene Therapy Restored Mybpc3 mRNA Level and Partially Prevented Cardiac Hypertrophy and Dysfunction in Mybpc3-Targeted Knock-in Mice Different doses of adeno-associated virus serotype 9 (AAV9)-Mybpc3 ($1\times10^{11}$, $3\times10^{11}$, $1\times10^{12}$ and $3\times10^{12}$ vector genomes (vg)/mouse) or PBS were administered into the temporal vein of 1-day-old Mybpc3-targeted knock-in (KI) mice, before the appearance of the cardiac disease phenotype. After 34 weeks, mice were subjected to in vivo hemodynamics and tissue analysis. WT mice were used as controls.

Analyses of systolic (=dP/dtmax) and diastolic (=dP/dtmin) function and determination of the heart weight to body weight ratio (HW/BW) were performed in 34-week-old WT, KI treated with PBS and KI mice treated with the highest dose of $3\times10^{12}$ vg (FIG. 7.1 A). Compared to WT, the slight reduction in systolic function, the marked reduction in diastolic function and the marked increase in HW/BW ratio were prevented by Mybpc3 gene therapy in KI mice.

Further, RT-PCR was performed for evaluation of the mRNA levels of exogenous FLAG-tagged Mybpc3 (FIG. 7.1 B, upper panel) and total Mybpc3 (lower panel). RNA was extracted from ventricular tissues and pooled in each group (n=5-10/group). The size of the PCR-amplified bands is shown on the left side of FIG. 7.1 B. This shows that the expression of Mybpc3 (both exogenous alone and total) increased in a AAV9-Mybpc3 dose-dependent manner. Importantly and conversely, the expression of mutant mRNAs (as represented by the amplicons for mutant-1, mutant-2 and mutant-3) decreased in a AAV9-Mybpc3 dose-dependent manner.

Moreover, total Mybpc3 mRNA level was determined by RT-qPCR performed in 34-week-old WT, KI treated with PBS and KI mice treated with the highest dose of $3\times10^{12}$ vg (FIG. 7.1 C). Compared to WT, the marked reduction in Mybpc3 mRNA level was fully prevented by Mybpc3 gene therapy in KI mice.

Western blot analysis was performed for evaluation of the protein levels of exogenous FLAGtagged cMyBP-C (FIG. 7.2 D, upper panels) and total cMyBP-C (lower panels). Ventricular protein extracts from each group were pooled for the analysis. Blots were stained with antibodies directed against the FLAG epitope or total cMyBP-C (upper part in each condition). An antibody directed against GAPDH was used as loading control (lower parts in each condition). As for the Mybpc3 mRNA, this shows that the protein level of cMyBP-C (both exogenous alone and total) increased in a AAV9-Mybpc3 dose-dependent manner.

cMyBP-C protein level was quantified, normalized to GAPDH and related to WT (FIG. 7.2 E). Compared to WT, the marked reduction in cMyBP-C protein level was significantly prevented by Mybpc3 gene therapy in KI mice.

Taken together, these data showed that long-term Mybpc3 gene therapy not only restored the level of Mybpc3 WT in KI mice but also prevented the transcription of mutant Mybpc3 mRNAs. Both partially significantly prevented the development of left ventricular hypertrophy and diastolic dysfunction, which are the key features of hypertrophic cardiomyopathy.

The invention claimed is:

1. A gene therapy vector for expressing an exogenous nucleic acid sequence comprising:

(a) a nucleic acid sequence encoding a functional cardiac myosin binding protein C (cMyBP-C), and (b) a human cardiac troponin T (hTNNT2) promoter which is operably linked to said nucleic acid sequence, wherein said gene therapy vector, and wherein the hTNNT2 promoter comprises a nucleic acid sequence at least 95% identical over its length compared to SEQ ID NO: 5 is an adeno-associated virus (AAV) vector.

2. The gene therapy vector of claim 1, wherein the hTNNT2 promoter comprises the nucleic acid sequence of SEQ ID NO: 5.

3. The gene therapy vector of claim 1 wherein said cMyBP-C protein comprises the cMyBP-C amino acid sequence of SEQ ID NO: 2 or a functional variant thereof having at least 80% sequence identity thereto.

4. The gene therapy vector of claim 1, wherein said cMyBP-C protein comprises the cMyBP-C amino acid sequence of SEQ ID NO: 2 or a functional variant thereof having at least 90% sequence identity thereto.

5. The gene therapy vector of claim 1, wherein said cMyBP-C protein comprises the cMyBP-C amino acid sequence of SEQ ID NO: 2.

6. The gene therapy vector of claim 3, further comprising an intron which increases gene expression levels, said intron comprising a fragment of beta globin gene intron.

7. The gene therapy vector of claim 3, further comprising intron sequences from the human beta globin gene and human immunoglobulin G (IgG).

8. The gene therapy vector of claim 3, further comprising an intron comprising the nucleic acid sequence of SEQ ID NO: 7.

9. The gene therapy vector of claim 1, wherein the AAV vector is an AAV serotype 1 vector, AAV serotype 6 vector, AAV serotype 8 vector, or AAV serotype 9 vector.

10. The gene therapy vector of claim 1, wherein the nucleic acid sequence encoding the functional cMyBP-C protein and the hTNNT2 promoter are within a polynucleotide insert having a size of at least 4.0 kbp, up to 5.4 kbp.

11. The gene therapy vector of claim 1, wherein the nucleic acid sequence encoding the functional cMyBP-C protein and the hTNNT2 promoter are within a polynucleotide insert having a size of at least 4.5 kbp, up to 5.4 kbp.

12. The gene therapy vector of claim 3, wherein the nucleic acid sequence encoding the functional cMyBP-C protein and the hTNNT2 promoter are within a polynucleotide insert having a size of at least 4.0 kbp, up to 5.4 kbp.

13. The gene therapy vector of claim 3, wherein the nucleic acid sequence encoding the functional cMyBP-C protein and the hTNNT2 promoter are within a polynucleotide insert having a size of at least 4.5 kbp, up to 5.4 kbp.

14. The gene therapy vector of claim 1 comprising (a) a hTNNT2 promoter that comprises the nucleic acid sequence of SEQ ID NO: 5, (b) a nucleic acid sequence encoding the cMyBP-C amino acid sequence of SEQ ID NO: 2, and (c) an intron comprising the nucleic acid sequence of SEQ ID NO: 7.

15. The gene therapy vector of claim 1 comprising:

(a) a hTNNT2 promoter that comprises the nucleic acid sequence of SEQ ID NO: 5, and (b) a nucleic acid sequence encoding the cMyBP-C amino acid sequence of SEQ ID NO: 2.

* * * * *

UNITED STATES PATENT AND TRADEMARK OFFICE

CERTIFICATE OF CORRECTION

PATENT NO. : 11,773,408 B2
APPLICATION NO. : 16/707223
DATED : October 3, 2023
INVENTOR(S) : Carrier et al.

It is certified that error appears in the above-identified patent and that said Letters Patent is hereby corrected as shown below:

In the Claims

Column 73, Lines 38-40, Claim 1, delete the text ", and wherein the hTNNT2 promoter comprises a nucleic acid sequence at least 95% identical over its length compared to SEQ ID NO: 5"

Column 73, Line 41, Claim 1, after "adeno-associated virus (AAV) vector" insert the following text --, and wherein the hTNNT2 promoter comprises a nucleic acid sequence at least 95% identical over its length compared to SEQ ID NO: 5--.

Signed and Sealed this
Thirtieth Day of January, 2024

Katherine Kelly Vidal

Katherine Kelly Vidal
*Director of the United States Patent and Trademark Office*